United States Patent
Chen et al.

(10) Patent No.: US 11,001,639 B2
(45) Date of Patent: May 11, 2021

(54) CHIMERIC ANTIGEN RECEPTOR FOR EFFICIENT SELECTIVE PROLIFERATION IN VITRO AND USES THEREOF

(71) Applicant: Xuanwu Hospital Capital Medical University, Beijing (CN)

(72) Inventors: Zhiguo Chen, Beijing (CN); Yu Zhao, Beijing (CN)

(73) Assignee: Xuanwu Hospital Capital Medical University, Beijing (CN)

( * ) Notice: Subject to any disclaimer, the term of this patent is extended or adjusted under 35 U.S.C. 154(b) by 274 days.

(21) Appl. No.: 16/255,803

(22) Filed: Jan. 23, 2019

(65) Prior Publication Data
US 2019/0233532 A1    Aug. 1, 2019

(30) Foreign Application Priority Data

Jan. 24, 2018 (CN) .......................... 201810068562.8

(51) Int. Cl.
| | | |
|---|---|---|
| C07K 16/28 | (2006.01) | |
| A61P 35/02 | (2006.01) | |
| A61K 39/00 | (2006.01) | |
| C07K 14/725 | (2006.01) | |
| A61K 35/17 | (2015.01) | |
| C07K 14/705 | (2006.01) | |
| A61K 47/65 | (2017.01) | |
| A61P 35/04 | (2006.01) | |

(52) U.S. Cl.
CPC .......... *C07K 16/2896* (2013.01); *A61K 35/17* (2013.01); *A61K 39/0011* (2013.01); *A61K 47/65* (2017.08); *A61P 35/02* (2018.01); *A61P 35/04* (2018.01); *C07K 14/7051* (2013.01); *C07K 14/70517* (2013.01); *C07K 16/2803* (2013.01); *A61K 2039/5156* (2013.01); *A61K 2039/5158* (2013.01); *C07K 2317/622* (2013.01); *C07K 2319/02* (2013.01); *C07K 2319/03* (2013.01); *C07K 2319/33* (2013.01)

(58) Field of Classification Search
CPC combination set(s) only.
See application file for complete search history.

(56) References Cited

U.S. PATENT DOCUMENTS 10,253,086 B2 * 4/2019 Bitter ...................... A61P 35/00

FOREIGN PATENT DOCUMENTS

| | | | |
|---|---|---|---|
| CN | 105142677 A | 12/2015 | |
| CN | 107227335 A | 10/2017 | |
| WO | WO-2006078273 A2 * | 7/2006 | ............. C07K 14/52 |
| WO | WO-2006099481 A2 * | 9/2006 | ............. C07K 16/00 |
| WO | WO-2014127261 A1 * | 8/2014 | ......... A61K 47/6891 |

OTHER PUBLICATIONS

Cartellieri M, Koristka S, Arndt C, Feldmann A, Stamova S, et al, A Novel Ex Vivo Isolation and Expansion Procedure for Chimeric Antigen Receptor Engrafted Human T Cells, PLoS One, Apr. 3, 2014.

Lingfeng Liu et al, Inclusion of Strep-Tag II in design of antigen receptors for T cell immunotherapy, Nat Biotechnol, Apr. 30, 2016.

* cited by examiner

*Primary Examiner* — Brad Duffy
*Assistant Examiner* — Cheom-Gil Cheong

(57) ABSTRACT

Chimeric antigen receptors for efficient and selective in vitro proliferation and uses thereof. Specifically, the present invention provides a CAR-encoding molecule with specific selectivity in vitro. By introducing a humanized selective domain into the molecule, the CAR-positive cells after being infected can be efficiently sorted via a secondary sorting step. Upon exposure to the selective domain-specific antibody, the CAR-transduced immune cells can be selectively expanded; therefore, the ratio of the CAR-positive target cells in the final product is significantly increased, improving the efficiency of preparing CAR gene-modified immune cell products. The present invention provides a more reliable technical support for further promotion and application of such products in clinical practice.

4 Claims, 56 Drawing Sheets

Specification includes a Sequence Listing.

SEQUENCE LISTING

<160> NUMBER OF SEQ ID NOS: 14

<210> SEQ ID NO 1
<211> LENGTH: 63
<212> TYPE: DNA
<213> ORGANISM: Artificial Sequence
<220> FEATURE:
<223> OTHER INFORMATION: synthetic

<400> SEQUENCE: 1

```
atggcgctgc cggtgaccgc gctgctgctg ccgctggcgc tgctgctgca tgcggcgcgt    60
ccg                                                                  63
```

-continued

```
<210> SEQ ID NO 2
<211> LENGTH: 207
<212> TYPE: DNA
<213> ORGANISM: Artificial Sequence
<220> FEATURE:
<223> OTHER INFORMATION: synthetic

<400> SEQUENCE: 2
accaccaccc cggcgccgcg tccgccgacc ccggcgccga ccattgcgag ccagccgctg      60
agcctgcgtc cggaagcgtg ccgtccggcg gcgggcggcg cggtgcatac ccgtggcctg     120
gattttgcgt gcgatattta tatttgggcg ccgctggcgg gcacctgcgg cgtgctgctg     180
ctgagcctgg tgattaccct gtattgc                                         207

<210> SEQ ID NO 3
<211> LENGTH: 462
<212> TYPE: DNA
<213> ORGANISM: Artificial Sequence
<220> FEATURE:
<223> OTHER INFORMATION: synthetic

<400> SEQUENCE: 3
aaacgtggcc gtaaaaaact gctgtatatt tttaaacagc cgtttatgcg tccggtgcag      60
accacccagg aagaagatgg ctgcagctgc cgttttccgg aagaagaaga aggcggctgc     120
gaactgcgtg tgaaatttag ccgtagcgcg gatgcgccgg cgtataaaca gggccagaac     180
cagctgtata cgaactgaa cctgggccgt cgtgaagaat atgatgtgct ggataaacgt      240
cgtggccgtg atccggaaat gggcggcaaa ccgcgtcgta aaacccgca ggaaggcctg      300 tataacgaac tgcagaaaga taaaatggcg gaagcgtata gcgaaattgg catgaaaggc     360
gaacgtcgtc gtggcaaagg ccatgatggc ctgtatcagg gcctgagcac cgcgaccaaa     420
gatacctatg atgcgctgca tatgcaggcg ctgccgccgc gt                         462

<210> SEQ ID NO 4
<211> LENGTH: 30
<212> TYPE: DNA
<213> ORGANISM: Artificial Sequence
<220> FEATURE:
<223> OTHER INFORMATION: synthetic

<400> SEQUENCE: 4
aaaccgctgc cggaagtgac cgatgaatat                                       30

<210> SEQ ID NO 5
<211> LENGTH: 372
<212> TYPE: DNA
<213> ORGANISM: Artificial Sequence
<220> FEATURE:
<223> OTHER INFORMATION: synthetic

<400> SEQUENCE: 5
caggtgcagc tgcagcagag cggcgcggaa ctggtgcgtc cgggcagcag cgtgaaaatt      60
agctgcaaag cgagcggcta tcgtttagc agctattgga tgaactgggt gaaacagcgt     120
ccgggccagg gcctggaatg gattggccag atttggccgg cgatggcga taccaactat      180 aacggcaaat ttaaaggcaa agcgaccctg accgcggatg aaagcagcag caccgcgtat     240
atgcagctga gcagcctggc gagcgaagat agcgcggtgt attttgcgc gcgtcgtgaa     300 accaccaccg tggccgtta ttattatgcg atggattatt ggggccaggg caccaccgtg     360
accgtgagca gc                                                         372
```

<210> SEQ ID NO 6
<211> LENGTH: 333
<212> TYPE: DNA
<213> ORGANISM: Artificial Sequence
<220> FEATURE:
<223> OTHER INFORMATION: synthetic

<400> SEQUENCE: 6

```
gatattcagc tgacccagag cccggcgagc tggcggtga gcctgggcca gcgtgcgacc      60
attagctgca aagcgagcca gagcgtggat tatgatggcg atagctatct gaactggtat    120
cagcagattc cgggccagcc gccgaaactg ctgatttatg atgcgagcaa cctggtgagc    180
ggcattccgc cgcgttttag cggcagcggc agcggcaccg attttaccct gaacattcat    240
ccggtggaaa aagtggatgc ggcgacctat cattgccagc agagcaccga agatccgtgg    300
acctttggcg gcggcaccaa actggaaatt aaa                                 333
```

<210> SEQ ID NO 7
<211> LENGTH: 1500
<212> TYPE: DNA
<213> ORGANISM: Artificial Sequence
<220> FEATURE:
<223> OTHER INFORMATION: synthetic

<400> SEQUENCE: 7

```
atggctctgc cagtgacagc tctgctgctg cctctggctc tgctgctgca cgcagctaga     60
ccccaggtgc agctgcagca gtcaggagca gaactcgtga gaccaggcag cagcgtgaag    120
atctcttgca aggccagcgg ctacgccttc tctagctatt ggatgaattg ggtgaagcag    180
cggccaggac agggactgga gtggattgga cagatttggc ccggcgacgg cgataccaac    240
tacaacggca gttcaagggg caaggccacc ctgacagccg acgagtctag cagcacagcc    300
tacatgcagc tgagctctct ggccagcgag gatagcgccg tgtacttttg cgccagaagg    360
gagaccacaa cagtgggccg gtactactac gccatggact attggggcca gggcacaacc    420
gtgacagtgt ctagcggagg aggcggctct aagcctctgc cagaagtgac agacgagtac    480
ggcggaggag gaagcgacat ccagctgacc cagagcccag cttctctggc agtgtctctg    540
ggacagaggg ctaccatctc ttgcaaggcc agccagagcg tggattacga cggcgacagc    600
tacctgaatt ggtatcagca gatccccggc cagcctccta agctgctgat ctacgacgcc    660
tccaacctgg tgtccggcat ccctcccaga ttcagcggaa gcggcagcgg cacagacttc    720
accctgaaca tccaccccgt ggagaaggtg gacgccgcca cataccattg ccagcagagc    780
acagaggacc cctggacctt tggcggcgga acaaagctgg atcaagac aaccacccca    840 gcccctagac tcctacacc agcccctaca atcgcctctc agcctctgag cctgaggcca    900
gaagcttgta gacccgcagc aggaggagca gtgcatacaa ggggcctgga cttcgcttgc    960
gacatctaca tttgggcccc tctggcagga acttgcggag tgctgctgct gtctctggtc   1020
atcaccctgt attgcaagcg gggccggaag aagctgctgt acatcttcaa gcagcccttc   1080
atgcggccag tgcagacaac acaggaggag gacggttgca gctgcagatt cccagaggag   1140
gaggaaggcg gctgcgagct gagagtgaag ttcagcagga gcgccgacgc tccagcctat   1200
aaacagggac agaaccagct gtacaacgag ctgaacctgg gcagaagaga ggagtacgac   1260
gtgctggaca gaggagagg cagagaccca gagatgggcg gcaagcctag aaggaagaac   1320
ccccaggagg gcctgtacaa cgagctgcag aaggacaaga tggccgaggc ttacagcgag   1380
atcggcatga agggcgagag gagaagaggc aaaggccacg acggactgta tcagggactg   1440
```
agcacagcca ccaaggacac ctacgacgct ctgcacatgc aggctctgcc tcctagataa    1500

<210> SEQ ID NO 8
<211> LENGTH: 499
<212> TYPE: PRT
<213> ORGANISM: Artificial Sequence
<220> FEATURE:
<223> OTHER INFORMATION: synthetic

<400> SEQUENCE: 8

```
Met Ala Leu Pro Val Thr Ala Leu Leu Leu Pro Leu Ala Leu Leu Leu
1               5                   10                  15

His Ala Ala Arg Pro Gln Val Gln Leu Gln Gln Ser Gly Ala Glu Leu
            20                  25                  30

Val Arg Pro Gly Ser Ser Val Lys Ile Ser Cys Lys Ala Ser Gly Tyr
        35                  40                  45

Ala Phe Ser Ser Tyr Trp Met Asn Trp Val Lys Gln Arg Pro Gly Gln
    50                  55                  60

Gly Leu Glu Trp Ile Gly Gln Ile Trp Pro Gly Asp Gly Asp Thr Asn
65                  70                  75                  80

Tyr Asn Gly Lys Phe Lys Gly Lys Ala Thr Leu Thr Ala Asp Glu Ser
                85                  90                  95

Ser Ser Thr Ala Tyr Met Gln Leu Ser Ser Leu Ala Ser Glu Asp Ser
            100                 105                 110

Ala Val Tyr Phe Cys Ala Arg Arg Glu Thr Thr Thr Val Gly Arg Tyr
        115                 120                 125

Tyr Tyr Ala Met Asp Tyr Trp Gly Gln Gly Thr Thr Val Thr Val Ser
    130                 135                 140

Ser Gly Gly Gly Gly Ser Lys Pro Leu Pro Glu Val Thr Asp Glu Tyr
145                 150                 155                 160

Gly Gly Gly Gly Ser Asp Ile Gln Leu Thr Gln Ser Pro Ala Ser Leu
                165                 170                 175

Ala Val Ser Leu Gly Gln Arg Ala Thr Ile Ser Cys Lys Ala Ser Gln
            180                 185                 190

Ser Val Asp Tyr Asp Gly Asp Ser Tyr Leu Asn Trp Tyr Gln Gln Ile
        195                 200                 205

Pro Gly Gln Pro Pro Lys Leu Leu Ile Tyr Asp Ala Ser Asn Leu Val
    210                 215                 220

Ser Gly Ile Pro Pro Arg Phe Ser Gly Ser Gly Ser Gly Thr Asp Phe
225                 230                 235                 240

Thr Leu Asn Ile His Pro Val Glu Lys Val Asp Ala Ala Thr Tyr His
                245                 250                 255

Cys Gln Gln Ser Thr Glu Asp Pro Trp Thr Phe Gly Gly Gly Thr Lys
            260                 265                 270

Leu Glu Ile Lys Thr Thr Thr Pro Ala Pro Arg Pro Pro Thr Pro Ala
        275                 280                 285

Pro Thr Ile Ala Ser Gln Pro Leu Ser Leu Arg Pro Glu Ala Cys Arg
    290                 295                 300

Pro Ala Ala Gly Gly Ala Val His Thr Arg Gly Leu Asp Phe Ala Cys
305                 310                 315                 320

Asp Ile Tyr Ile Trp Ala Pro Leu Ala Gly Thr Cys Gly Val Leu Leu
                325                 330                 335

Leu Ser Leu Val Ile Thr Leu Tyr Cys Lys Arg Gly Arg Lys Lys Leu
            340                 345                 350
```

```
Leu Tyr Ile Phe Lys Gln Pro Phe Met Arg Pro Val Gln Thr Thr Gln
            355                 360                 365

Glu Glu Asp Gly Cys Ser Cys Arg Phe Pro Glu Glu Glu Gly Gly
    370                 375                 380

Cys Glu Leu Arg Val Lys Phe Ser Arg Ser Ala Asp Ala Pro Ala Tyr
385                 390                 395                 400

Lys Gln Gly Gln Asn Gln Leu Tyr Asn Glu Leu Asn Leu Gly Arg Arg
                405                 410                 415

Glu Glu Tyr Asp Val Leu Asp Lys Arg Gly Arg Asp Pro Glu Met
            420                 425                 430

Gly Gly Lys Pro Arg Arg Lys Asn Pro Gln Glu Gly Leu Tyr Asn Glu
        435                 440                 445

Leu Gln Lys Asp Lys Met Ala Glu Ala Tyr Ser Glu Ile Gly Met Lys
    450                 455                 460

Gly Glu Arg Arg Arg Gly Lys Gly His Asp Gly Leu Tyr Gln Gly Leu
465                 470                 475                 480

Ser Thr Ala Thr Lys Asp Thr Tyr Asp Ala Leu His Met Gln Ala Leu
                485                 490                 495

Pro Pro Arg

<210> SEQ ID NO 9
<211> LENGTH: 263
<212> TYPE: PRT
<213> ORGANISM: Artificial Sequence
<220> FEATURE:
<223> OTHER INFORMATION: synthetic

<400> SEQUENCE: 9

Met Ala Leu Pro Val Thr Ala Leu Leu Leu Pro Leu Ala Leu Leu Leu
1               5                   10                  15

His Ala Ala Arg Pro Asp Ile Gln Met Thr Gln Thr Thr Ser Ser Leu
                20                  25                  30

Ser Ala Ser Leu Gly Asp Arg Val Thr Ile Ser Cys Arg Ala Ser Gln
            35                  40                  45

Asp Ile Ser Lys Tyr Leu Asn Trp Tyr Gln Gln Lys Pro Asp Gly Thr
        50                  55                  60

Val Lys Leu Leu Ile Tyr His Thr Ser Arg Leu His Ser Gly Val Pro
65              70                  75                  80

Ser Arg Phe Ser Gly Ser Gly Ser Gly Thr Asp Tyr Ser Leu Thr Ile
                85                  90                  95

Ser Asn Leu Glu Gln Glu Asp Ile Ala Thr Tyr Phe Cys Gln Gln Gly
                100                 105                 110

Asn Thr Leu Pro Tyr Thr Phe Gly Gly Gly Thr Lys Leu Glu Ile Thr
            115                 120                 125

Gly Gly Gly Gly Ser Gly Gly Gly Ser Gly Gly Gly Ser Glu
        130                 135                 140

Val Lys Leu Gln Glu Ser Gly Pro Gly Leu Val Ala Pro Ser Gln Ser
145                 150                 155                 160

Leu Ser Val Thr Cys Thr Val Ser Gly Val Ser Leu Pro Asp Tyr Gly
                165                 170                 175

Val Ser Trp Ile Arg Gln Pro Pro Arg Lys Gly Leu Glu Trp Leu Gly
            180                 185                 190

Val Ile Trp Gly Ser Glu Thr Thr Tyr Tyr Asn Ser Ala Leu Lys Ser
        195                 200                 205

Arg Leu Thr Ile Ile Lys Asp Asn Ser Lys Ser Gln Val Phe Leu Lys
```

```
                210                 215                 220
Met Asn Ser Leu Gln Thr Asp Asp Thr Ala Ile Tyr Tyr Cys Ala Lys
225                 230                 235                 240

His Tyr Tyr Gly Gly Ser Tyr Ala Met Asp Tyr Trp Gly Gln Gly
            245                 250                 255

Thr Ser Val Thr Val Ser Ser
            260
```

<210> SEQ ID NO 10
<211> LENGTH: 10
<212> TYPE: PRT
<213> ORGANISM: Artificial Sequence
<220> FEATURE:
<223> OTHER INFORMATION: synthetic

<400> SEQUENCE: 10

```
Gly Gly Gly Gly Ser Gly Gly Gly Gly Ser
1               5                   10
```

<210> SEQ ID NO 11
<211> LENGTH: 15
<212> TYPE: DNA
<213> ORGANISM: Artificial Sequence
<220> FEATURE:
<223> OTHER INFORMATION: synthetic

<400> SEQUENCE: 11
ggcggcggcg gcagc                                                           15

<210> SEQ ID NO 12
<211> LENGTH: 497
<212> TYPE: PRT
<213> ORGANISM: Artificial Sequence
<220> FEATURE:
<223> OTHER INFORMATION: synthetic

<400> SEQUENCE: 12

```
Met Ala Leu Pro Val Thr Ala Leu Leu Leu Pro Leu Ala Leu Leu Leu
1               5                   10                  15

His Ala Ala Arg Pro Gln Val Gln Leu Gln Gln Ser Gly Ala Glu Leu
            20                  25                  30

Val Arg Pro Gly Ser Ser Val Lys Ile Ser Cys Lys Ala Ser Gly Tyr
        35                  40                  45

Ala Phe Ser Ser Tyr Trp Met Asn Trp Val Lys Gln Arg Pro Gly Gln
    50                  55                  60

Gly Leu Glu Trp Ile Gly Gln Ile Trp Pro Gly Asp Gly Asp Thr Asn
65                  70                  75                  80

Tyr Asn Gly Lys Phe Lys Gly Lys Ala Thr Leu Thr Ala Asp Glu Ser
                85                  90                  95

Ser Ser Thr Ala Tyr Met Gln Leu Ser Ser Leu Ala Ser Glu Asp Ser
            100                 105                 110

Ala Val Tyr Phe Cys Ala Arg Arg Glu Thr Thr Thr Val Gly Arg Tyr
        115                 120                 125

Tyr Tyr Ala Met Asp Tyr Trp Gly Gln Gly Thr Thr Val Thr Val Ser
    130                 135                 140

Ser Gly Gly Gly Gly Ser Trp Ser His Pro Gln Phe Glu Lys Gly Gly
145                 150                 155                 160

Gly Gly Ser Asp Ile Gln Leu Thr Gln Ser Pro Ala Ser Leu Ala Val
                165                 170                 175
```

Ser Leu Gly Gln Arg Ala Thr Ile Ser Cys Lys Ala Ser Gln Ser Val
            180                 185                 190

Asp Tyr Asp Gly Asp Ser Tyr Leu Asn Trp Tyr Gln Gln Ile Pro Gly
        195                 200                 205

Gln Pro Pro Lys Leu Leu Ile Tyr Asp Ala Ser Asn Leu Val Ser Gly
    210                 215                 220

Ile Pro Pro Arg Phe Ser Gly Ser Gly Ser Gly Thr Asp Phe Thr Leu
225                 230                 235                 240

Asn Ile His Pro Val Glu Lys Val Asp Ala Ala Thr Tyr His Cys Gln
                245                 250                 255

Gln Ser Thr Glu Asp Pro Trp Thr Phe Gly Gly Gly Thr Lys Leu Glu
            260                 265                 270

Ile Lys Thr Thr Thr Pro Ala Pro Arg Pro Pro Thr Pro Ala Pro Thr
        275                 280                 285

Ile Ala Ser Gln Pro Leu Ser Leu Arg Pro Glu Ala Cys Arg Pro Ala
    290                 295                 300

Ala Gly Gly Ala Val His Thr Arg Gly Leu Asp Phe Ala Cys Asp Ile
305                 310                 315                 320

Tyr Ile Trp Ala Pro Leu Ala Gly Thr Cys Gly Val Leu Leu Leu Ser
                325                 330                 335

Leu Val Ile Thr Leu Tyr Cys Lys Arg Gly Arg Lys Lys Leu Leu Tyr
            340                 345                 350

Ile Phe Lys Gln Pro Phe Met Arg Pro Val Gln Thr Thr Gln Glu Glu
        355                 360                 365

Asp Gly Cys Ser Cys Arg Phe Pro Glu Glu Glu Glu Gly Gly Cys Glu
    370                 375                 380

Leu Arg Val Lys Phe Ser Arg Ser Ala Asp Ala Pro Ala Tyr Lys Gln
385                 390                 395                 400

Gly Gln Asn Gln Leu Tyr Asn Glu Leu Asn Leu Gly Arg Arg Glu Glu
                405                 410                 415

Tyr Asp Val Leu Asp Lys Arg Arg Gly Arg Asp Pro Glu Met Gly Gly
            420                 425                 430

Lys Pro Arg Arg Lys Asn Pro Gln Glu Gly Leu Tyr Asn Glu Leu Gln
        435                 440                 445

Lys Asp Lys Met Ala Glu Ala Tyr Ser Glu Ile Gly Met Lys Gly Glu
    450                 455                 460

Arg Arg Arg Gly Lys Gly His Asp Gly Leu Tyr Gln Gly Leu Ser Thr
465                 470                 475                 480

Ala Thr Lys Asp Thr Tyr Asp Ala Leu His Met Gln Ala Leu Pro Pro
                485                 490                 495

Arg

<210> SEQ ID NO 13
<211> LENGTH: 498
<212> TYPE: PRT
<213> ORGANISM: Artificial Sequence
<220> FEATURE:
<223> OTHER INFORMATION: synthetic

<400> SEQUENCE: 13

Met Ala Leu Pro Val Thr Ala Leu Leu Leu Pro Leu Ala Leu Leu Leu
1               5                   10                  15

His Ala Ala Arg Pro Gln Val Gln Leu Gln Gln Ser Gly Ala Glu Leu
            20                  25                  30

Val Arg Pro Gly Ser Ser Val Lys Ile Ser Cys Lys Ala Ser Gly Tyr

```
                    35                  40                  45
Ala Phe Ser Ser Tyr Trp Met Asn Trp Val Lys Gln Arg Pro Gly Gln
 50                  55                  60

Gly Leu Glu Trp Ile Gly Gln Ile Trp Pro Gly Asp Gly Asp Thr Asn
 65                  70                  75                  80

Tyr Asn Gly Lys Phe Lys Gly Lys Ala Thr Leu Thr Ala Asp Glu Ser
                 85                  90                  95

Ser Ser Thr Ala Tyr Met Gln Leu Ser Ser Leu Ala Ser Glu Asp Ser
                100                 105                 110

Ala Val Tyr Phe Cys Ala Arg Arg Glu Thr Thr Thr Val Gly Arg Tyr
                115                 120                 125

Tyr Tyr Ala Met Asp Tyr Trp Gly Gln Gly Thr Thr Val Thr Val Ser
                130                 135                 140

Ser Gly Gly Gly Gly Ser Asn Trp Ser His Pro Gln Phe Glu Lys Gly
145                 150                 155                 160

Gly Gly Gly Ser Asp Ile Gln Leu Thr Gln Ser Pro Ala Ser Leu Ala
                165                 170                 175

Val Ser Leu Gly Gln Arg Ala Thr Ile Ser Cys Lys Ala Ser Gln Ser
                180                 185                 190

Val Asp Tyr Asp Gly Asp Ser Tyr Leu Asn Trp Tyr Gln Gln Ile Pro
                195                 200                 205

Gly Gln Pro Pro Lys Leu Leu Ile Tyr Asp Ala Ser Asn Leu Val Ser
210                 215                 220

Gly Ile Pro Pro Arg Phe Ser Gly Ser Gly Ser Gly Thr Asp Phe Thr
225                 230                 235                 240

Leu Asn Ile His Pro Val Glu Lys Val Asp Ala Ala Thr Tyr His Cys
                245                 250                 255

Gln Gln Ser Thr Glu Asp Pro Trp Thr Phe Gly Gly Gly Thr Lys Leu
                260                 265                 270

Glu Ile Lys Thr Thr Thr Pro Ala Pro Arg Pro Pro Thr Pro Ala Pro
                275                 280                 285

Thr Ile Ala Ser Gln Pro Leu Ser Leu Arg Pro Glu Ala Cys Arg Pro
                290                 295                 300

Ala Ala Gly Gly Ala Val His Thr Arg Gly Leu Asp Phe Ala Cys Asp
305                 310                 315                 320

Ile Tyr Ile Trp Ala Pro Leu Ala Gly Thr Cys Gly Val Leu Leu Leu
                325                 330                 335

Ser Leu Val Ile Thr Leu Tyr Cys Lys Arg Gly Arg Lys Lys Leu Leu
                340                 345                 350

Tyr Ile Phe Lys Gln Pro Phe Met Arg Pro Val Gln Thr Thr Gln Glu
                355                 360                 365

Glu Asp Gly Cys Ser Cys Arg Phe Pro Glu Glu Glu Glu Gly Gly Cys
                370                 375                 380

Glu Leu Arg Val Lys Phe Ser Arg Ser Ala Asp Ala Pro Ala Tyr Lys
385                 390                 395                 400

Gln Gly Gln Asn Gln Leu Tyr Asn Glu Leu Asn Leu Gly Arg Arg Glu
                405                 410                 415

Glu Tyr Asp Val Leu Asp Lys Arg Arg Gly Arg Asp Pro Glu Met Gly
                420                 425                 430

Gly Lys Pro Arg Arg Lys Asn Pro Gln Glu Gly Leu Tyr Asn Glu Leu
                435                 440                 445

Gln Lys Asp Lys Met Ala Glu Ala Tyr Ser Glu Ile Gly Met Lys Gly
                450                 455                 460
```

```
Glu Arg Arg Arg Gly Lys Gly His Asp Gly Leu Tyr Gln Gly Leu Ser
465                 470                 475                 480

Thr Ala Thr Lys Asp Thr Tyr Asp Ala Leu His Met Gln Ala Leu Pro
                485                 490                 495

Pro Arg

<210> SEQ ID NO 14
<211> LENGTH: 24
<212> TYPE: DNA
<213> ORGANISM: Artificial Sequence
<220> FEATURE:
<223> OTHER INFORMATION: synthetic

<400> SEQUENCE: 14
tggagccatc cgcagtttga aaaa                                          24
```

CHIMERIC ANTIGEN RECEPTOR FOR EFFICIENT SELECTIVE PROLIFERATION IN VITRO AND USES THEREOF

REFERENCE TO AN ELECTRONIC SEQUENCE LISTING

The contents of the electronic sequence listing (Untitled_ST25_20190405.txt; Size: 21,000 bytes; and Date of Creation: Apr. 5, 2019) is herein incorporated by reference in its entirety.

CROSS-REFERENCE TO RELATED APPLICATIONS

This application claims the benefit of priority from Chinese Application No. 201810068562.8, filed on Jan. 24, 2018. The entire content of the aforementioned application, including any intervening amendments thereto, is incorporated herein by reference.

TECHNICAL FIELD

The present application relates to genetic engineering and immunotherapy, and specifically to chimeric antigen receptors for efficient and selective in-vitro proliferation of cells and uses thereof.

BACKGROUND

Chimeric antigen receptors (CARs) are artificial receptor molecules which become chimeric by combining various functional domains such as an antigen-specific antibody, a transmembrane domain and an intracellular co-stimulatory signaling domain. These molecules can directly recognize target cells through expression of domains capable of recognizing the related antigens or antibodies. Immune cells (e.g., T cells) modified by such receptors, upon activation of the intracellular co-stimulatory signaling domain, can directly kill the target cells through cytotoxicity. Compared to the natural T cell killing in vivo, CAR-mediated cytotoxic function is MHC-independent and shows advantages in two folds. On the one hand, the cytotoxic function of effector cells is enhanced; and on the other hand, the recognition and killing of the target cells with MHC molecule mutated are improved.

Currently, genetic modification of CAR is mainly applied to targeted anti-tumor immunotherapy, which is mediated by the immune cells with direct killing, including T cells and NK cells. This immunotherapy is generally directed to hematological malignancies, including refractory or relapsed chronic B-cell lymphoma (CLL), non-Hodgkin lymphoma (NHL) and multiple myeloma (MM), where the targets include CD19, CD20 and CD133. In September 2017, Kymriah, a CD19-mCAR-modified T cell therapeutic product developed by Novartis indicated for children and young adults, has been officially approved by the FDA for the treatment of refractory or relapsed acute B-cell lymphoma (ALL). This is the first approved immune cell product that is genetically modified, indicating that the safety and efficacy of CAR gene-modified therapy have entered a new era.

However, there are still many technical difficulties remained to be overcome in the preparation of CAR-modified immune cells. How to obtain high-purity CAR-positive cells of interest is a common problem. Although different research teams have improved the transduction efficiency of T cells to CAR-encoding viruses by enhancing viral MOI and multiple transduction via electroporation. This increases the ratio of CAR-positive cells to some extent, but the results are still far from being satisfactory.

Therefore, there is a need to generate CAR-positive target cells capable of being efficiently sorted and to find a means to increase the ratio of CAR-positive cells.

SUMMARY

An objective of the present invention is to provide a CAR-positive effector cell capable of being efficiently sorted and a method to increase the ratio of CAR-positive cells.

Another objective of the present invention is to provide a chimeric antigen receptor-engineered immune cell that can be efficiently and selectively expanded in vitro and uses thereof.

In a first aspect, the present invention provides a chimeric antigen receptor of formula (I):

$$F_0\text{-}F_1\text{-}L_1\text{-}Z\text{-}L_2\text{-}F_2\text{-}H\text{-}TM\text{-}C\text{-}CD3\zeta \qquad (I);$$

wherein, $F_0$ is absent or a signal peptide sequence;

one of $F_1$ and $F_2$ is a heavy chain variable region of an anti-human CD19 single-chain antibody, and the other is a light chain variable region of the anti-human CD19 single-chain antibody;

Z is a selective domain with an amino acid sequence as shown in positions 151-160 of SEQ ID NO.8, positions 151-158 of SEQ ID NO.12 or positions 151-159 of SEQ ID NO.13;

$L_1$ and $L_2$ are independently absent or a linker peptide;

H is absent or a hinge region;

TM is a transmembrane domain;

C is absent or a co-stimulatory signal receptor tyrosine-based activation motif

CD3ζ is a cytoplasmic signal transduction sequence; and

"—" is a linker peptide or a peptide bond.

In an embodiment, a length of $F_1\text{-}L_1\text{-}Z\text{-}L_2\text{-}F_2$ (or a length of ScFv and the selective domain) is 237-343 amino acids, preferably 247-303 amino acids.

In an embodiment, lengths of $F_1$ and $F_2$ (i.e., lengths of a light and heavy chains of the ScFv) are each independently 107-130 amino acids, preferably 107-124 amino acids.

In an embodiment, lengths of $L_1$ and $L_2$ are each independently 0-10 amino acids, preferably 0-5 amino acids.

In an embodiment, a length of $L_1\text{-}Z\text{-}L_2$ is 10-30 amino acids, preferably 10-20 amino acids.

In an embodiment, Z is selected from an amino acid sequence at positions 95-104 of a C-terminal domain of human nucleoprotein La/SS-B, and the amino acid sequence is as shown in positions 151-160 of SEQ ID NO.8.

In an embodiment, Z includes a streptavidin II tag having 8 amino acids as shown in positions 151-158 of SEQ ID NO.12 (WSHPQFEK).

In an embodiment, Z includes a streptavidin II tag having 9 amino acids as shown in positions 151-159 of SEQ ID NO.13 (NWSHPQFEK).

In an embodiment, the selective domain does not affect or substantially does not affect the binding of the CAR to a CAR-targeted antigen. "Substantially" means that the ratio of the binding capacity G1 of CAR comprising the selective domain to the targeting antigen to the binding capacity G0 of CAR without the selective domain to the targeting antigen is no less than 80%; that is, G1/G0≥80%, preferably ≥90%, and more preferably ≥95%.

In an embodiment, $F_0$ is a signal peptide of a protein selected from CD8, GM-CSF, CD4, or a combination thereof. Preferably, $F_0$ is a CD8-derived signal peptide.

In an embodiment, $F_0$ has an amino acid sequence as shown in positions 1-21 of SEQ ID NO.8.

In an embodiment, $L_1$ or $L_2$ has a sequence as shown in positions 146-150 (GGGGS) of SEQ ID NO.8, or GGGGSGGGGS (SEQ ID NO.10).

In an embodiment, $F_1$ is a heavy chain variable region or light chain variable region of a single-chain antibody targeting the human CD19 antigen. Preferably, $F_1$ is the heavy chain variable region of the single-chain antibody targeting the human CD19 antigen.

In an embodiment, $F_1$ and $F_2$ are the heavy chain variable region and the light chain variable region of the single-chain antibody targeting the human CD19 antigen. Preferably, $F_1$ and $F_2$ have amino acid sequences as shown in positions 22-145 and 166-276 of SEQ ID NO.8, respectively.

In an embodiment, H is a hinge region of a protein selected from CD8, CD28, CD137, or a combination thereof. Preferably, H is a hinge region of CD8.

In an embodiment, TM is a transmembrane domain of a protein selected from CD8, CD28, or a combination thereof. Preferably, TM is a transmembrane domain of CD8.

In an embodiment, H-TM has an amino acid sequence as shown in positions 277-345 of SEQ ID NO.8.

In an embodiment, C is a co-stimulatory signal molecule of a protein selected from CD28, CD137, OX40, or a combination thereof.

In an embodiment, C-CD3ζ has an amino acid sequence as shown in positions 346-499 of SEQ ID NO.8.

In an embodiment, the chimeric antigen receptor has an amino acid sequence shown as SEQ ID NO.8, SEQ ID NO.12 or SEQ ID NO.13.

In a second aspect, the invention provides an isolated polynucleotide encoding the chimeric antigen receptor (CAR) according to the first aspect of the invention.

In an embodiment, the polynucleotide has a sequence comprising one or more nucleotide sequences selected from the group consisting of:

(1) a coding sequence of $F_0$ shown as SEQ ID NO.1;
(2) a coding sequence of H-TM shown as SEQ ID NO.2;
(3) a coding sequence of C-CD3ζ shown as SEQ ID NO.3;
(4) a coding sequence of Z shown as SEQ ID NO.4; and
(5) coding sequences of $F_1$ and $F_2$ respectively shown as SEQ ID NOs. 5 and 6.

In an embodiment, the polynucleotide has a sequence shown as SEQ ID NO.7.

In a third aspect, the invention provides a vector comprising the polynucleotide according to the second aspect of the present invention.

In an embodiment, the vector is a viral vector, preferably a lentiviral vector.

In a fourth aspect, the invention provides a host cell that expresses the chimeric antigen receptor according to the first aspect of the present invention; and/or integrates with the exogenous polynucleotide according to the second aspect of the present invention into the genome thereof; and/or comprises the vector according to the third aspect of the present invention.

In an embodiment, the host cell is a prokaryotic or eukaryotic cell.

In an embodiment, the host cell is a mammalian cell.
In an embodiment, the host cell is a human cell.
In an embodiment, the host cell is an NK or T cell.

In a fifth aspect, the invention provides a genetically engineered NK or T cell, being a mammalian NK cell or T cell, and on the cell membrane of the NK or T cell is expressed the chimeric antigen receptor according to the first aspect of the invention.

In an embodiment, the NK or T cell is in-vitro.
In an embodiment, the NK or T cell is autologous or allogeneic.
In an embodiment, the NK or T cell is from a primate.
In an embodiment, the NK or T cell is a human cell.

In a sixth aspect, the invention provides a pharmaceutical composition, comprising the chimeric antigen receptor according to the first aspect of the invention, the polynucleotide according to the second aspect of the invention, the vector according to the third aspect of the invention or the NK or T cell according to the fifth aspect of the invention, and a pharmaceutically acceptable carrier or excipient.

In an embodiment, the pharmaceutical composition is a liquid preparation.

In an embodiment, the pharmaceutical composition is an injection.

In an embodiment, the pharmaceutical composition comprises the NK or T cell at a concentration of $1\times10^5$-$1\times10^8$ cells/mL, preferably $1\times10^6$-$1\times10^7$ cells/mL.

In a seventh aspect, the invention provides a use of the chimeric antigen receptor according to the first aspect of the invention, the polynucleotide according to the second aspect of the invention, the vector according to the third aspect of the invention or the NK or T cell according to the fifth aspect of the invention in the preparation of a drug or a pharmaceutical preparation for preventing and/or treating cancers or tumors.

In an embodiment, the tumors are selected from hematologic malignancy, solid tumor or a combination thereof.

In an embodiment, the hematologic malignancy is selected from acute myeloid leukemia (AML), multiple myeloma (MM), chronic lymphocytic leukemia (CLL), acute lymphoblastic leukemia (ALL), diffuse large B cell lymphoma (DLBCL), non-Hodgkin lymphoma (NHL) or a combination thereof.

In an embodiment, the solid tumor is selected from gastric cancer, gastric cancer peritoneal metastasis, liver cancer, leukemia, renal tumor, lung cancer, small intestine cancer, bone cancer, prostate cancer, colorectal cancer, breast cancer, large intestine cancer, cervical cancer, ovarian cancer, lymphoma, nasopharyngeal carcinoma, adrenal tumor, bladder tumor, non-small cell lung cancer (NSCLC), glioma, endometrial cancer, mesothelioma, pancreatic cancer, multiple myeloma or a combination thereof.

In an eighth aspect, the present invention provides a method for preparing the NK or T cell according to the fifth aspect of the invention, comprising:

transducing the polynucleotide according to the second aspect of the invention or the vector according to the third aspect of the invention into an NK or T cell to obtain the NK or T cell.

In a ninth aspect, the present invention provides a method for treating a disease, comprising: administering a therapeutically effective amount of the chimeric antigen receptor according to the first aspect of the invention, the nucleic acid molecule according to the second aspect of the invention, the vector according to the third aspect of the invention, or the cell according to the fifth aspect of the invention, or the pharmaceutical composition according to the sixth aspect of the invention to a subject.

In an embodiment, the disease is a tumor.

It should be understood that various technical features described above and various technical features specifically described hereinafter (for example, in embodiments) of the present invention can be combined with each other to constitute a new or preferred technical solution that will not be described here due to space of this application.

BRIEF DESCRIPTION OF THE DRAWINGS

FIG. 10A shows schematic representation of CD19 hsCAR construct containing scFv regions and a selective domain in the linker sequence. FIGS. 10B-10C show evaluation of the level of humanization for VH and VL. FIGS. 10D-10E show measurement of the binding affinity of CD19 hsCAR with human CD19 extracellular domain by MST assay; where FMC63, murine-based CD19 CAR (CD19 mCAR) was used as a control and Kd of CD19 hsCAR was 6-fold smaller than that of CD19 mCAR. FIG. 10F shows results of SmAb (a selective domain-specific monoclonal antibody) re-stimulation on hsCAR-transduced T cells in comparison with CD19 hsCAR-engineered T cells without SmAb re-stimulation and CD19 mCAR-engineered T cells. FIG. 10G shows composition of subpopulations in the final products prepared under different conditions. FIGS. 10H-10J show results of SmAb re-stimulation on the proportion of CAR-positive T cells in CD19 hsCAR-T group in comparison with CD19 mCAR-T group with or without SmAb exposure, and CD19 hsCAR-T group without SmAb exposure.

FIG. 11A shows cytotoxicity of CD19 CAR-T cells prepared by different means, where the CD19 CAR-T cells were co-cultured with Raji, a human B lymphoblastoma cell line at different E/T ratios, and the cytotoxicity was measured by LDH release assay after a 12-h incubation. FIG. 11B shows release of cytokines during CAR-T mediated cytotoxicity (measured by ELISA assay). FIG. 11C shows results of SmAb re-stimulation on the composition of memory T cell subpopulations, where T cells isolated from PBMCs were transduced by CD19 mCAR or CD19 hsCAR; SmAb was added on day 6 post-transduction; and different memory T cell subpopulations were quantitated at indicated time points. FIG. 11D shows proliferation of central memory T cells, where the plot represented three independent assays. FIG. 11E shows compositions of different T cell subpopulations in the final product (Tte, terminally differentiated T cells; Tem, effector memory T cells; Tcm, central memory T cells). FIG. 11F shows effect of SmAb re-stimulation on multiple signaling pathways involved in the differentiation of memory T cells. FIG. 11G-11K show MFI values and histograms of each pathway based on flow cytometric results.

FIGS. 12A-12B show schematic representation of the animal study. NOD-SCID IL2Rγc$^{-/-}$ mice were i.v. injected with $1\times10^6$ Raji cells that constitutively express luciferase. After 3 days, mice were subjected to bioluminescence imaging, and grouped by different treatments. Mice were i.v. infused with $1\times10^6$ CD19 mCAR-T, CD19 hsCAR-T without SmAb re-stimulation, CD19 hsCAR-T re-stimulated by SmAb, CD19 hsCAR-T without intracellular domain (Stopper), T cell transduced by lentivirus expressing EGFP (Mock) or equivalent volume of PBS. Tumor progression was monitored by serial bioluminescence imaging at indicated time points. FIGS. 12C-12D show survival rates and median survival time of mice of different treatment groups. FIGS. 12E-12I show comparison of various cytokine levels in sera between different groups (measured by MSD assay).

FIGS. 13A-13B show counts and percentages of CD19 hsCAR-T cells in PB (measured by flow cytometry) before and after infusion in patients. FIGS. 13C-13D show copy numbers and the relative fold of expansion of CD19 hsCAR in genomic DNA (tested by qPCR) before and after infusion in the patients. FIGS. 13E-13L show various cytokine levels in the PB of patients at indicated time points after infusion (measured by MDS assay).

FIGS. 15A-15C show levels of Anti-CAR immunoglobulins, including IgA, IgG and IgM (detected by ELISA assay). Sera were collected from patients (n=5) who had been previously treated with CD19 mCAR-T cells at least once and from healthy donors (n=2). Purified his-tagged extracellular domains of CD19 mCAR or hsCAR were coated on ELISA plates, and incubated with the serum samples. HRP-labeled goat anti-human IgA, IgG and IgM antibodies were used for detection. FIGS. 15D-15F show effect of sera derived from patients with previous CD19 mCAR-T treatment(s) on cytotoxicity mediated by CD19 mCAR-T cells on Raji cell line.

FIG. 16A shows percentages of subpopulations among the CAR-positive T cells in the final product. FIGS. 16B-16C show subpopulations of memory cells in the CAR-positive T cells.

DETAILED DESCRIPTION OF EMBODIMENTS

Figure 1:
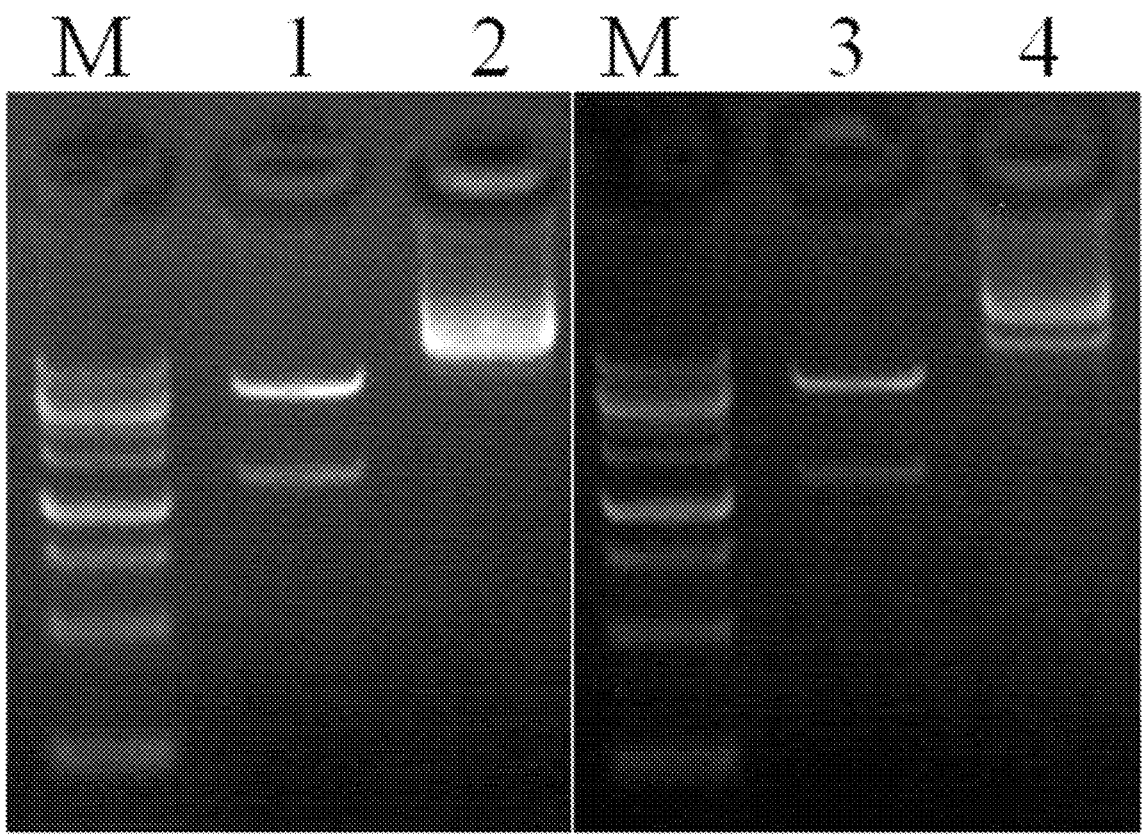
FIG. 1 shows the results of digestion of CD19-hsCAR (humanized selective CD19 CAR) and CD19-mCAR (murine-based CD19 CAR) lentiviral expression vectors, where M: DNA standard; 1: pLenti-CMV-CD19-hsCAR viral expression vector; 3: pLenti-CMV-CD19-mCAR viral expression vector; and 2, 4: pLenti-CMV empty vectors.

Through an extensive and in-depth research and screening, the inventors have surprisingly developed a CAR-encoding molecule with in vitro specific selectivity. By introducing a humanized selective domain, the CAR-positive effector cells after being infected can be efficiently sorted via a selective domain-specific antibody. In addition, exposure to this selective domain-specific antibody can selectively expand the transduced immune cells; therefore, the ratio of the CAR-positive cells in the final product is significantly increased, improving the efficiency of producing CAR gene-modified immune cell products. The present invention provides a more reliable technical support for further promotion and application of such products in clinical practice. In addition, the selective domain is combined with a variable region of anti-human CD19 single-chain antibody to produce the CAR. T cells or NK cells undergo a second activation when the CAR is stimulated by the selective domain-specific antibody, thereby significantly increasing the proliferation efficiency. The genetically engineered T or NK cells have better tumor-killing effects against CD19-positive cells and higher release levels of killing-associated factors. The present invention is completed on the basis of the above.

Terminology

Certain terms are defined in order to make the disclosure more apparent. As used herein, unless otherwise specified, each of the following terms should have the meaning given below. Other definitions are set forth throughout the application.

Term "about" refers to one or more particular values within a range of acceptable tolerances as determined by one of ordinary skill in the art, that partially depend on how they are measured or determined.

Term "administration" refers to physically introducing products of the present invention into a subject using any of a variety of methods and delivery systems known to those skilled in the art, comprising intravenous, intramuscular, subcutaneous, intraperitoneal and spinal administrations, and other parenteral administrations such as injection or infusion.

As used herein, term "antibody (Ab)" should comprise, but is not limited to, an immunoglobulin which specifically binds to an antigen and comprises at least two heavy (H) chains and two light (L) chains interlinked by disulfide bonds, or an antigen-binding portion. Each H chain comprises a heavy chain variable region (abbreviated herein as VH) and a heavy chain constant region. The heavy chain constant region comprises three constant domains CH1, CH2 and CH3. Each L chain comprises a light chain variable region (abbreviated herein as VL) and a light chain constant region. The light chain constant region comprises a constant domain CL. The VH and VL regions are further subdivided into hypervariable regions called complementarity determining regions (CDR), which are interspersed with more conserved regions called framework regions (FR). Each VH and VL comprise three CDRs and four FRs, FR1, CDR1, FR2, CDR2, FR3, CDR3, FR4 from the amino-terminal to the carboxyl-terminal. The variable regions of the heavy chain and the light chain comprise a binding domain interacting with an antigen.

As used herein, term "epitope", also known as antigenic determinant, refers to a specific chemical group determining the specificity of an antigen in an antigen molecule, which can be specifically recognized by an antibody. In the present invention, the selective domain has a specific epitope, which ensures that the selective domain can be recognized by an anti-selective domain antibody when it is free or present in the CAR.

Selective Domain

In the present invention, the chimeric antigen receptor comprises a selective domain having the following characteristics:

(a) it has a specific epitope, which is absent in $L_1$ and $L_2$;

(b) it can be recognized by an anti-selective domain antibody even when it is free or present in the CAR; and (c) it does not affect or substantially does not affect the binding of the CAR to the CAR-targeted antigen.

In an embodiment, Z is a polypeptide derived from human nucleoprotein La/SS-B. In an embodiment, Z is derived from an amino acid sequence of human nucleoprotein La/SS-B at positions 85-115, preferably at positions 95-104 of the C-terminal domain.

In an embodiment, the anti-selective domain antibody is an anti-human nucleoprotein La/SS-B polypeptide antibody.

In an embodiment, Z has an amino acid sequence as shown in positions 151-160 of SEQ ID NO.8, or positions 151-158 of SEQ ID NO.12, or positions 151-159 of SEQ ID NO.13.

Chimeric Antigen Receptor (CAR)

As used herein, a chimeric antigen receptor (CAR) comprises an extracellular domain, an optional hinge region, a transmembrane domain, and an intracellular domain. The extracellular domain optionally comprises a signal peptide and a target-specific binding element (also known as antigen-binding domain). The intracellular domain comprises a co-stimulatory molecule and a chain. The extracellular domain recognizes a specific antigen and then the signal is transduced though the intracellular domain upon the expression of the CAR in T cells, causing activation and proliferation of cells, cytolysis toxicity, and secretion of cytokines such as IL-2 and IFN-γ, and affecting tumor cells in growth arrest, death promotion or other ways, and leading to the reduction or elimination of the tumor burden of patients. The antigen-binding domain is preferably fused with one or more intracellular domains from the co-stimulatory molecule and the chain.

As used herein, "antigen-binding domain" and "single-chain antibody fragment" both refer to a fragment with antigen-binding activity selected from the group consisting of an Fab fragment, an Fab' fragment, an F(ab')2 fragment and a single Fv fragment. An Fv antibody comprises antibody heavy and light chain variable regions, but without constant region, and comprises a smallest antibody fragment having all antigen-binding sites. Generally, the Fv antibody further comprises a polypeptide linker between the VH and VL domains and is capable of forming a desired structure for antigen binding. The antigen-binding domain is typically a scFv (single-chain variable fragment). The size of scFv is generally ⅙ of that of an intact antibody. The single chain is preferably an amino acid sequence encoded by a nucleotide chain. In a preferred embodiment of the invention, the scFv comprises an antibody specifically recognizing an antigen highly expressed by a tumor, preferably a single-chain antibody. In an embodiment, the scFv has a structure of $F_1$-$L_1$-Z-$L_2$-$F_2$. In another embodiment, the scFv has a structure of $F_1$-Z-$F_2$.

In an embodiment, the CAR has a structure of $F_0$-$F_1$-$L_1$-Z-$L_2$-$F_2$-H-TM-C-CD3. Preferably, the CAR has a sequence shown as SEQ ID NO.8 in which a selective domain is shown in bold.

```
                                                 (SEQ ID NO: 8)
MALPVTALLLPLALLLHAARPQVQLQQSGAELVRPGSSVKISCKASGYAF

SSYWMNWVKQRPGQGLEWIGQIWPGDGDTNYNGKFKGKATLTADESSSTA

YMQLSSLASEDSAVYFCARRETTTVGRYYYAMDYWGQGTTVTVSSGGGGS

KPLPEVTDEYGGGGSDIQLTQSPASLAVSLGQRATISCKASQSVDYDGDS

YLNWYQQIPGQPPKLLIYDASNLVSGIPPRFSGSGSGTDFTLNIHPVEKV

DAATYHCQSTEDPWTFGGGTKLEIKTTTPAPRPPTPAPTIASQPLSLRPE

ACRPAAGGAVHTRGLDFACDIYIWAPLAGTCGVLLLSLVITLYCKRGRKK

LLYIFKQPFMRPVQTTQEEDGCSCRFPEEEEGGCELRVKFSRSADAPAYKQ

GQNQLYNELNLGRREEYDVLDKRRGRDPEMGGKPRRKNPQEGLYNELQKD

KMAEAYSEIGMKGERRRGKGHDGLYQGLSTATKDTYDALHMQALPPR
```

In SEQ ID NO.8, the signal peptide $F_0$ is shown in positions 1-21; the single-chain antibody heavy chain variable region $F_1$ is shown in positions 22-145; the linker peptide $L_1$ is shown in positions 146-150; the selective domain Z is shown in positions 151-160; the linker peptide $L_2$ is shown in positions 161-165; the single-chain antibody light chain variable region $F_2$ is shown in positions 166-276; the hinge region and transmembrane region H-TM is shown in positions 277-345; and the intracellular signal transduction and activation domain C-CD3ζ is shown in positions 346-499.

In an embodiment, the CAR has a sequence shown as SEQ ID NO.12 in which a selective domain is shown in bold.

```
                                                (SEQ ID NO: 12)
MALPVTALLLPLALLLHAARPQVQLQQSGAELVRPGSSVKISCKASGYAF

SSYWMNWVKQRPGQGLEWIGQIWPGDGDTNYNGKFKGKATLTADESSSTA

YMQLSSLASEDSAVYFCARRETTTVGRYYYAMDYWGQGTTVTVSSGGGGS

WSHPQFEKGGGGSDIQLTQSPASLAVSLGQRATISCKASQSVDYDGDSYL

NWYQQIPGQPPKLLIYDASNLVSGIPPRFSGSGSGTDFTLNIHPVEKVDA

ATYHCQQSTEDPWTFGGGTKLEIKTTTPAPRPPTPAPTIASQPLSLRPEA

CRPAAGGAVHTRGLDFACDIYIWAPLAGTCGVLLLSLVITLYCKRGRKKL

LYIFKQPFMRPVQTTQEEDGCSCRFPEEEEGGCELRVKFSRSADAPAYKQ

GQNQLYNELNLGRREEYDVLDKRRGRDPEMGGKPRRKNPQEGLYNELQKD

KMAEAYSEIGMKGERRRGKGHDGLYQGLSTATKDTYDALHMQALPPR
```

In SEQ ID NO.12, the signal peptide $F_0$ is shown in positions 1-21; the single-chain antibody heavy chain variable region $F_1$ is shown in positions 22-145; the linker peptide $L_1$ is shown in positions 146-150; the selective domain Z is shown in positions 151-158; the linker peptide $L_2$ is shown in positions 159-163; the single-chain antibody light chain variable region $F_2$ is shown in positions 164-274; the hinge region and transmembrane region H-TM is shown in positions 275-343; and the intracellular signal transduction and activation domain C-CD3ζ is shown in positions 344-497.

In an embodiment, the CAR has a sequence shown as SEQ ID NO.13 in which a selective domain is shown in bold.

```
                                                (SEQ ID NO: 13)
MALPVTALLLPLALLLHAARPQVQLQQSGAELVRPGSSVKISCKASGYAF

SSYWMNWVKQRPGQGLEWIGQIWPGDGDTNYNGKFKGKATLTADESSSTA

YMQLSSLASEDSAVYFCARRETTTVGRYYYAMDYWGQGTTVTVSSGGGGS

NWSHPQFEKGGGGSDIQLTQSPASLAVSLGQRATISCKASQSVDYDGDSY

LNWYQQIPGQPPKLLIYDASNLVSGIPPRFSGSGSGTDFTLNIHPVEKVD

AATYHCQQSTEDPWTFGGGTKLEIKTTTPAPRPPTPAPTIASQPLSLRPE

ACRPAAGGAVHTRGLDFACDIYIWAPLAGTCGVLLLSLVITLYCKRGRKK

LLYIFKQPFMRPVQTTQEEDGCSCRFPEEEEGGCELRVKFSRSADAPAYK

QGQNQLYNELNLGRREEYDVLDKRRGRDPEMGGKPRRKNPQEGLYNELQK

DKMAEAYSEIGMKGERRRGKGHDGLYQGLSTATKDTYDALHMQALPPR
```

In SEQ ID NO.13, the signal peptide $F_0$ is shown in positions 1-21; the single-chain antibody heavy chain variable region $F_1$ is shown in positions 22-145; the linker peptide $L_1$ is shown in positions 146-150; the selective domain Z is shown in positions 151-159; the linker peptide $L_2$ is shown in positions 160-164; the single-chain antibody light chain variable region $F_2$ is shown in positions 165-275; the hinge region and transmembrane region H-TM is shown in positions 276-344; and the intracellular signal transduction and activation domain C-CD3ζ is shown in positions 345-498.

Coding Sequence

The present invention further relates to a polynucleotide encoding the chimeric antigen receptor according to the invention.

The polynucleotide may be in the form of DNA or RNA. The DNA may be a coding or non-coding strand. The coding region sequence of a mature polypeptide may be the same as or a degenerate variant of the sequence encoding the polypeptide shown as SEQ ID NO.8, 12 or 13. As used herein, "degenerate variant" refers to a nucleic acid sequence, which encodes a polypeptide comprising the polypeptide shown as SEQ ID NO.8, 12 or 13, but differs from such polynucleotide in the sequence of the corresponding coding region.

In a preferred embodiment, the polynucleotide has a sequence shown as SEQ ID NO.7.

Full-length sequence of the nucleotide or a fragment thereof is usually obtained using PCR amplification, recombination or a synthetic method. Currently, a DNA sequence encoding the polypeptide (or a fragment or a derivative thereof) can be obtained completely by chemical synthesis. Then the DNA sequence can be introduced into various DNA molecules (or vectors) and cells known in the art.

The invention also relates to a vector comprising the polynucleotide of the invention, and a host cell produced using the vector or the polypeptide coding sequence of the invention by genetic engineering. The polynucleotide, vector or host cell may be isolated.

As used herein, "isolated" means that a substance is separated from its original environment (the original environment is a natural environment in the case of a natural-occurring substance). For example, polynucleotides and polypeptides in a natural state in living cells are not isolated or purified, but the same polynucleotides or polypeptides separated from other substances present in the natural form is isolated or purified.

The polynucleotide of the invention may be a DNA or RNA. The DNA comprises cDNA, genomic DNA and synthetic DNA. The DNA may be single-stranded or double-stranded. In addition, the DNA may be a coding strand or a non-coding strand.

The invention also relates to a variant of the polynucleotide, which encodes a protein fragment, an analog or a derivative having the same amino acid sequence as that encoded by the polynucleotide of the present invention. The variant of this polynucleotide may be a natural-occurring allelic variant or a variant occurred non-naturally. These nucleotide variants comprise variants resulted from substitution, deletion and insertion. It is known that the allelic variant is an alternative form of polynucleotide and formed via a substitution, deletion or insertion of one or more nucleotides, but such modifications substantially does not alter the function of the polynucleotide in encoding the fusion protein of the invention.

Full-length nucleotide sequence of the polypeptide or a fragment thereof is usually obtained by PCR amplification, recombination or a synthetic method. For PCR amplification, a primer is designed according to nucleotide sequences as disclosed, particularly open reading frame sequences, and a commercially available cDNA library or a cDNA library prepared by conventional methods known to those skilled in the art is employed as a template for amplification to obtain the relevant sequence. When the sequence is relatively long, it requires two or more PCR amplification, and the amplified fragments are assembled together in a correct order.

In an embodiment, a polynucleotide sequence encoding the chimeric antigen receptor is shown as SEQ ID NO.7.

```
                                              (SEQ ID NO. 7)
ATGGCTCTGCCAGTGACAGCTCTGCTGCTGCCTCTGGCTCTGCTGCTGCA
CGCAGCTAGACCCCAGGTGCAGCTGCA

GCAGTCAGGAGCAGAACTCGTGAGACCAGGCAGCAGCGTGAAGATCTCTT
GCAAGGCCAGCGGCTACGCCTTCTCTA

GCTATTGGATGAATTGGGTGAAGCAGCGGCCAGGACAGGGACTGGAGTG
GATTGGACAGATTTGGCCCGGCGACGGC

GATACCAACTACAACGGCAAGTTCAAGGGCAAGGCCACCCTGACAGCCG
ACGAGTCTAGCAGCACAGCCTACATGCA

GCTGAGCTCTCTGGCCAGCGAGGATAGCGCCGTGTACTTTTGCGCCAGAA
GGGAGACCACAACAGTGGGCCGGTACT

ACTACGCCATGGACTATTGGGGCCAGGGCACAACCGTGACAGTGTCTAGC
GGAGGAGGCGGCTCTAAGCCTCTGCCA

GAAGTGACAGACGAGTACGGCGGAGGAGGAAGCGACATCCAGCTGACCC
AGAGCCCAGCTTCTCTGGCAGTGTCTCT

GGGACAGAGGGCTACCATCTCTTGCAAGGCCAGCCAGAGCGTGGATTACG
ACGGCGACAGCTACCTGAATTGGTATC

AGCAGATCCCCGGCCAGCCTCCTAAGCTGCTGATCTACGACGCCTCCAAC
CTGGTGTCCGGCATCCCTCCCAGATTC

AGCGGAAGCGGCAGCGGCACAGACTTCACCCTGAACATCCACCCCGTGGA
GAAGGTGGACGCCGCCACATACCATTG

CCAGCAGAGCACAGAGGACCCCTGGACCTTTGGCGGCGGAACAAAGCTG
GAGATCAAGACAACCACCCCAGCCCCTA

GACCTCCTACACCAGCCCCTACAATCGCCTCTCAGCCTCTGAGCCTGAGG
CCAGAAGCTTGTAGACCCGCAGCAGGA

GGAGCAGTGCATACAAGGGGCCTGGACTTCGCTTGCGACATCTACATTTG
GGCCCCTCTGGCAGGAACTTGCGGAGT

GCTGCTGCTGTCTCTGGTCATCACCCTGTATTGCAAGCGGGGCCGGAAGA
AGCTGCTGTACATCTTCAAGCAGCCCT

TCATGCGGCCAGTGCAGACAACACAGGAGGAGGACGGTTGCAGCTGCAG
ATTCCCAGAGGAGGAGGAAGGCGGCTGC

GAGCTGAGAGTGAAGTTCAGCAGGAGCGCCGACGCTCCAGCCTATAAAC
AGGGACAGAACCAGCTGTACAACGAGCT

GAACCTGGGCAGAAGAGAGGAGTACGACGTGCTGGACAAGAGGAGAGGC
AGAGACCCAGAGATGGGCGGCAAGCCTA

GAAGGAAGAACCCCCAGGAGGGCCTGTACAACGAGCTGCAGAAGGACAA
GATGGCCGAGGCTTACAGCGAGATCGGC

ATGAAGGGCGAGAGGAGAAGAGGCAAAGGCCACGACGGACTGTATCAGG
GACTGAGCACAGCCACCAAGGACACCTA

CGACGCTCTGCACATGCAGGCTCTGCCTCCTAGATAA.
```

In another embodiment, a polynucleotide sequence encoding signal peptide F₀ is shown as SEQ ID NO.1.

```
                                              (SEQ ID NO. 1)
ATGGCGCTGCCGGTGACCGCGCTGCTGCTGCCGCTGGCGCTGCTGCTG
CATGCGGCGCGTCCG
```

In another embodiment, a polynucleotide sequence encoding hinge region and transmembrane region H-TM is shown as SEQ ID NO.2.

```
                                              (SEQ ID NO. 2)
ACCACCACCCCGGCGCCGCGTCCGCCGACCCCGGCGCCGACCATTGCGAG

CCAGCCGCTGAGCCTGCGTCCGGAAGCGTGCCGTCCGGCGGCGGGCGGCG

CGGTGCATACCCGTGGCCTGGATTTTGCGTGCGATATTTATATTTGGGCGC

CGCTGGCGGGCACCTGCGGCGTGCTGCTGCTGAGCCTGGTGATTACCCTGT

ATTGC.
```

In another embodiment, a polynucleotide sequence encoding intracellular signal transduction and activation domain C-CD3ζ is shown as SEQ ID NO.3.

```
                                              (SEQ ID NO. 3)
AAACGTGGCCGTAAAAAACTGCTGTATATTTTTAAACAGCCGTTTATGCG

TCCGGTGCAGACCACCCAGGAAGAAGATGGCTGCAGCTGCCGTTTTCCGG

AAGAAGAAGGCGGCTGCGAACTGCGTGTGAAATTTAGCCGTAGCGCG

GATGCGCCGGCGTATAAACAGGGCCAGAACCAGCTGTATAACGAACTGAA

CCTGGGCCGTCGTGAAGAATATGATGTGCTGGATAAACGTCGTGGCCGTG

ATCCGGAAATGGGCGGCAAACCGCGTCGTAAAAACCCGCAGGAAGGCCTG

TATAACGAACTGCAGAAAGATAAAATGGCGGAAGCGTATAGCGAAATTGG

CATGAAAGGCGAACGTCGTCGTGGCAAAGGCCATGATGGCCTGTATCAGG
```

-continued
GCCTGAGCACCGCGACCAAAGATACCTATGATGCGCTGCATATGCAGGCG

CTGCCGCCGCGT.

In another embodiment, a polynucleotide sequence encoding selective domain Z is shown as SEQ ID NO.4.

(SEQ ID NO. 4)
AAACCGCTGCCGGAAGTGACCGATGAATAT.

In another embodiment, a polynucleotide sequence encoding selective domain Z is shown as SEQ ID NO.14.

(SEQ ID NO. 14)
TGGAGCCATCCGCAGTTTGAAAAA.

In another embodiment, a polynucleotide sequence encoding $L_1$ or $L_2$ is shown as SEQ ID NO.11.

(SEQ ID NO. 11)
GGCGGCGGCGGCAGC.

In another embodiment, a polynucleotide sequence encoding $F_1$ is shown as SEQ ID NO.5.

(SEQ ID NO. 5)
CAGGTGCAGCTGCAGCAGAGCGGCGCGGAACTGGTGCGTCCGGGCAGCA

GCGTGAAAATTAGCTGCAAAGCGAGCGGCTATGCGTTTAGCAGCTATTGG

ATGAACTGGGTGAAACAGCGTCCGGGCCAGGGCCTGGAATGGATTGGCCA

GATTTGGCCGGGCGATGGCGATACCAACTATAACGGCAAATTTAAAGGCA

AAGCGACCCTGACCGCGGATGAAAGCAGCAGCACCGCGTATATGCAGCTG

AGCAGCCTGGCGAGCGAAGATAGCGCGGTGTATTTTTGCGCGCGTCGTGA

AACCACCACCGTGGGCCGTTATTATTATGCGATGGATTATTGGGGCCAGG

GCACCACCGTGACCGTGAGCAGC.

In another embodiment, a polynucleotide sequence encoding $F_2$ is shown as SEQ ID NO.6.

(SEQ ID NO. 6)
GATATTCAGCTGACCCAGAGCCCGGCGAGCCTGGCGGTGAGCCTGGGCCA

GCGTGCGACCATTAGCTGCAAAGCGAGCCAGAGCGTGGATTATGATGGCG

ATAGCTATCTGAACTGGTATCAGCAGATTCCGGGCCAGCCGCCGAAACTG

CTGATTTATGATGCGAGCAACCTGGTGAGCGGCATTCCGCCGCGTTTTAG

CGGCAGCGGCAGCGGCACCGATTTTACCCTGAACATTCATCCGGTGGAAA

AAGTGGATGCGGCGACCTATCATTGCCAGCAGAGCACCGAAGATCCGTGG

ACCTTTGGCGGCGGCACCAAACTGGAAATTAAA.

When the relevant sequences have been obtained, recombination is used to produce the relevant sequences in large quantities. Usually, the sequences are cloned into a vector, and then the vector is transformed into a cell. Subsequently, the relevant sequences are isolated from the proliferated host cells using a conventional method.

In addition, the relevant sequences may be synthesized, particularly for a fragment with a relatively short length. In general, a fragment with a long sequence can be obtained by synthesizing a plurality of small fragments and then assembling them together.

A method of amplifying DNA/RNA using PCR is preferably used to obtain the gene of the invention. The primer for PCR can be appropriately selected according to the sequence information disclosed herein, and can be synthesized using a conventional method. The amplified DNA/RNA fragments can be isolated and purified using conventional methods such as gel electrophoresis.

The invention also relates to a vector comprising the polynucleotide, and a host cell produced using the vector or the protein coding sequence of the invention by genetic engineering, and a method for expressing the CARs on the T or NK cells via recombination.

T or NK cells expressing the CARs can be obtained using the polynucleotide sequence of the invention by the conventional DNA recombination technique. Generally, the method for preparing the T or NK cells comprises a step of: transducing the polynucleotide according to the second aspect of the invention or the vector according to the third aspect of the invention into T or NK cells, thereby obtaining the T or NK cells.

An expression vector comprising a DNA sequence encoding the enzyme of the invention and suitable transcriptional/translational control signals can be constructed using methods known to those skilled in the art. These methods comprise in-vitro DNA combination, DNA synthesis and in-vivo recombination techniques. The DNA sequence can be effectively linked to an appropriate promoter on the expression vector to guide mRNA synthesis. The expression vector further comprises a ribosome binding site for translation initiation and a transcription terminator.

In addition, the expression vector preferably comprises one or more selectable marker genes to provide phenotypic traits for selecting the host cells for transformation, such as dihydrofolate reductase, neomycin resistance and green fluorescent protein (GFP) for eukaryotic cell culture, or tetracycline or ampicillin resistance for *Escherichia coli*.

A vector comprising the above appropriate DNA sequence and the appropriate promoter or control sequence can be used to transform an appropriate host cell to express the protein.

The host cell is a prokaryotic cell such as a bacterial cell; or a lower eukaryotic cell such as a yeast cell; or a higher eukaryotic cell such as a mammalian cell. Representative host cells comprise bacterial cells such as *Escherichia coli, Bacillus subtilis* and *Streptomyces* cells; fungal cells such as *Pichia pastoris* and *Saccharomyces cerevisiae* cells; plant cells; insect cells such as *Drosophila* S2 or Sf9 cells; and animal cells such as CHO, NS0, COS7, and 293 Cells. In a preferred embodiment of the invention, T or NK cells are selected as the host cells.

Transformation of the host cells with recombinant DNA can be carried out using conventional techniques known to those skilled in the art. When the host is a prokaryote such as *E. coli*, competent cells capable of absorbing DNA upon treatment by $CaCl_2$ can be harvested after exponential growth phase, which is known in the art. Another method uses $MgCl_2$. If necessary, the transformation may be carried out via electroporation. For a eukaryotic cell, methods for DNA transfection, including calcium phosphate co-precipitation and conventional mechanical treatments such as microinjection, electroporation and liposome encapsulation, may be used.

The obtained transformant can be cultured using a conventional method to express the protein encoded by the gene of the invention. According to the host cell, the culture media may be selected from various conventional media. The culture is carried out under conditions suitable for the growth of the host cells. After the host cell grows to an appropriate cell density, the selected promoter is induced by a suitable method (such as temperature conversion or chemical induction), and the cells are further cultured for a period of time.

Proteins in the above methods can be expressed inside the cells, or on the cell membrane, or secreted outside the cells. If necessary, the proteins can be isolated and purified by various known separation methods according to their physical, chemical and other properties. Examples of these methods include, but are not limited to, conventional renaturation treatment, treatment with a protein precipitant (salting out), centrifugation, osmotic disruption, super treatment, ultracentrifugation, molecular sieve chromatography (gel filtration), adsorption chromatography, ion exchange chromatography, high performance liquid chromatography (HPLC), or other liquid chromatography techniques or a combination thereof.

Vector

The invention also provides a vector comprising a polynucleotide encoding the CAR of the invention. Vectors derived from retroviruses such as lentiviruses are suitable as tools to achieve long-term gene transfer because they allow long-term, stable integration of the transgene and proliferation in daughter cells. Lentiviral vectors have the advantages over vectors derived from oncogenic retroviruses such as murine leukemia viruses, because lentiviral vectors can transduce non-proliferation cells, such as hepatocytes. They further have the advantage of low immunogenicity.

Briefly, the expression cassette or nucleic acid sequence of the invention is operably linked to a promoter and incorporated into an expression vector. This vector is suitable for replication and integration in eukaryotic cells. A typical cloning vector comprises a transcriptional and translational terminator, an initial sequence and a promoter which can be used to regulate expression of a desired nucleic acid sequence.

The expression construct of the invention may be used for nucleic acid immunization and gene therapy using a standard gene delivery protocol. The gene delivery technology has been known in the art. See, for example, U.S. Pat. Nos. 5,399,346, 5,580,859 and 5,589,466, which are incorporated herein by reference. In another embodiment, the invention provides a vector for gene therapy.

The expression cassette or nucleic acid sequence can be cloned into many types of vectors. For example, the expression cassette or nucleic acid sequence can be cloned into vectors including, but not limited to: plasmids, phagemids, phage derivatives, animal viruses, and cosmids. Specific vectors of interest comprise expression vectors, replication vectors, probe-producing vectors, and sequencing vectors.

Further, the expression vector can be introduced to the cells in the form of a viral vector. Viral vector known in the art are described, for example, in Sambrook et al. (2001, Molecular Cloning: A Laboratory Manual, Cold Spring Harbor Laboratory, New York) and other virology and molecular biology manuals. Viruses useful for vectors include, but are not limited to retroviruses, adenoviruses, adeno-associated viruses, herpesviruses, and lentiviruses. Generally, an appropriate vector comprises a replication origin, a promoter sequence, a convenient restriction enzyme site, and one or more selectable markers functioning in at least one organism (e.g., WO 01/96584; WO 01/29058; and U.S. Pat. No. 6,326,193)

Many virus-based systems have been developed for transferring genes into mammalian cells. For example, retroviruses provide a convenient platform for gene delivery systems. The selected gene can be inserted into a vector and packaged into retroviral particles using techniques known in the art. The recombinant virus can then be isolated and delivered to in-vivo or ex-vivo subject cells. Many retroviral systems are known in the art. In some embodiments, an adenoviral vector is used, and many adenoviral vectors are known in the art. In an embodiment, a lentiviral vector is used.

Additional promoter elements such as enhancers, regulate the frequency of transcriptional initiation. Typically, these are located in the 30-110 bp region by upstream of the start site, although a number of promoters have recently been shown to contain functional elements downstream of the start site. The spacing between promoter elements generally is flexible, so that promoter function is preserved when elements are inverted or moved relative to one another. In the thymidine kinase (tk) promoter, the spacing between promoter elements can be increased to 50 by apart before activity begins to decline. Depending on the promoter, it appears that individual elements can function either cooperatively or independently to activate transcription.

An example of an appropriate promoter is a cytomegalovirus (CMV) immediate-early promoter. The promoter is a strong constitutive promoter sequence capable of driving high level expression of any polynucleotide sequence operably linked thereto. Another example of an appropriate promoter is elongation factor-1 α (EF-1 α). However, other constitutive promoter may also be used, including but not limited to simian virus 40 (SV40) early promoter, mouse mammary tumor virus (MMTV) promoter, human immunodeficiency virus (HIV) long terminal repeat (LTR) promoter, MoMuLV promoter, avian leukemia virus promoter, Epstein-Barr virus immediate-early promoter, rous sarcoma virus promoter. Human gene promoter may be used, including but not limited to actin promoter, myosin promoter, heme promoter and creatine kinase promoter. Further, the invention should not be limited to the use of constitutive promoters, and inducible promoters are also considered as a part of the invention. The use of an inducible promoter provides a molecular switch capable of opening expression of a polynucleotide sequence operably linked to the inducible promoter when such expression is desired, or closing expression when such expression is undesirable. Examples of inducible promoters include, but are not limited to metallothionein promoters, glucocorticoid promoters, progesterone promoters and tetracycline promoters.

The expression vector introduced into the cells may also comprise either or both of a selectable marker gene and a reporter gene to facilitate identification and selection cells for expression from cell populations sought to be transfected or infected with a viral vector. In other aspects, selectable markers can be carried on a single piece of DNA and used for co-transfection. Both of the selectable marker and the reporter gene may be flanked with appropriate regulatory sequences to enable expression in the host cell. Useful selectable markers include, for example, antibiotic resistance genes such as neo.

Reporter genes are used to identify potentially transfected cells and to evaluate the functionality of regulatory sequences. Generally, the reporter gene is a gene that is not present in or expressed by the recipient organism or tissue, and encodes a polypeptide whose expression is clearly indicated by some readily detectable properties such as enzymatic activity. After DNA has been introduced into the recipient cells, the expression of the reporter gene is determined at an appropriate time. Appropriate reporter genes include genes encoding luciferase, beta-galactosidase, chloramphenicol acetyltransferase, secreted alkaline phosphatase and green fluorescent protein genes (reported in, for example Ui-Tei et al., 2000 FEBS Letters 479: 79-82). Suitable expression systems are well known and can be prepared using known techniques or may be commercially available. Generally, a construct with at least 5 flanking regions expressed by a reporter gene showing the highest expression level is identified as a promoter. Such a promoter can be linked to a reporter gene and used to evaluate the ability of agents to regulate promoter-driven transcription.

Methods of introducing and expressing genes into cells are known in the art. In the context of expression vector, the vector can be readily introduced a host cell by any method in the art, and the host cell may be a mammalian (e.g., human T cell), bacterial, yeast or insect cell. For example, the expression vector can be transformed into the host cell by physical, chemical or biological means.

Physical methods for introducing a polynucleotide into a host cell include calcium phosphate precipitation, lipofection, particle bombardment, microinjection, and electroporation. Methods of producing cell comprising a vector and/or an exogenous nucleic acid are known in the art, for example, see Sambrook et al. (2001, Molecular Cloning: A Laboratory Manual, Cold Spring Harbor Laboratory, New York). A preferred method of introducing a polynucleotide into a host cell is calcium phosphate transfection.

Biological methods for introducing a polynucleotide into a host cell comprise the use of DNA and RNA vectors. Viral vectors, particularly retroviral vectors, have become the most widely used method for inserting genes into mammals, e.g., human cells. Other viral vectors may be derived from lentiviruses, poxviruses, herpes simplex viruses I, adenoviruses, adeno-associated viruses, etc. See, for example, U.S. Pat. Nos. 5,350,674 and 5,585,362.

Chemical means for introducing a polynucleotide into a host cell comprise colloidal dispersion systems such as macromolecular complexes, nanocapsules, microspheres, beads; and lipid-based systems including oil-in-water emulsions, micelles, mixed micelles, and liposomes. An exemplary colloidal system used as an in-vitro and in-vivo delivery vehicle is liposome (e.g., an artificial membranous capsule).

In the case of non-viral delivery system, an exemplary delivery tool is liposome. It is considered to use a lipid formulation to introduce the nucleic acid into a host cell (in vitro, ex vivo or in vivo). In another aspect, the nucleic acid may be associated with a lipid. Nucleic acid associated with liposome may be encapsulated into the aqueous interior of the liposome, interspersed in the lipid bilayer of the liposome, attached to the liposome via a linker molecule associated with both of liposome and oligonucleotide, trapped into the liposome, complexed with the liposome, dispersed in a lipid-containing solution, mixed with the lipids, combined with the lipids as a suspension contained in the lipids, contained in micelles or complexed with micelles, or may be associated with lipid in other ways. The lipid, lipid/DNA or lipid/expression vector associated with the composition is not limited to any specific structures in solution. For example, they may be present in bilayer structure as a micelle or with a "collapsed" structure. They may also be simply dispersed in solution to form possible aggregates of varying sizes or shapes. Lipids are fatty materials which may be natural-occurring or synthetic lipids. For example, the lipids comprise fat droplets which naturally occur in the cytoplasm and in such compounds including long-chain aliphatic hydrocarbons or their derivatives such as fatty acids, alcohols, amines, amino alcohols, and aldehydes.

In a preferred embodiment of the invention, the vector is a lentiviral vector.

Pharmaceutical Composition

The invention provides a pharmaceutical composition, in particularly, as described in the sixth aspect of the invention. In an embodiment, the pharmaceutical composition is a liquid preparation. Preferably, the pharmaceutical composition is an injection. Preferably, the pharmaceutical composition comprises the CAR-T cells at a concentration of $1\times10^3$-$1\times10^8$ cells/mL, more preferably $1\times10^4$-$1\times10^7$ cells/mL.

In an embodiment, the pharmaceutical composition may comprise a buffer such as neutral buffered saline and sulfate buffered saline, etc.; a carbohydrate such as glucose, mannose, sucrose or dextran, and mannitol; a protein; a polypeptide or an amino acid such as glycine; an antioxidant; a chelating agent such as EDTA or glutathione; an adjuvant such as aluminum hydroxide; and a preservative. The preparation of the invention is preferably formulated for intravenous administration.

Therapeutic Application

The invention comprises a therapeutic application of cells (e.g., T or NK cells) transduced with a lentiviral vector (LV) comprising the polynucleotide of the invention.

In an embodiment, the invention comprises a type of cell therapy where autologous T cells of a patient (or heterologous donors) are separated, activated and genetically modified to produce CAR-T cells, which are then injected into the same patient. In this way, the occurrence rate of graft-versus-host disease is very low, and an antigen is recognized by T cells without MHC restriction. In addition, a CAR-T is able to treat all cancers expressing the antigen. Unlike antibody therapy, CAR-T cells are able to replicate in vivo, producing a long-term persistence that leads to sustained tumor control.

In an embodiment, the CAR-T cell of the invention may undergo stable in-vivo T cell expansion and hold for an extended time. Further, the CAR-mediated immune response may be part of adoptive immunotherapy, in which CAR-modified T cells induce an immune response specific for the antigen binding domain in the CAR. For example, anti-CD19 CAR-T cells cause a specific immune response of cells against expressing CD19.

Treatable cancers include tumors that have not been or substantially have not been vascularized tumors, and vascularized tumors. Cancers may include non-solid tumors (such as hematological tumors, e.g., leukemias and lymphomas) or solid tumors. Cancers treated with the CAR of the invention include, but are not limited to blastomas, sarcomas and some leukemia or lymphoid benign and malignant tumors, and other malignant tumors such as sarcomas, carcinomas and melanomas. Adult and childhood tumors/cancers are also included.

Hematological cancer is a cancer of blood or bone marrow. Examples of hematological (or hematogenous) cancers include leukemias, including acute leukemias (such as acute lymphocytic leukemia, acute myeloid leukemia, acute myelogenous leukemia, and myeloblastic, promyelocytic, myelomonocytic, monoblastic and erythroblastic leukemias), and chronic leukemias (such as chronic myeloid (granulocytic) leukemia, chronic myelogenous leukemia, chronic lymphocytic leukemia), polycythemia vera, lymphoma, Hodgkin's disease, non-Hodgkin's lymphoma (painless and high-grade forms), multiple myeloma, Waldenstrom's macroglobulinemia, heavy chain disease, myelodysplastic syndrome, hairy cell leukemia, and myelodysplasia.

A solid tumor is an abnormal mass of tissue that usually does not contain a cyst or fluid area. The solid tumor may be benign or malignant. Different types of solid tumors are named after the cells types forming them (such as sarcomas, carcinomas, and lymphomas). Examples of solid tumors such as sarcomas and carcinomas include fibrosarcomas, myxosarcomas, liposarcoma mesotheliomas, lymphoid malignancies, pancreatic cancer and ovarian cancer.

The CAR-T or CAR-NK cell of the invention may also be used as vaccine types for ex vivo immunity and/or in vivo therapy in mammals. Preferably, the mammal is a human.

For ex vivo immunity, at least one of: i) cell expansion; ii) introduction of the polynucleotide or vector of the invention into the cells; and/or iii) cryopreservation of the cells occurs in vitro, prior to administration of the cells into the mammal.

Ex-vivo procedures are well known in the art and are described more specifically below. Briefly, cells are isolated from a mammal, preferably, a human, and genetically modified (i.e., transduced or transfected in vitro) with a vector comprising the polynucleotide of the invention. The CAR-T or CAR-NK cell of the invention can be administered to a mammalian recipient to provide a therapeutic benefit. Mammalian recipient may be a human, and the CAR-modified cell may be autologous to the recipient. Alternatively, the cells may be allogeneic, syngeneic or xenogeneic relative to the recipient.

In addition to the use of a cell-based vaccine for ex vivo immunization, the invention also provides a composition and a method for in vivo immunization to elicit an immune response against antigens in a patient.

Generally, cells activated and expanded as described herein can be used to treat and prevent diseases developed in an individual without an immune response. Therefore, the invention provides a method of treating cancer, comprising administrating the CAR-modified T or NK cell of the invention at a therapeutically effective amount to a subject.

The CAR-T cells or CAR-NK cell of the invention may be administered alone or as a pharmaceutical composition in combination with a diluent and/or other components such as IL-2, IL-17 or other cytokines or cell populations. Briefly, the pharmaceutical composition of the invention may comprise a population of target cells as described herein in combination with one or more pharmaceutically or physiologically acceptable carriers, diluents or excipients.

The pharmaceutical composition of the present invention can be administered in a form suitable for the disease to be treated (or prevented). The amount and frequency of administration will be determined by factors such as the conditions of the patient, and the type and severity of the patient's disease, although appropriate dosages may be determined by clinical trials.

When referring to "immunologically effective amount", "anti-tumor effective amount", "tumor-suppressing effective amount" or "therapeutic amount", the precise amount of the composition of the invention to be administered may be determined by the physician, taking into account age, weight, tumor size, degree of infection or metastasis of a patient (subject) and individual differences of the conditions. It may generally be indicated that a pharmaceutical composition comprising the T or NK cells described herein may be administered at a dosage of $10^4$-$10^9$ cells/kg, preferably at a dosage of $10^5$-$10^6$ cells/kg (including all integers within such range). A T or NK cell composition may be administered several times at such dosage. Cells may be administered using injection techniques well known in immunotherapy (see, for example, Rosenberg et al., New Eng. J. of Med. 319: 1676, 1988). The optimal dosage and treatment regimen for a particular case can be readily determined by a person skilled in the medical arts by monitoring the signs of disease, thus adjusting the treatment.

Administration of the subject composition can be carried out in any convenient manner, including by spraying, injecting, swallowing, infusion, implantation or transplantation. The composition described herein may be administered to a patient subcutaneously, intradermally, intratumorally, intranodally, intraspinally, intramuscularly, by intravenous (i.v.) injection or intraperitoneally. In an embodiment, the T or NK cell composition of the invention is administered to a patient via intradermal or subcutaneous injection. In another embodiment, the T or NK cell composition of the invention is preferably administered via intravenous (i.v.) injection. The T or NK cell composition may be injected directly into tumors, lymph nodes or infected sites.

In some embodiments, cells activated and expanded using the methods described herein or other methods known in the art to expand T or NK cells to a therapeutic levels, are combined with any number of related therapeutic forms (for example, before, simultaneously or after) to be administered to a patient. The therapeutic forms include, but are not limited to treatments with agents such as antiviral therapy, cidofovir and interleukin-2, cytarabine (also known as ARA-C) or natalizumab treatment for MS patients, or efalizumab treatment for psoriasis patients or other treatments for PML patients. In a further embodiment, the T cells of the invention can be used in combination with chemotherapy, radiation, immunosuppressive agents such as cyclosporin, azathioprine, methotrexate, mycophenolate mofetil and FK506, antibodies or other immunotherapeutic agents. In a further embodiment, the cell composition of the invention is combined with a bone marrow transplant using a chemotherapeutic agent such as fludarabine, external beam radiation therapy (XRT), cyclophosphamide (for example, before, simultaneously or after) and administered to a patient. For example, in an embodiment, the subject may undergo standard treatment with high-dosage chemotherapy followed by peripheral blood stem cell transplantation. In some embodiments, the subject receives an injection of the expanded immune cells of the invention after transplantation. In an additional embodiment, the expanded cells are administered prior to or after a surgery.

The dosage administered to the patient in the above treatment varies with the precise nature of the condition and the recipient. A ratio of the dosage administered to a human can be determined according to practices accepted in the art. Generally, the modified T or NK cells of the invention can be administered to a patient at an amount of $1\times10^6$-$1\times10^{10}$ by, such as intravenous reinfusion for each treatment or course.

The main advantages of the invention are described as follows.

(1) The CAR of the invention has specific selectivity in vitro, and the CAR-positive target cells can be efficiently sorted by a secondary cell sorting for in-vitro proliferation of cells. Therefore, the ratio of the CAR-positive target cells in the final product is significantly increased, improving the efficiency of preparing CAR gene-modified immune cell products. The present invention provides a more reliable technical support for further promotion and application of such products in clinical practice.

(2) T cells or NK cells undergo a second activation when the CAR of the invention is stimulated by the selective domain-specific antibody, thereby significantly increasing the proliferation efficiency.

(3) Compared to ordinary T or NK cells, the genetically engineered T or NK cells of the invention have comparable proliferation capacity and performance. The genetically engineered T or NK cells have better tumor-killing effects against CD19-positive cells and higher release levels of killing-associated factors.

The invention will be further illustrated below in conjunction with specific embodiments. It should be understood that the embodiments are merely used to illustrate the invention, but are not intended to limit the scope of the invention. The experimental methods not specified with specific conditions in the following examples are carried out according to conventional conditions, such as the conditions described in Sambrook et al., Molecular Cloning: Laboratory Manual (New York: Cold Spring Harbor Laboratory Press, 1989), or according to the conditions recommended by the manufacturer. Unless otherwise specified, percentages and parts used herein are based on weight.

Example 1 Preparation of CAR Molecule with Specific Selectivity

A specific primer was designed. Targeted amplification of coding sequences of a domain (SEQ ID No.1), and a hinge region and a transmembrane region (SEQ ID No.2) of a leader peptide of T cell receptor protein CD8 molecule were performed by PCR from human cDNA library. Coding sequences (SEQ ID No.3) of an intracellular signal-transduction domain CD3ζ of a CD3 molecule and an intracellular signal-activation domain of a CD137 molecule of the T cell receptor protein were also amplified. A domain with specific selectivity in the CAR molecule was derived from a sequence (SEQ ID No.4) encoding amino acids at positions 95-104 of C-terminal domain of human nuclear protein La/SS-B. The sequence was synthesized by a chemical method and inserted between VL and VH domains of a coding region of a humanized single-chain antibody ScFv in the CAR molecule. The structure of the CAR was $F_0$-$F_1$-$L_1$-Z-$L_2$-$F_2$-H-TM-C-CD3ζ, and the amino acid sequence was shown in SEQ ID NO.8. The above various coding sequences were assembled and amplified in vitro using nested-PCR to construct a chimeric antigen receptor coding sequence including a specifically selective domain. The anti-human CD19 humanized single-chain antibody was exemplarily used to construct a CD19-targeting chimeric antigen receptor molecule CD19-hsCAR comprising the above selective sequences. This is for the detailed description of use of the CAR molecular domain in the downstream preparation of CAR gene-modified T cells.

Example 2 Construction of Expression Vector of Chimeric Antigen Receptor

The coding sequence of the CAR in Example 1 (SEQ ID NO.7) was cloned into lentiviral expression vector pLenti-CMV using molecular cloning techniques. To demonstrate the benefits of the modified CAR molecule in the preparation of CAR-T cells, a conventional CAR molecule targeting CD19 antigen whose amino acid sequence was shown as SEQ ID NO.9 (Patent No. CN103492406A), was used as a control to construct a CD19-mCAR viral expression vector. The above lentiviral expression vector was used together with a helper plasmid for virus encapsulation, plasmid psPAX2 encoding viral nucleocapsid proteins Gag/Pol and Rev, and plasmid pVSVG encoding a viral envelope protein for subsequent preparation of different lentiviruses encoded by CAR gene. FIG. 1 shows the identification results of viral expression vectors carrying different CAR protein coding sequences by agarose gel electrophoresis.

```
                                                  (SEQ ID NO. 9)
MALPVTALLLPLALLLHAARPDIQMTQTTSSLSASLGDRVTISCRASQDI

SKYLNWYQQKPDGTVKLLIYHTSRLHSGVPSRFSGSGSGTDYSLTISNLE

QEDIATYFCQQGNTLPYTFGGGTKLEITGGGGSGGGGSGGGGSEVKLQES

GPGLVAPSQSLSVTCTVSGVSLPDYGVSWIRQPPRKGLEWLGVIWGSETT

YYNSALKSRLTIIKDNSKSQVFLKMNSLQTDDTAIYYCAKHYYYGGSYAM

DYWGQGTSVTVSS.
```

Example 3 Preparation of CAR-Encoding Viruses

HEK193T cells were used for encapsulation to prepare CAR-encoding viruses. HEK293T cells in logarithmic growth phase were digested and centrifuged at 800 rpm for 5 minutes. The medium was removed and precipitate was resuspended with DMEM medium (Gbico) containing 10% FBS (Gbico). After cell counting, the cell suspension was adjusted to a density of $3 \times 10^6$ cells/mL and placed in an incubator at 37° C. for use. Transfection of plasmids for viral encapsulation was performed with a Lipofectamine 3000 kit (Thermo Fisher) following the specification. Three plasmids required for lentiviral encapsulation, including viral vectors carrying different CAR genes and the two helper plasmids in Example 2, were mixed with Lipofectamine 3000 at a ratio as recommended in the specification to prepare a DNA-liposome complex. The DNA-liposome complex was allowed to stand at room temperature for 15 minutes. After that, the DNA-liposome complex was added to a 6-well culture plate, 1 mL per well. Then, the previously prepared HEK293T cell suspension was mixed gently and added to the 6-well culture plate to mix uniformly with the liposome complex. The 6-well culture plate continued to incubate in an incubator. Supernatants containing the viruses were collected at 24 and 48 hours, respectively. After last collection of the supernatant, the collected supernatants were centrifuged at 2,000×g for 10 minutes and filtered with a 0.45 μm filter membrane. The resulting filtrate was subpackaged and stored at −80° C. for use.

Example 4 Preparation of CAR-Encoding Gene-Modified T Cells In Vitro

Using a heparin anticoagulant tube, 30 mL of peripheral blood from a healthy human was collected and separated with a lymphocyte separation medium by centrifugation at 800×g and 25° C. for 15 minutes. The acceleration and deceleration parameters of the centrifuge were set to 1 and 0, respectively. After the centrifugation, the resulting buffy coat was transferred to a new centrifuge tube. Cells were resuspended with D-PBS followed by centrifugation at 400×g for 10 minutes. The resulting cells were resuspended with an X-VIVO15 medium (LONZA) containing 5% normal human AB serum, and adjusted to a density of $1\text{-}2 \times 10^6$ cells/mL. T cells were sorted using magnetic beads (Gbico Inc.) coupled with CD3/CD28 antibody according to the specification. The sorted cells were resuspended with an X-VIVO-15 medium containing 1000 IU/mL of IL-2, and inoculated at a density of $1\text{-}2 \times 10^6$ cells/mL into a culture flask pre-coated with 10 μg/mL of Retronectin (Takara) and 5 μg/mL of OKT-3 (Takara). The culture flask was transferred to an incubator at 37° C. for incubation.

After 24 hours of culture, the cells were placed under a microscope to observe the cell states and then infected with lentiviruses. The infection was carried out with the viruses encoding CD19-hsCAR protein and viruses encoding CAR protein as control. The infected cells were collected and centrifuged at 400×g for 10 minutes. Then, the cell precipitate was resuspended and adjusted to a density of 3-5×10$^6$ cells/mL. The cells were inoculated into a culture flask pre-coated with 10 μg/mL of Retronectin. Viruses were transferred from an −80° C. freezer to ice to melt. The viral load required was calculated according to MOI=50, based on the number of the cells to be infected and viral titer. The viruses were diluted with an X-VIVO-15 medium and mixed with the cells followed by addition of polybrene (Sigma) to a final concentration of 8 μg/mL. The system was mixed uniformly and then cultured in an incubator. The medium was replaced with a fresh one after 8 hours to continue the culture.

On day 5, T cells infected with the viruses encoding CD19-hsCAR protein were collected. The magnetic beads coated with anti-human nucleoprotein La/S-BB polypeptide antibody were used for the secondary sorting of T cells using a cell sorting method, where the ratio of the magnetic beads to the T cells was 1:1. The sorted cells were inoculated into a culture flask for culture. Then, different groups of T cells were supplemented with the medium every 2-3 days according to the cell growth state to maintain a density of 1-1.5×10$^6$ cells/mL. The preparation was completed until the 14$^{th}$ day culture. The prepared cells were collected and cryopreserved in a cell cryoprotectant for subsequent analysis.

Figure 2:
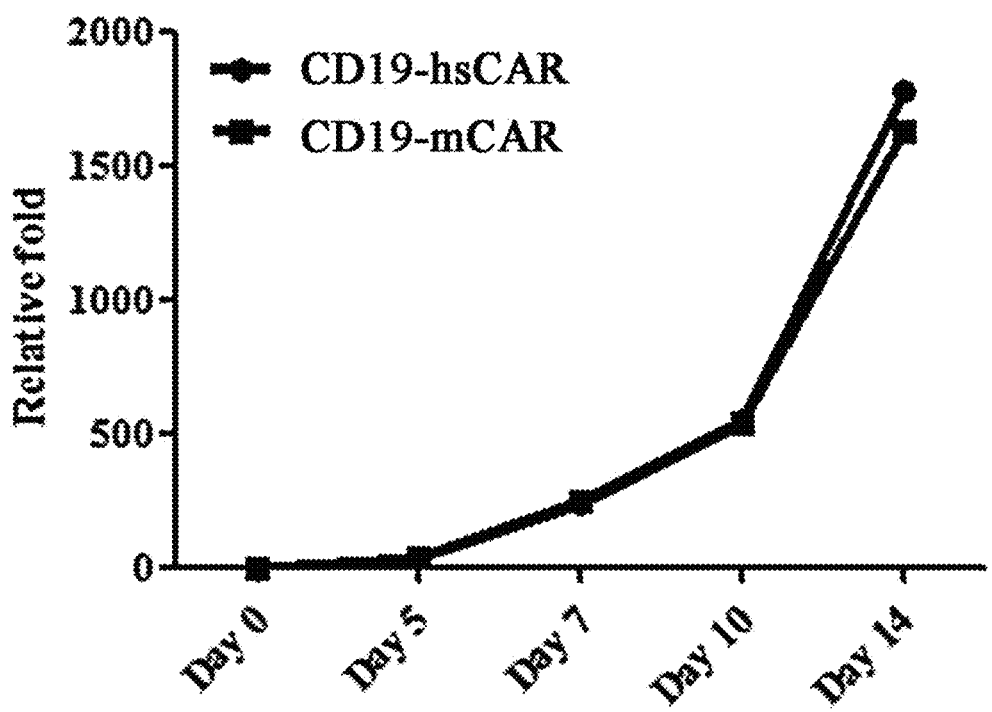
FIG. 2 shows the measurement results of in vitro proliferation of T cells infected with CD19-hsCAR and CD19-mCAR viruses.
Figure 3:
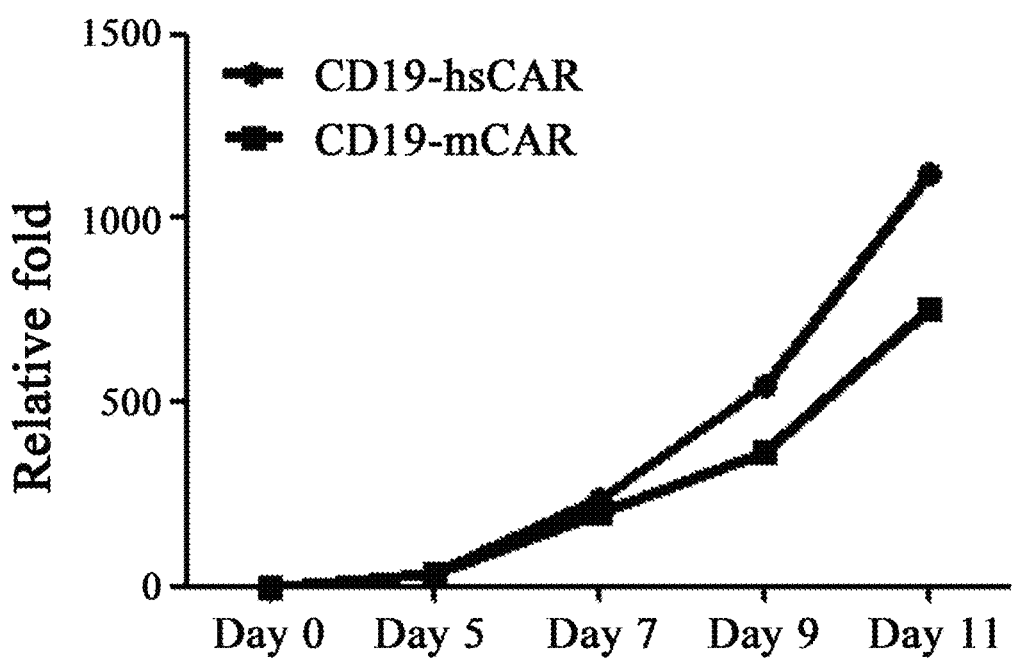
FIG. 3 shows the in vitro proliferation of two types of T cells carrying different CAR molecules after stimulation by peptide-specific antibody.
Figure 4:
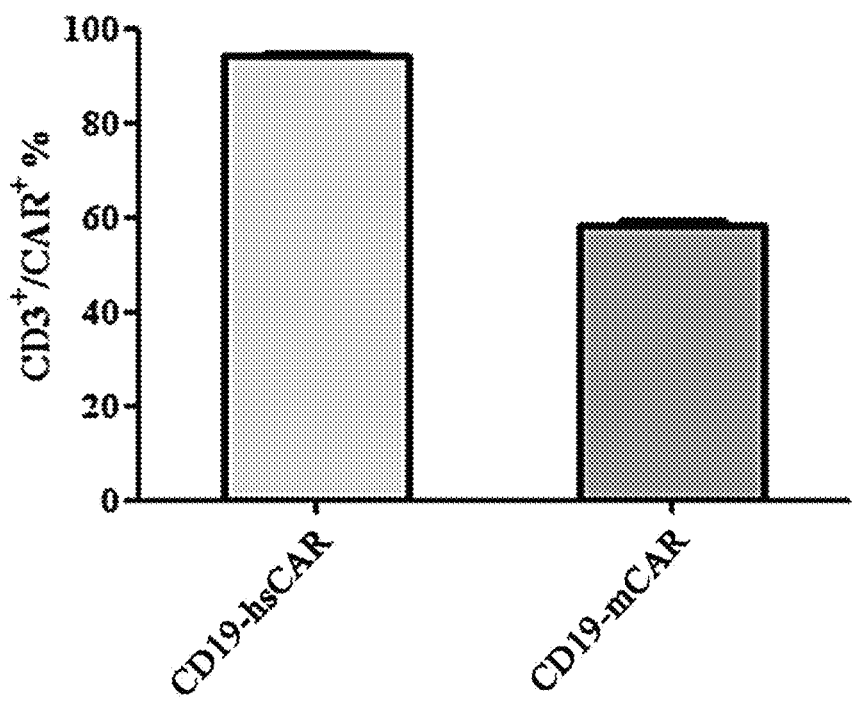
FIG. 4 shows the purity of T cells expressing different CAR receptors in the final product.
Figure 6:
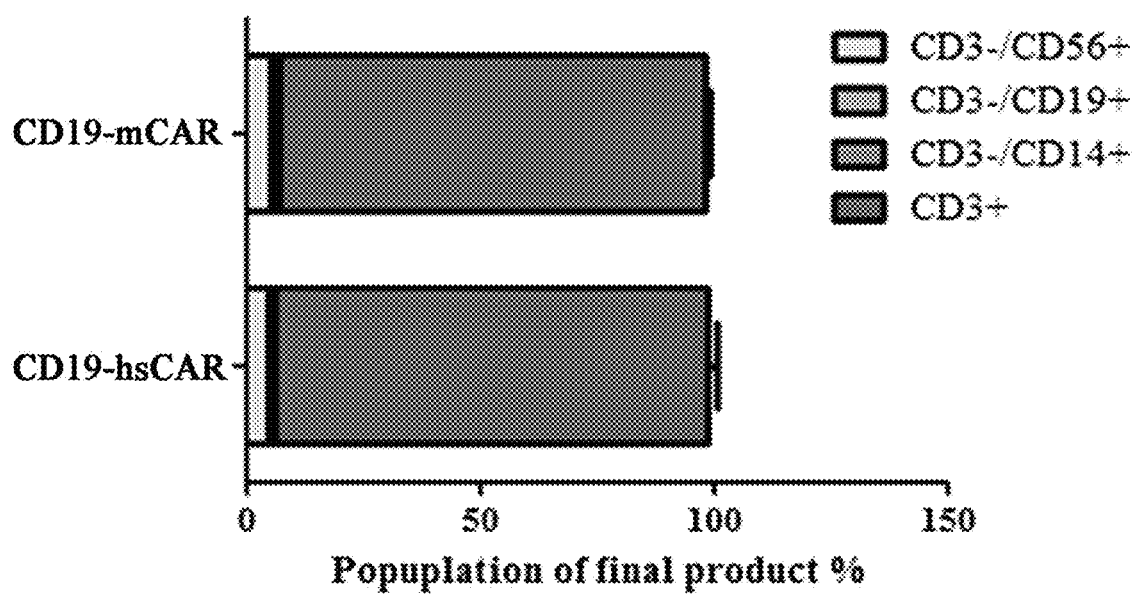
FIG. 6 shows the ratio of different cell subpopulations in the T cell final product expressing different CAR receptors.

FIG. 2 shows the proliferation curves of T cells infected with different CAR protein molecules during the culture. The results showed that the proliferation capacity of T cells in each of the groups was substantially the same without significant difference, indicating that the introduction of a specifically selective domain to the CAR molecule did not affect the proliferation capacity of T cells genetically modified with CAR. FIG. 3 showed proliferation curves of T cells infected with different CAR protein molecules after stimulation by secondary cell sorting with peptide screening. It can be seen from FIG. 3 that the proliferation efficiency of CD19s-CAR-T cells was significantly higher than that of CAR-T cell control group stimulated by secondary cell sorting. FIG. 4 shows the results of purity analysis of CAR-positive cells in different groups of CAR genetically modified-T cell final products by flow cytometry, indicating that the purity of CD19-hsCAR-T cells was significantly higher than that of the control group. Therefore, it can be demonstrated that the introduction of the specifically selective domain can effectively increase the ratio of CAR-positive cells in the final product, thereby improving the purity of the final product. In addition, the results of cell subpopulation analysis showed that there was no significant difference in the ratio of different cell subpopulations in the final product compared to the control group, indicating that the expression of CD19-hsCAR molecules in T cells did not affect the proliferation of different cell subpopulations in vitro (FIG. 6).

Example 5 Preparation of NK Cells Modified with the CAR-Encoding Gene In Vitro

Using a heparin anticoagulant tube, 35 mL of peripheral blood from a healthy human was collected, and separated with a lymphocyte separation medium by centrifugation at 800×g and 25° C. for 15 minutes. The acceleration and deceleration parameters of the centrifuge were set to 1 and 0, respectively. After the centrifugation, the resulting buffy coat was transferred to a new centrifuge tube. Cells were resuspended with D-PBS followed by centrifugation at 400×g for 10 minutes. The resulting cells were resuspended with a SCGM medium (Cellgenix) containing 10% of normal human AB serum and adjusted to a density of 1-2×10$^6$ cells/mL. The resuspended cells were inoculated at a density of 1.5×10$^6$ cells/mL into a culture flask or a petri dish to which OKT-3, mouse anti-human CD16 monoclonal antibody and IL-2 were added to respective final concentrations of 5 ng/mL, 20 μg/mL and 1000 IU/mL. The culture flask or petri dish was transferred to an incubator at 37° C. for incubation.

Figure 5:
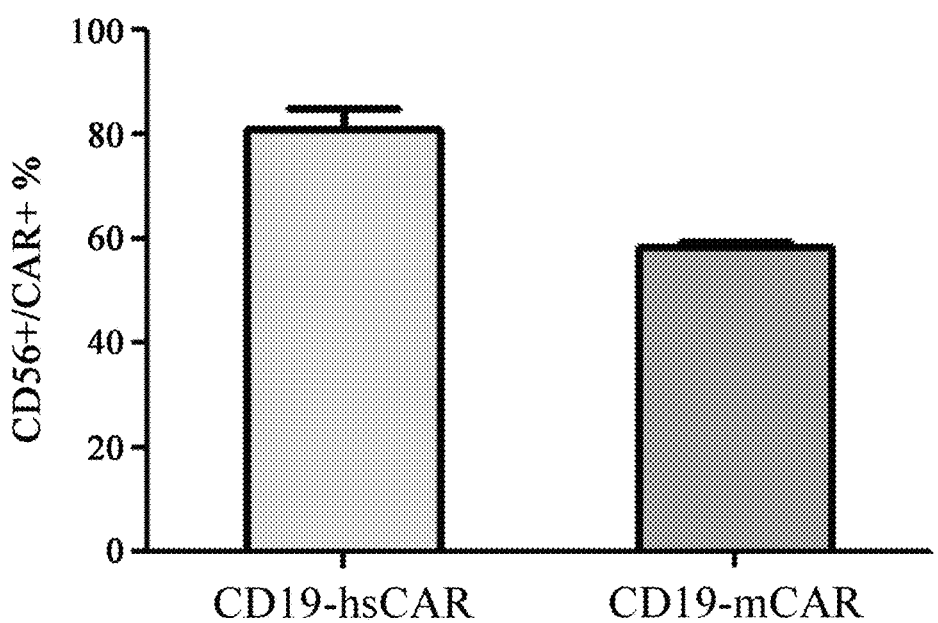
FIG. 5 shows the purity of NK cells expressing different CAR receptors in the final product.

On day 3-4, the infection with lentiviruses and the sorting of positive NK cells after infection were carried out according to the methods described in Example 4. After the sorting, the cells were harvested until 14$^{th}$ day culture and cryopreserved at −193° C. for long-term storage, or directly used for subsequent analysis. The purity of CAR-positive NK cells in the final product was shown in FIG. 5, and the ratio of CAR-positive NK cells in the final products of CD19-hsCAR-NK is significantly higher than that in the final products of CD19-mCAR-NK.

Example 6 Evaluation of In Vitro Cytotoxicity

Figure 7:
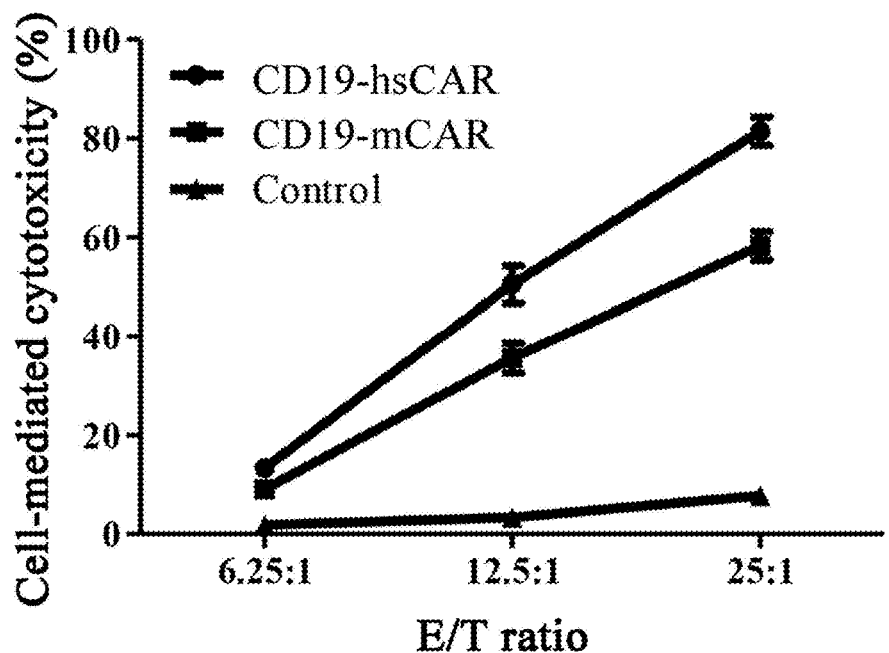
FIG. 7 shows the evaluation of in vitro cytotoxicity of T cells expressing different CAR molecules.

The in-vitro cytotoxicity of the CD19-hsCAR group and the CD19-mCAR group was evaluated by LDH release method using a CD19-positive human B-cell lymphoma Raji cell line. The LDH release was determined using Progema kit and following the instructions. The cytotoxicity was calculated according to Formula 1 using the absorbance values of each group. Specifically, Raji cells in the logarithmic growth phase were collected and adjusted to a density of 4×10$^6$ cells/mL. The cells then were inoculated into a U-bottom 96-well plate, 50 μL per well (2×10$^4$ cells per well). Different groups of CAR-T cells were collected, resuspended, and co-cultured with Raji cells in an E/T ratio of 25:1, 12.5:1, 6.25:1 and 3.125:1, respectively. After 4 hours of culture, the cell supernatants were collected to measure the LDH release according to the kit instructions, thereby evaluating the cytotoxicity of different groups of CAR-T cells. As shown in FIG. 7, the T cells expressing CD19-hsCAR had a better cytotoxicity than the control group.

Figure 8:
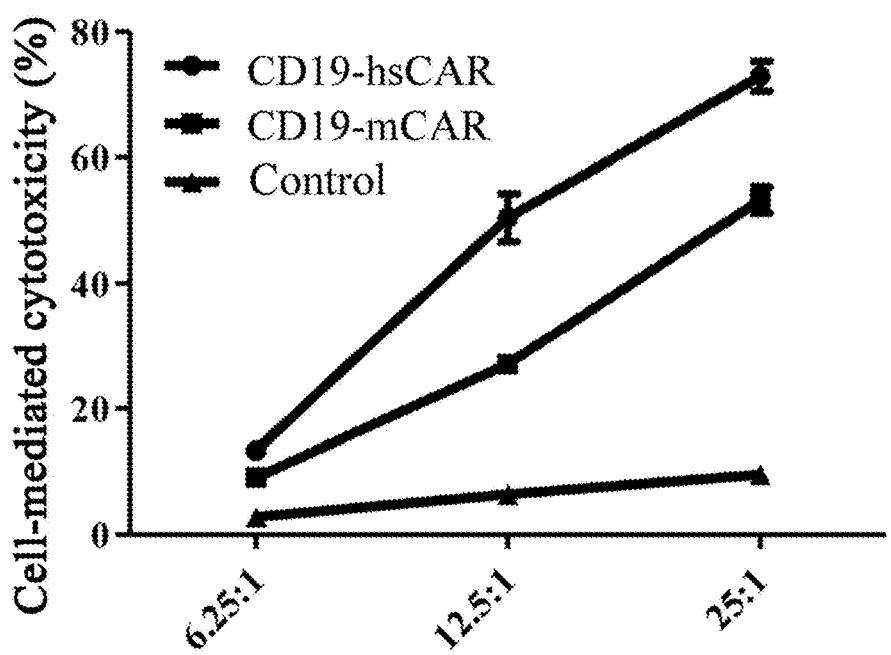
FIG. 8 shows the evaluation of in vitro cytotoxicity of NK cells expressing different CAR molecules.

In the determination of the cytotoxicity of CD19s-CAR-NK cells, the cytotoxicity of NK cells infected with different CAR protein molecules on Raji cells was evaluated according to the above method using the Raji cell line as target cells and normal NK cells as control. As shown in FIG. 8, the results indicated that the cytotoxicity against Raji cells of NK cells expressing CAR protein was significantly higher than that of NK cells of control group, and the cytotoxicity against Raji cells of CD19s-CAR-NK cells was higher than that of CD19-mCAR-NK cells.

Killing efficiency (%)=(experimental group−spontaneous release of effector cells−spontaneous release of target cells)/(maximum release of effector cells−spontaneous release of effector cells)×100%.    Equation 1:

Example 7 Measurement of Cytokine Release

Figure 9:
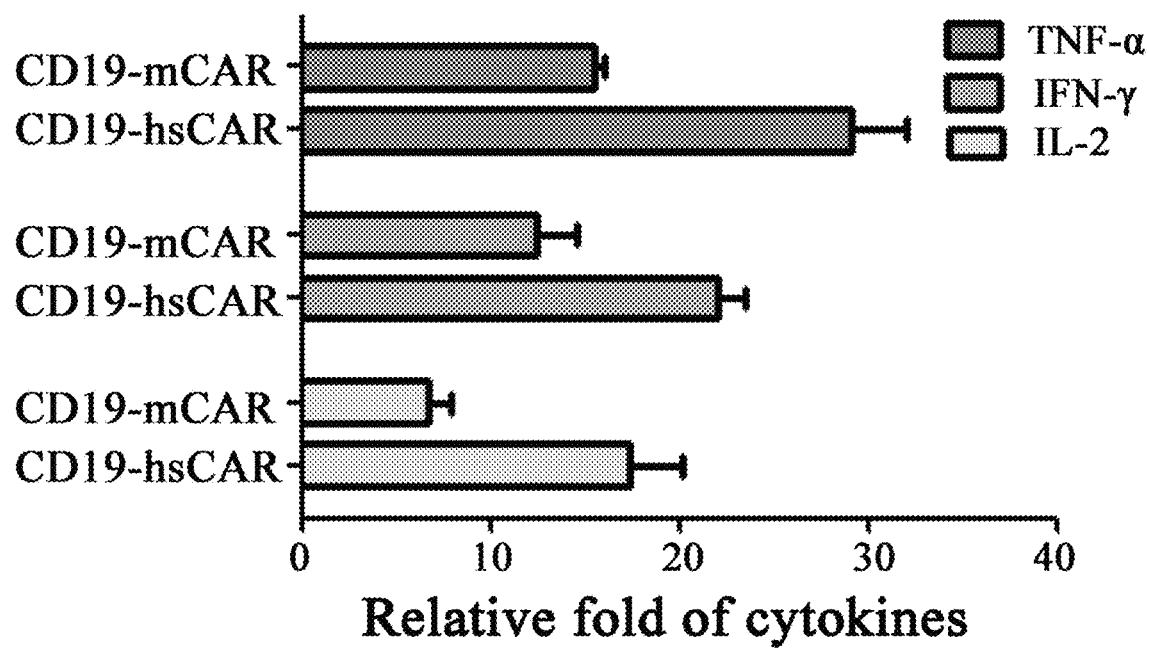
FIG. 9 shows the in vitro release activity test of killing-associated factors of T cells modified with different CAR molecules.

Levels of T cell killing-related cytokines IL-2, IFN-γ and TNF-α released by T cells genetically modified with different CAR during killing were detected using an ELISA kit (Neobioscience Inc.). Raji cells were inoculated to a U-bottom 96-well culture plate according to the inoculation load in Example 5, and then mixed with T cells expressing different CAR molecules in a T/E ratio of 1:25 for a co-culture. After 12 hours of culture, the cell supernatant was collected for the determination of concentrations of cytokines IL-2, IFN-γ and TNF-α, respectively following the specification of the ELISA kit. As shown in FIG. 9, the release levels of the killing-related cytokines of the T cells expressing the CD19-hsCAR receptor were significantly higher than those of the control group of T cells expressing the CAR receptor, indicating that the CAR-modified T cells prepared using the method of the invention had more desirable cytotoxicity.

Design and Property of Humanized Selective (hs) CD19 CAR

Figure 10A:
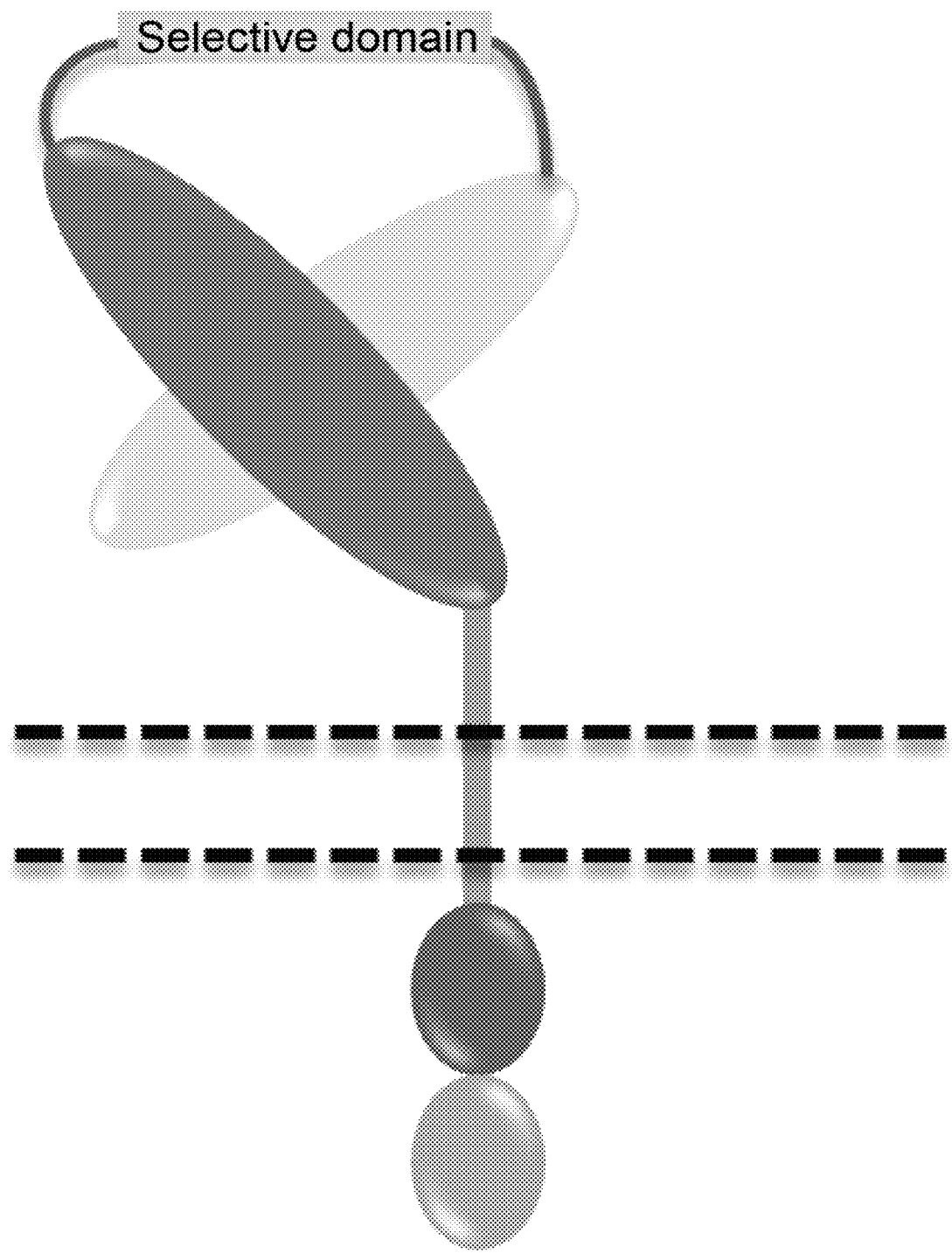
FIGS. 10A-10J show the design and evaluation of CD19 hsCAR.

The humanized selective CAR was based on the second generation CAR which included a hinge domain and transmembrane region of the human CD8a molecule, and an intracellular signaling domain containing both 4-1BB and CD3ζ as the co-stimulation region. The variation in CAR transduction rates, particularly in patient-derived T cells, and the non-selective expansion of both CAR-positive and -negative T cells prior to infusion, added uncertainty to quality control and interpretation of clinical results. To address this issue, we incorporated a selective domain in the linker sequence between the heavy chain and light chain of the scFv area (FIG. 10A). The selective domain is part of a natural protein that exists in human cell nucleus, and exposure to SmAb leads to selective activation and expansion of T cells transduced with certain CARs.

Figure 10B:
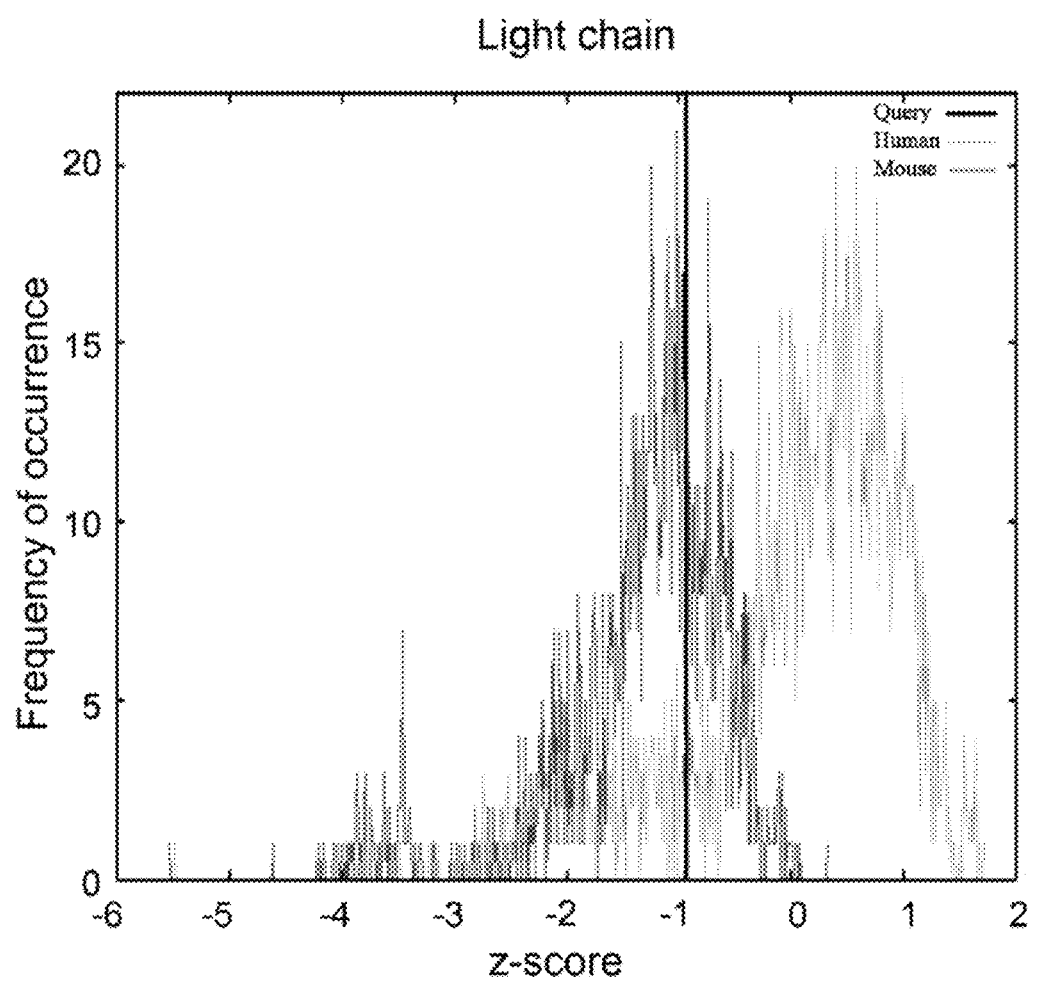
Figure 10C:
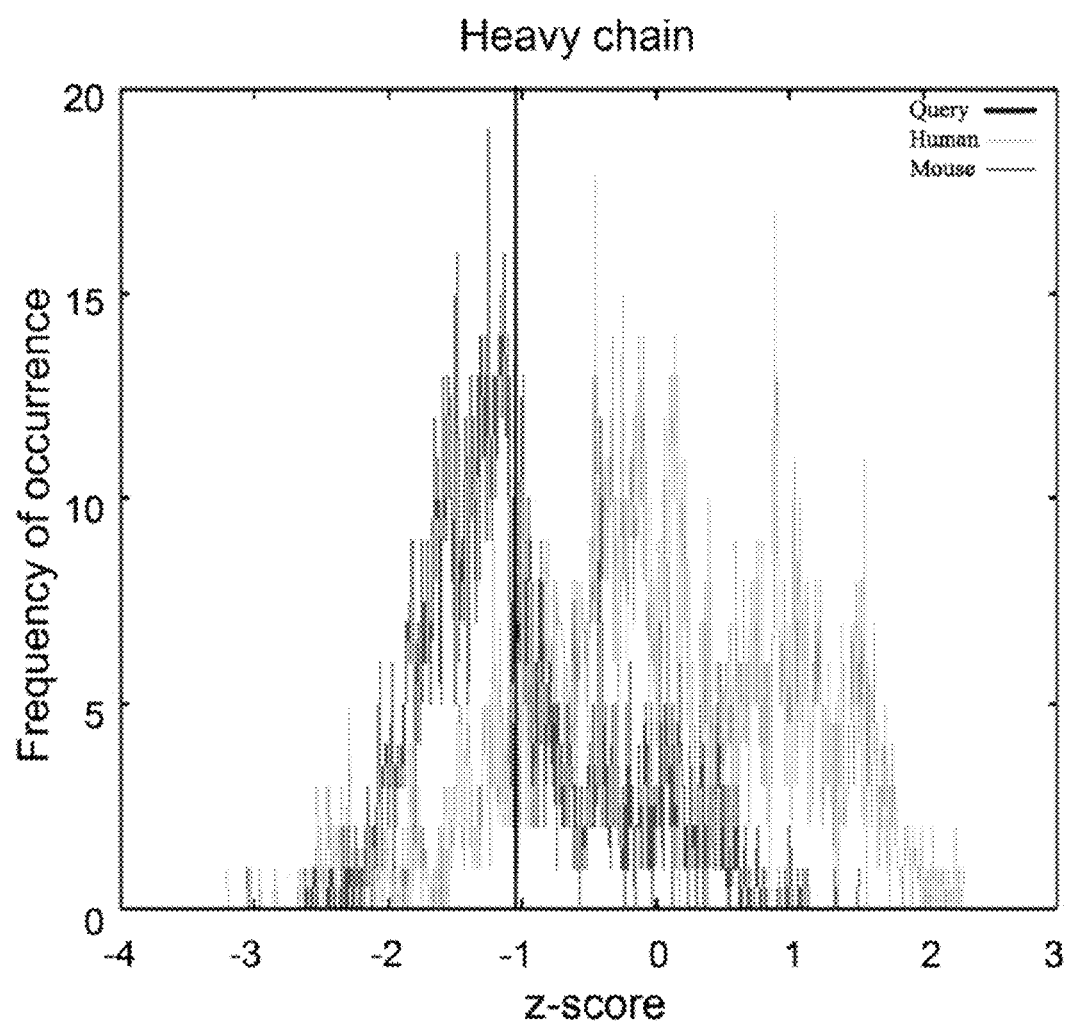
Figure 10D:
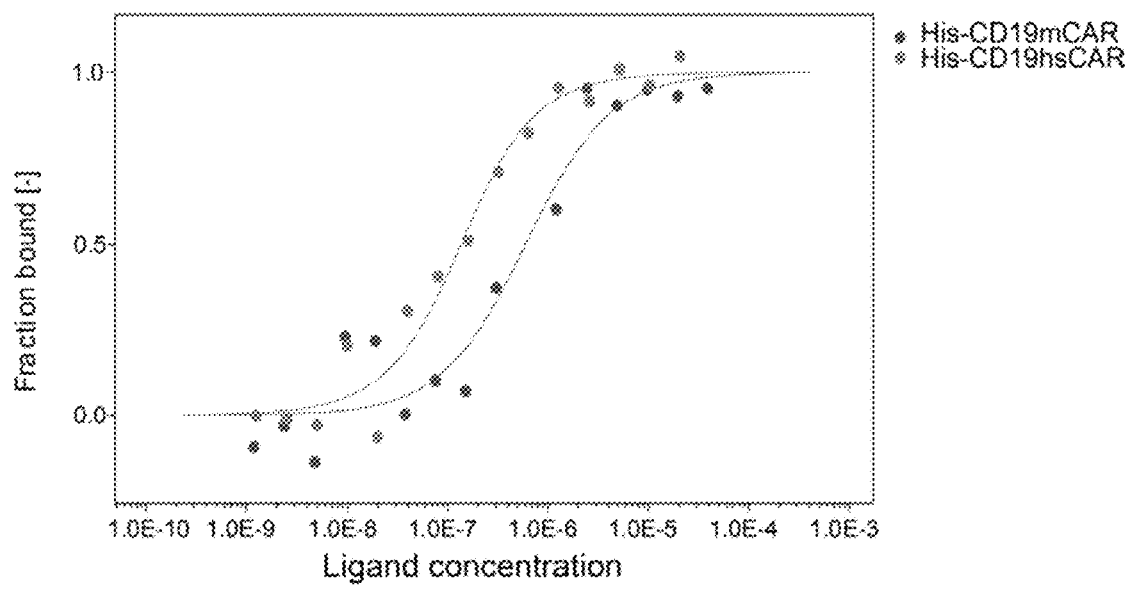
Figure 10E:
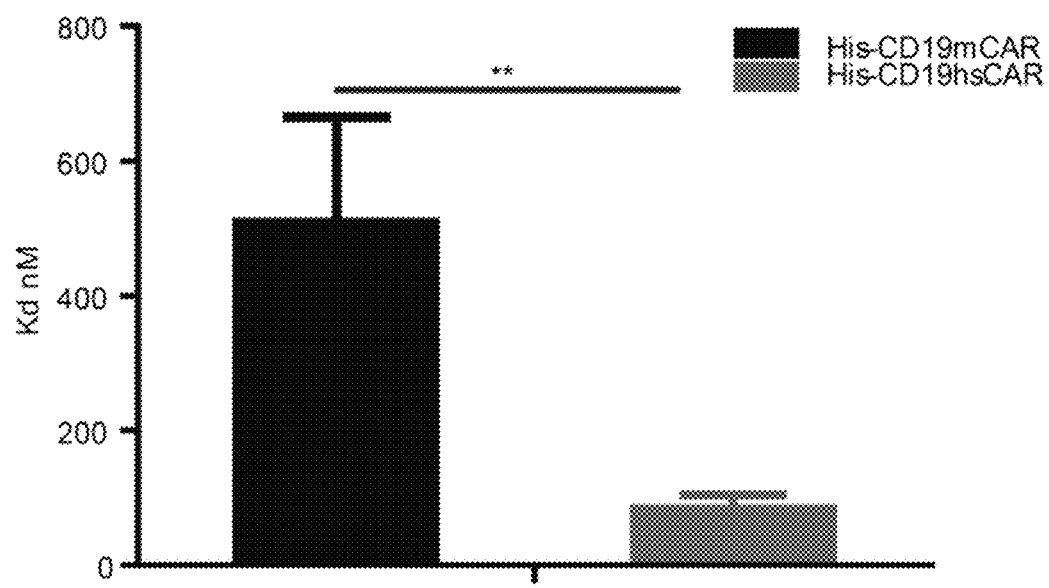

Another improvement to the traditional CD19 CAR was the humanized sequence of the scFv region (FIGS. 10B-10C). Murine CD19 scFv sequence may be recognized by the host immune system and rendered the second murine CD19 CAR-T cell infusion ineffective. The humanization of the scFv region was in agreement with the prediction of the online software at www.abysis.org (FIGS. 10B-10C). An important determinant of the quality of CAR was the specificity to antigen. Using purified human CD19 protein as target antigen, we tested the affinity of murine CD19 CAR and CD19 hsCAR. The kinetics of binding between murine and humanized selective CARs to the ligand (hCD19) was plotted by using MST assay (Monolith NT.115, NanoTemper) (FIG. 10D), and the Kd values for CD19 mCAR and hsCAR were 509.4±89.8 and 83.4±12.2 nM, respectively (FIG. 10E), suggesting that hsCAR possessed an affinity that was 6-fold greater than that of mCAR.

Figure 10F:
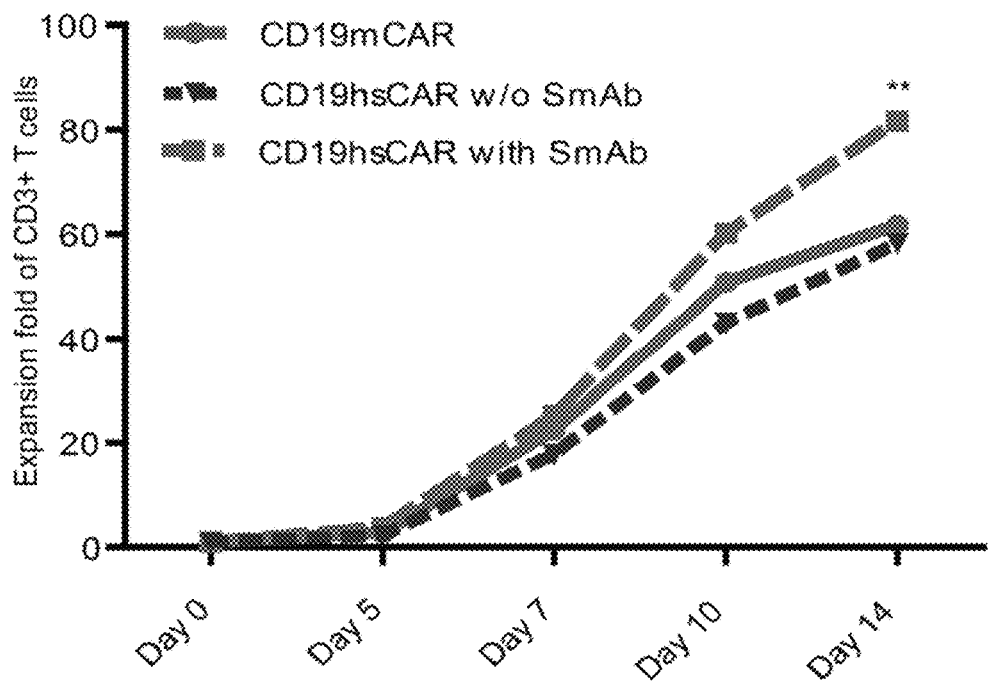

Also included in the design of CD19 hsCAR was the selective epitope E-tag. Clinical grade antibodies to selective domain, SmAb, was coated to the bottom of plates during the ex vivo expansion stage. Compared with CD19 mCAR-transduced PBMCs and CD19 hsCAR-transduced PBMCs without exposure to SmAb, CD19 hsCAR-transduced PBMCs exposed to SmAb showed a significantly greater proliferative capacity. On day 14, hsCAR-infected PBMCs exposed to SmAb expanded 81.6±3.38 times, while hsCAR-infected PBMCs without exposure to SmAb expanded 61.7±2.58 times, and mCAR-infected PBMCs 58.2±2.55 times (FIG. 10F).

Figure 10G:
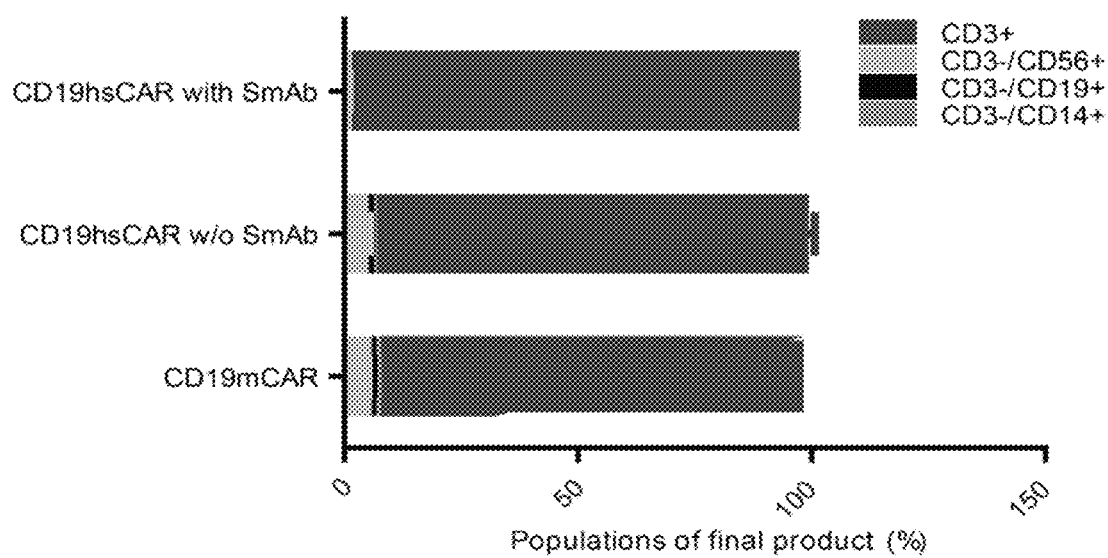
Figure 16A:
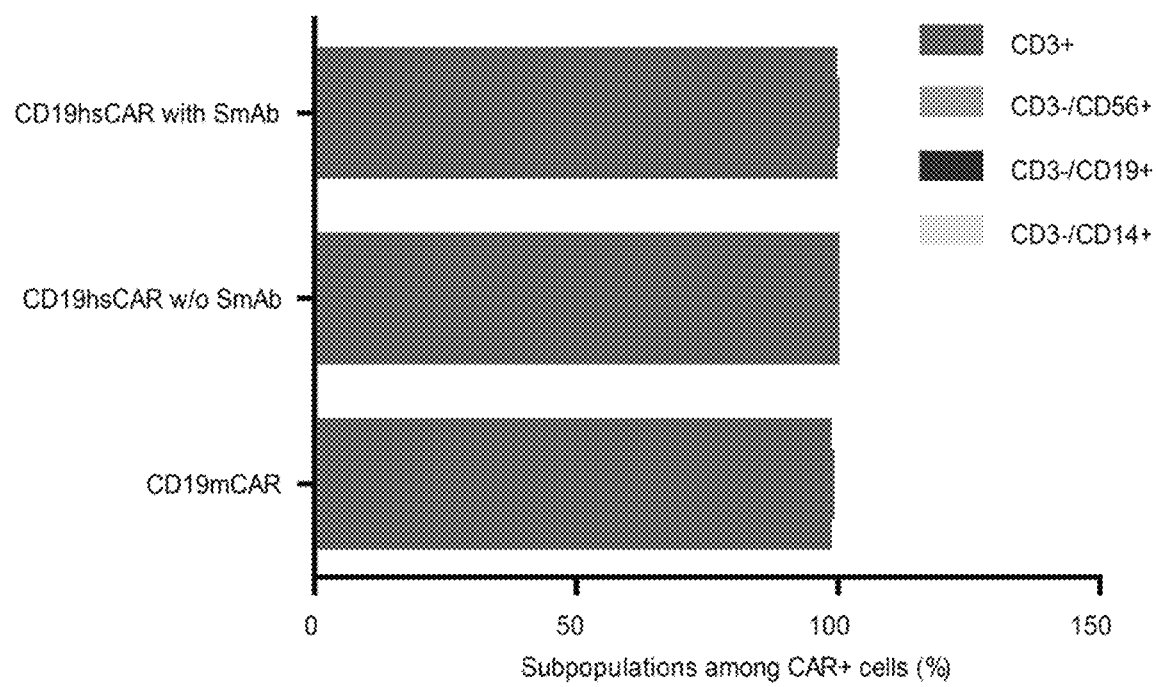
FIGS. 16A-16C show subpopulations in the CD19 mCAR-T and hsCAR-T cells with or without SmAb re-stimulation.

On day 14, among the final product, more than 95% of the total cells were CD3+ T cells; a small percentage of the total cells (<5%) were CD3−/CD56+ natural killer (NK) cells, and few CD3−/CD19+ B cells or CD3−/CD14+ cells were detected by flow cytometry (FIG. 10G). Among the CAR-positive cells, the proportions of each population were presented in FIG. 16A.

Figure 10H:
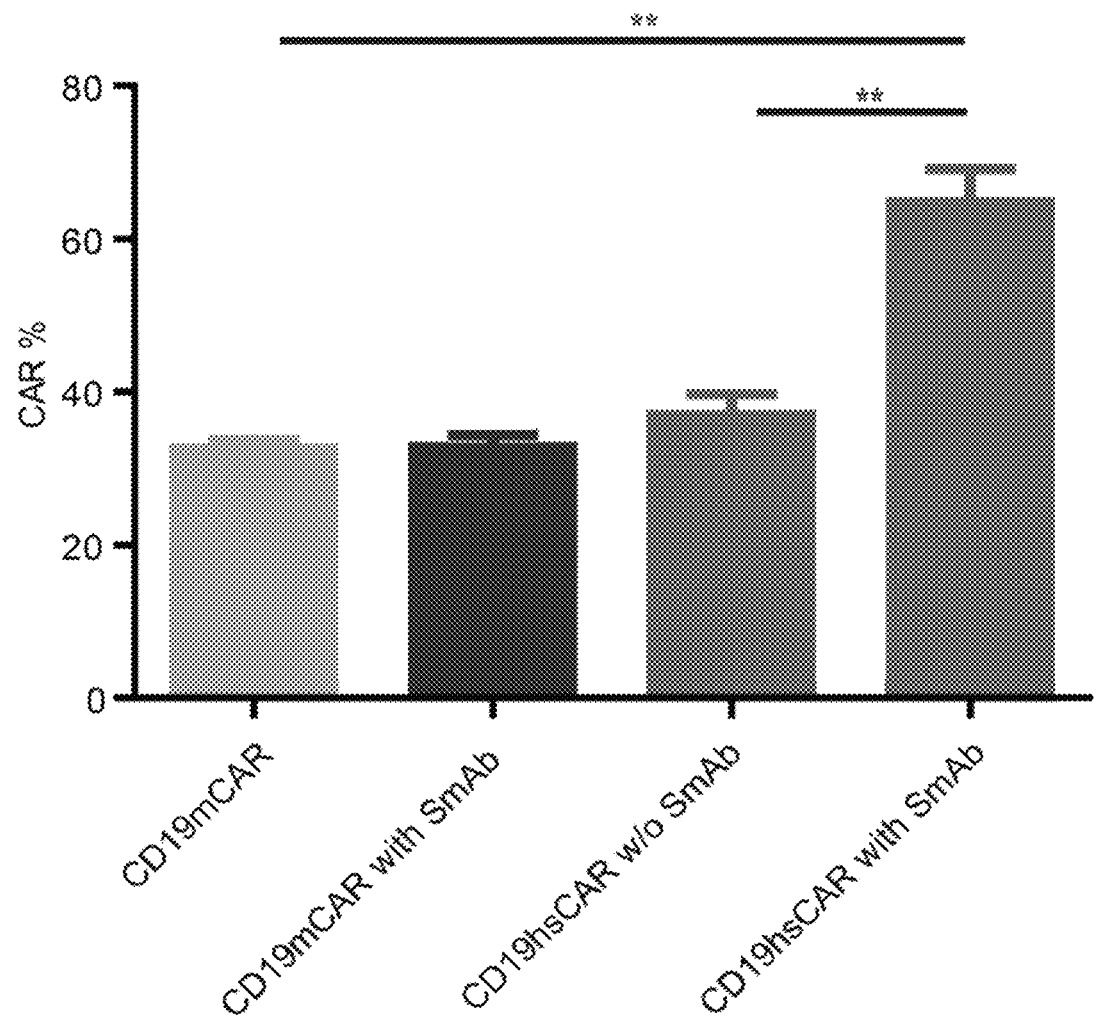
Figure 10I:
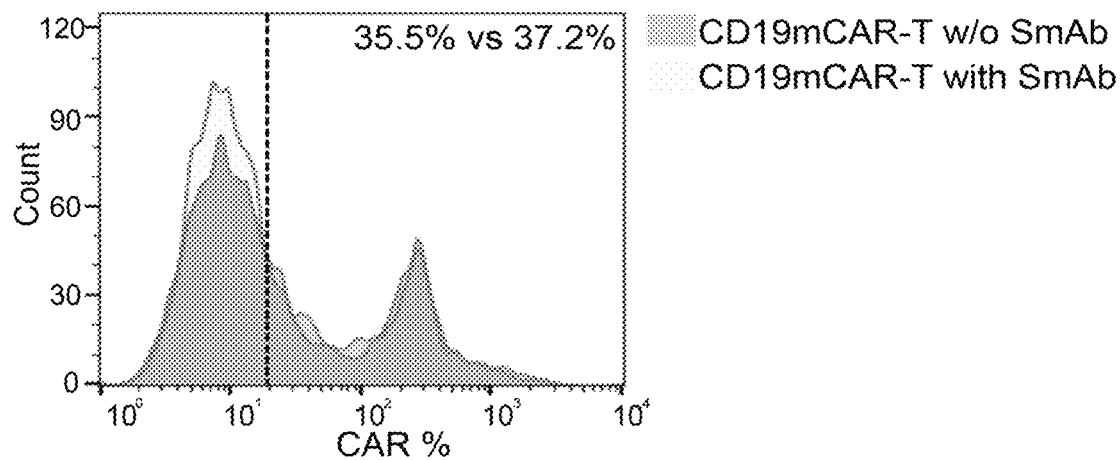
Figure 10J:
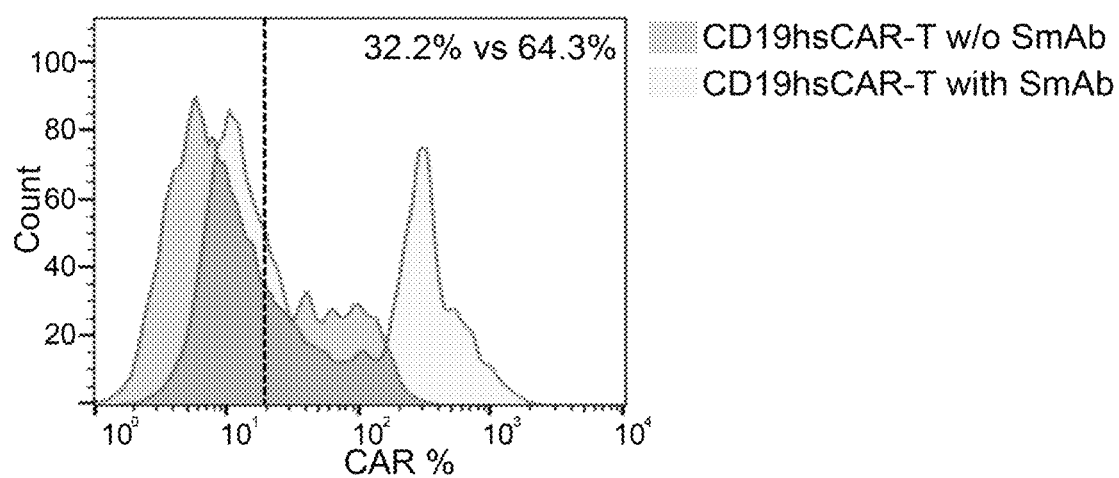

Evaluation of CAR-positive cells among the final products revealed that, on day 14, 64.73±4.4% of total cells were positive for CAR in the "CD19hsCAR+SmAb" group, significantly higher than those of the other three groups (FIGS. 10H-10J). The results confirmed that the selective domain can be used to specifically expand the CAR-transduced cells.

Improvement of CD19 hsCAR-T Cells on Anti-Tumor Cytotoxicity In Vitro

Figure 11A:
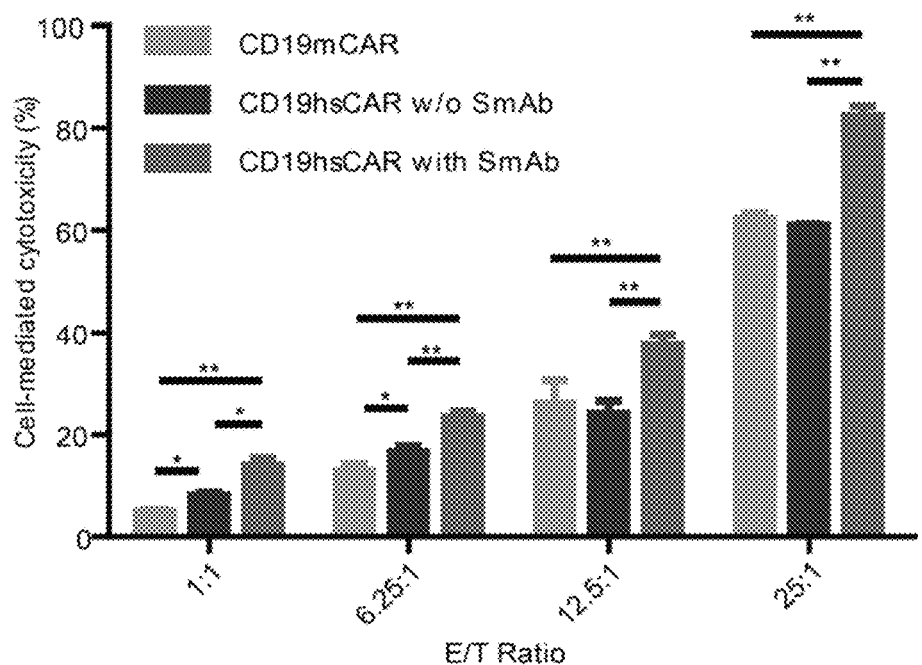
FIGS. 11A-11K show SmAb-mediated re-stimulation (targeting the selective domain of CD19 hsCAR) on the biological function and ratio of central memory T cells in the final product.
Figure 11B:
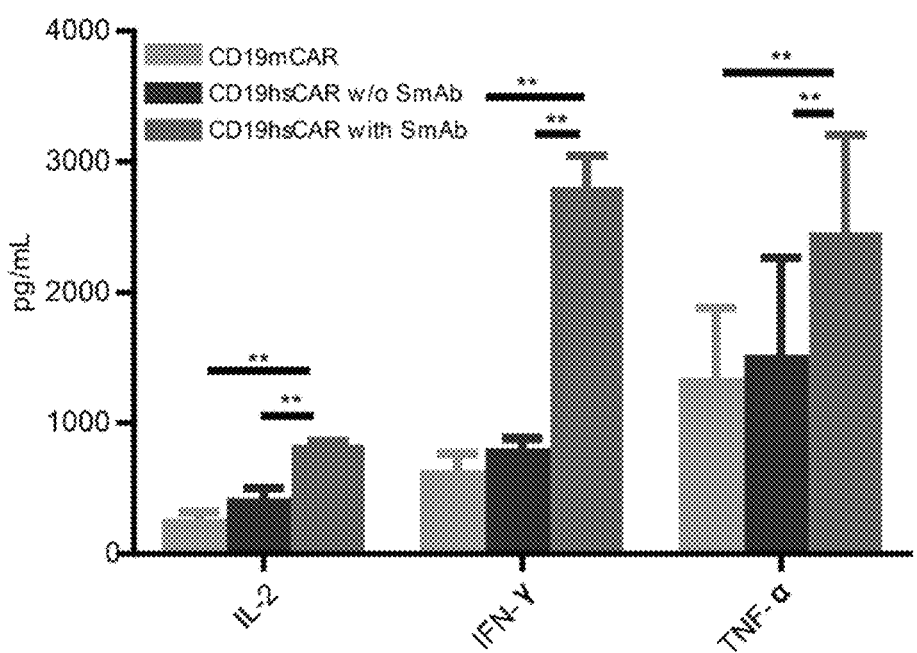

CAR-T cells of different groups (CD19 mCAR, CD19 hsCAR w/o SmAb, CD19 hsCAR with SmAb) were incubated with a leukemia Raji cell line at various E/T ratios. At the four ratios tested (1:1, 6.25:1, 12.5:1, and 25:1), CD19 hsCAR with SmAb all showed superior cytotoxicity vs. the other two groups (FIG. 11A). Interestingly, at lower E/T ratios (6.25:1), CD19 hsCAR w/o SmAb also showed a greater cytotoxicity compared with CD19 mCAR-T cells. Accordingly, CD19 hsCAR with SmAb, when incubated with Raji cells at E/T ratio 25:1, led to increased cytokine release of IL-2, IFN-γ, and TNF-α in the medium, as detected by ELISA (FIG. 11B).

Figure 11C:
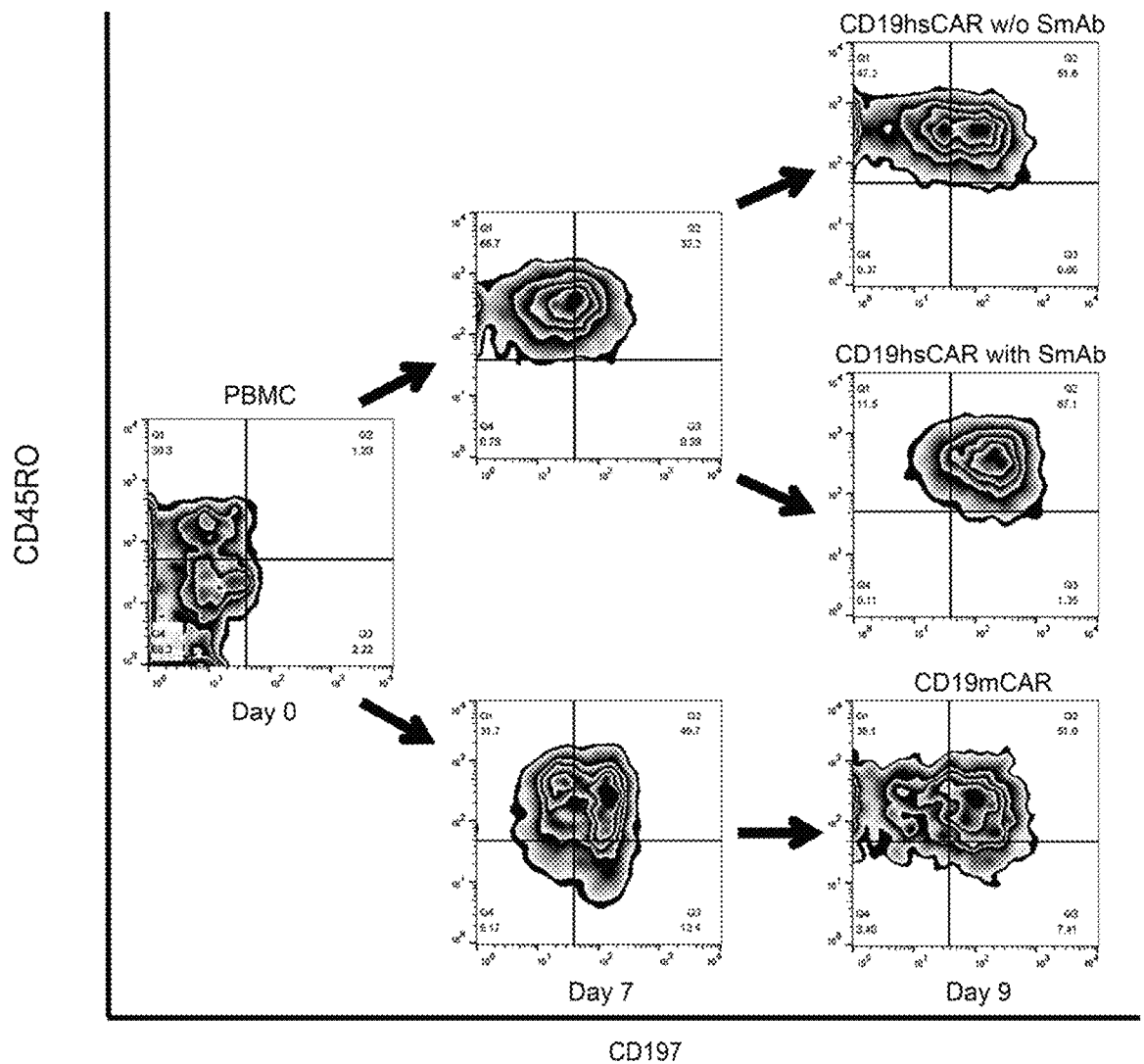
Figure 11D:
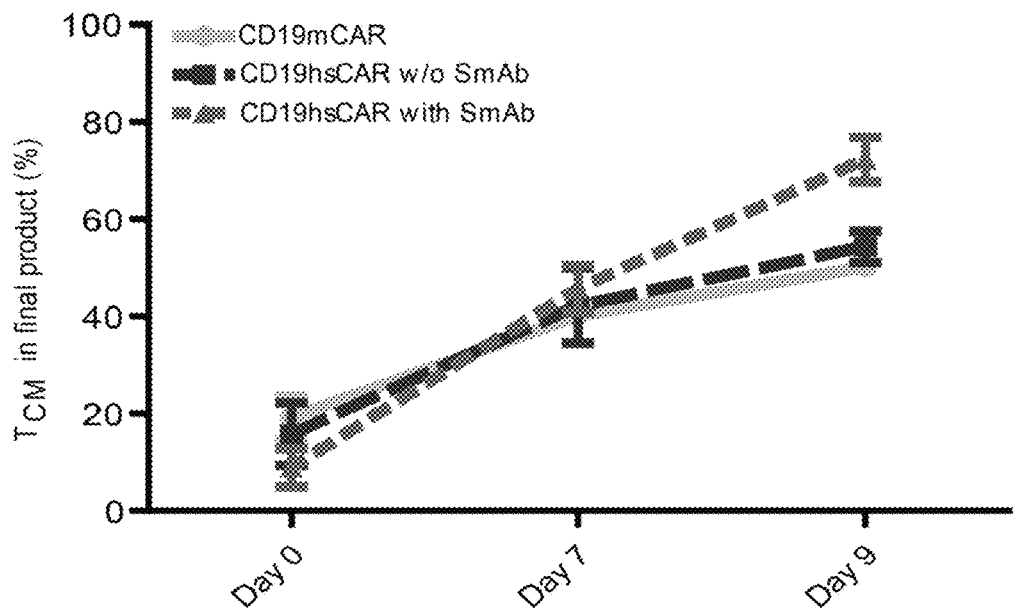
Figure 11E:
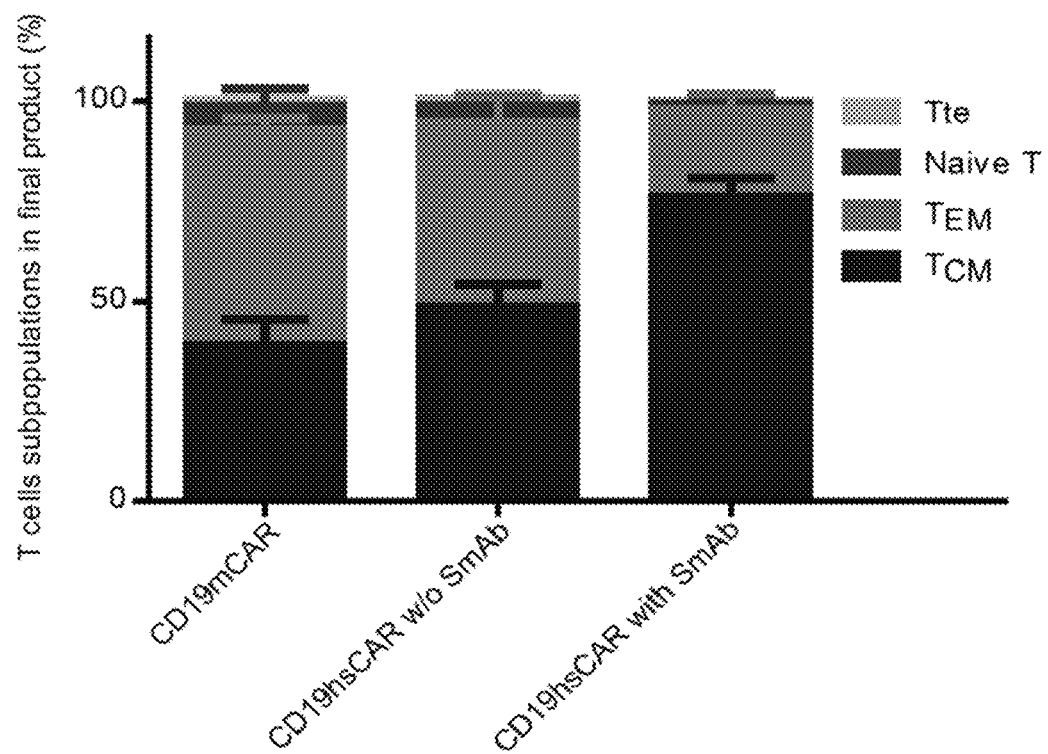
Figure 11F:
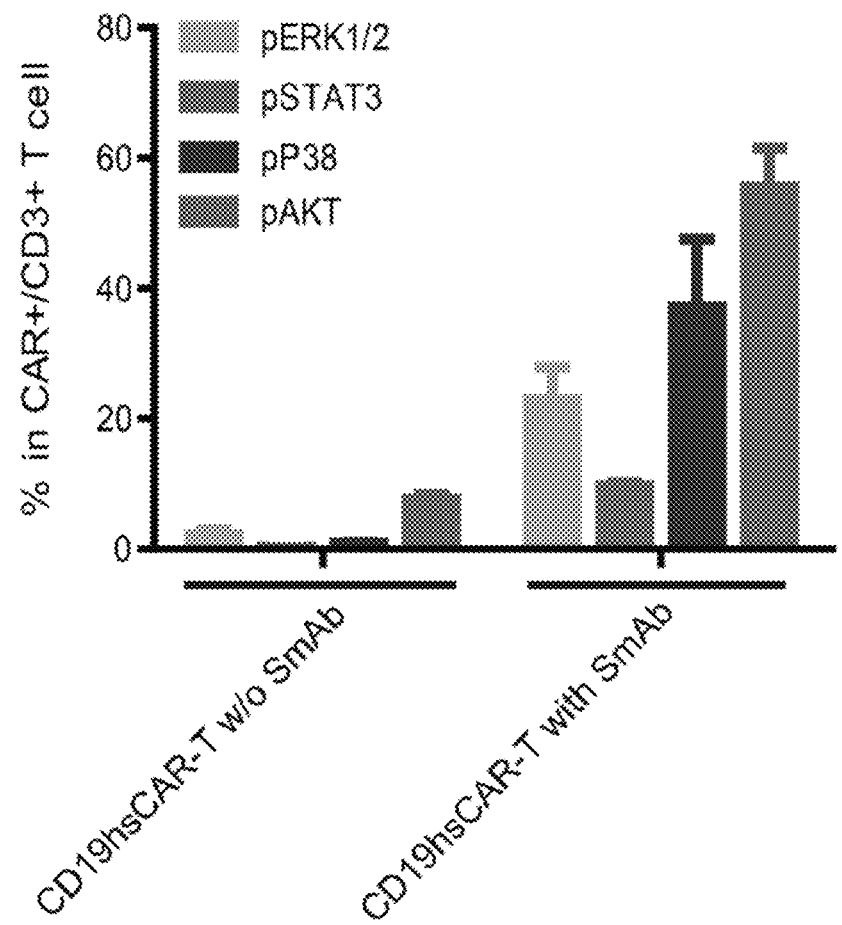
Figure 11G:
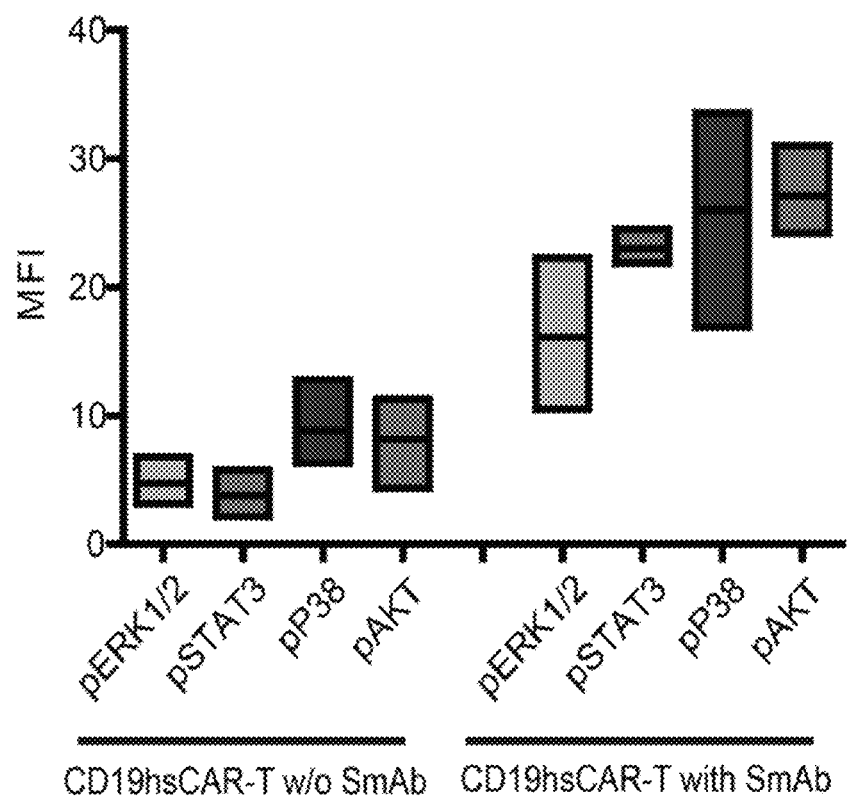
Figure 11H:
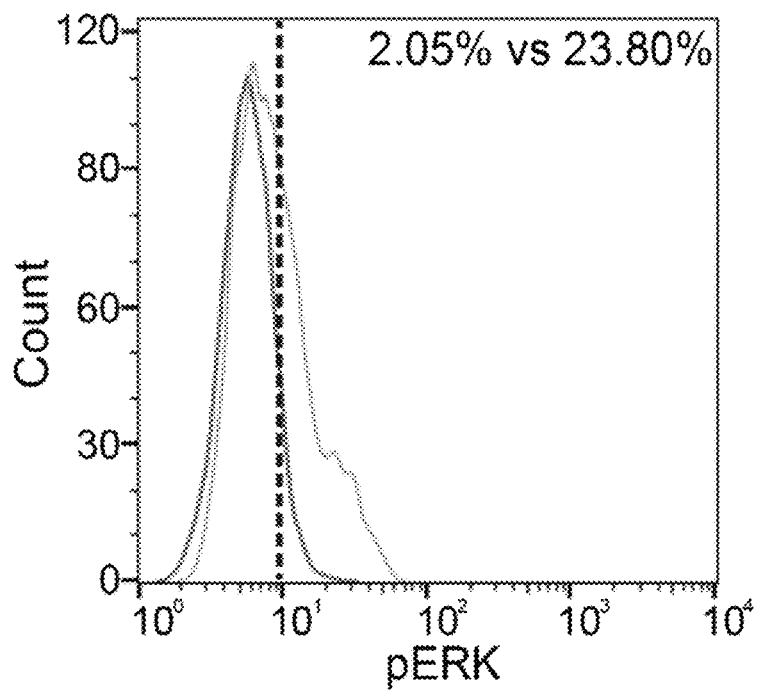
Figure 11I:
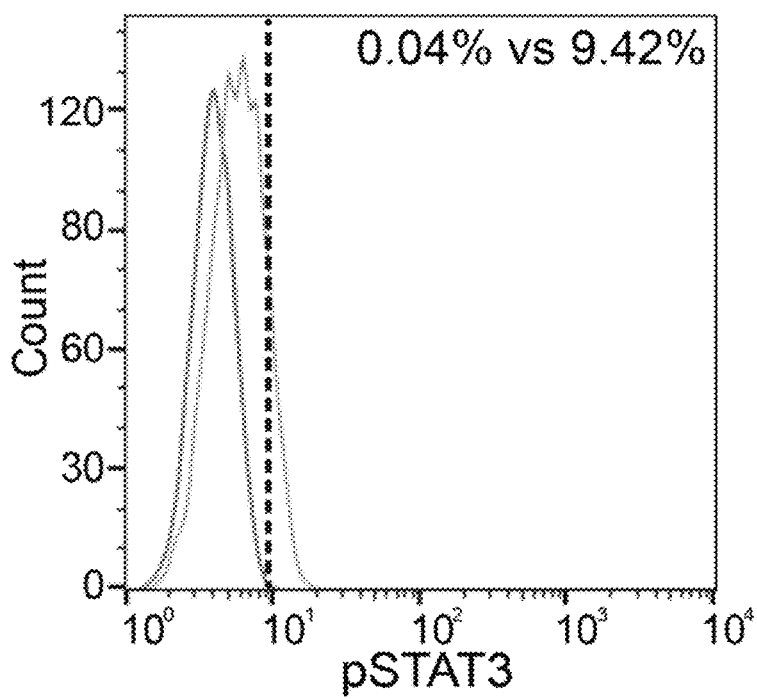
Figure 11J:
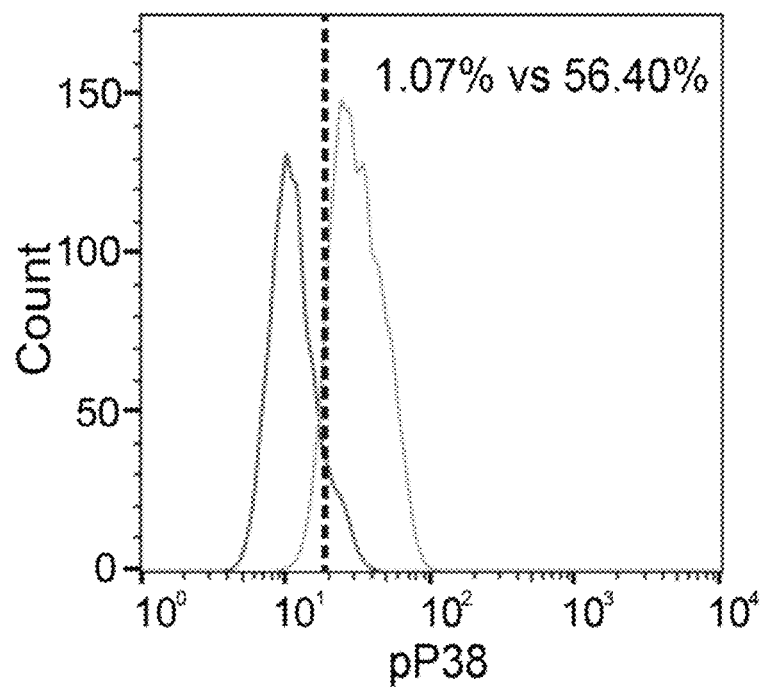
Figure 11K:
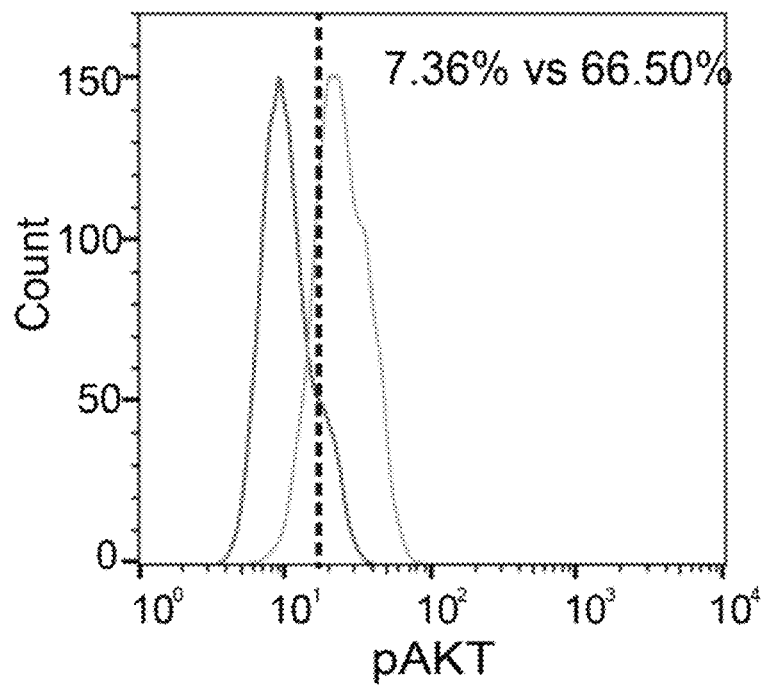
Figure 16B:
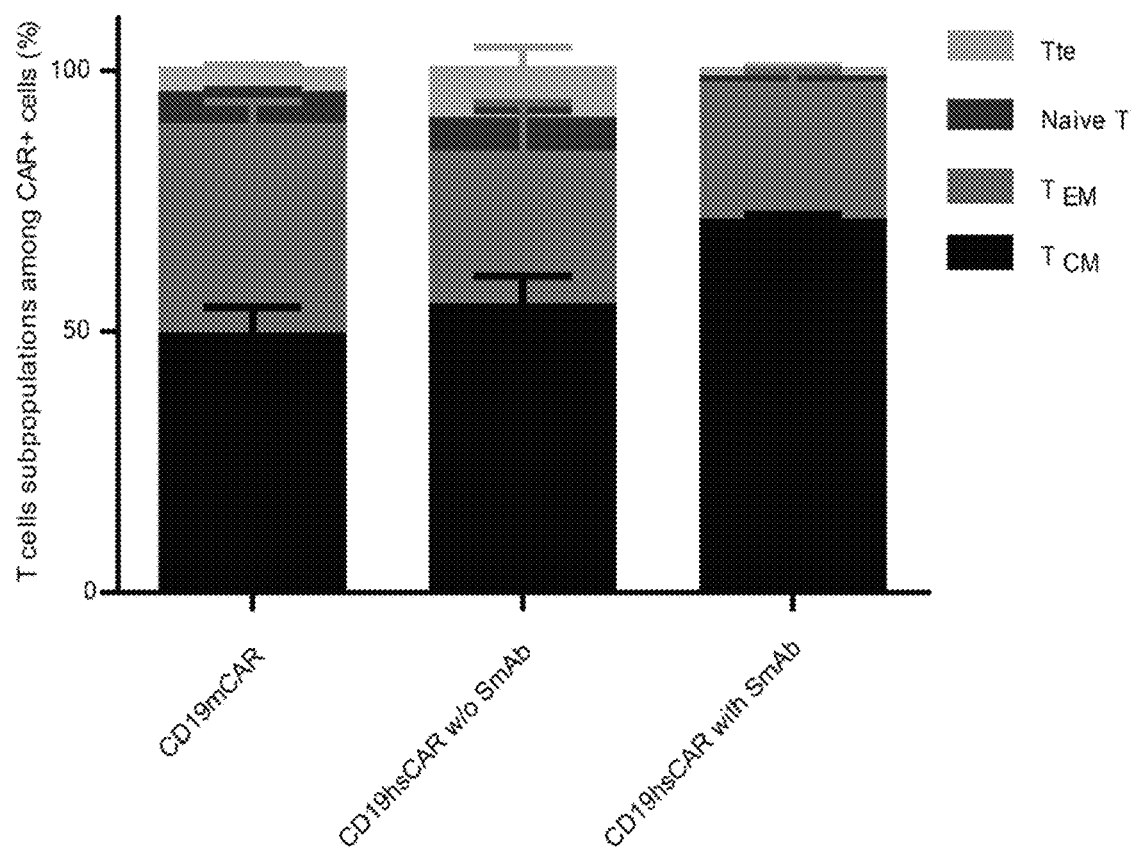
Figure 16C:
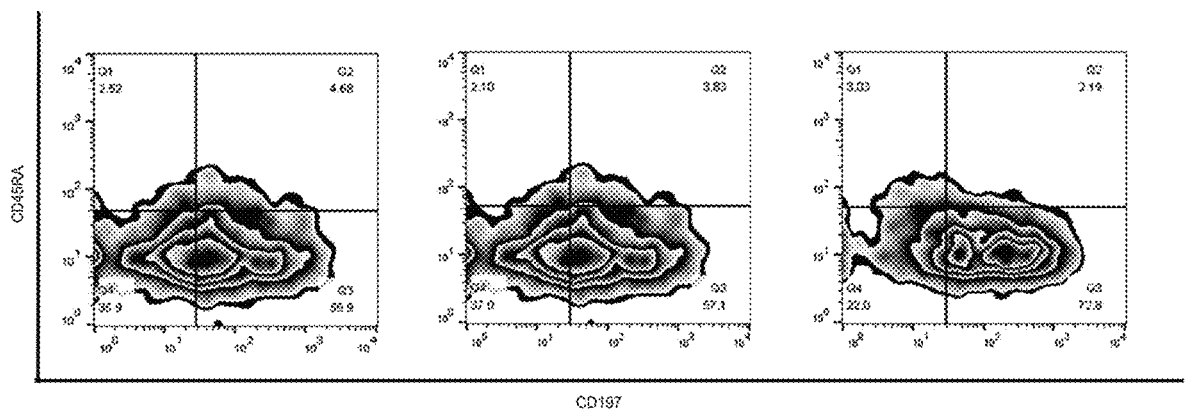

It was interesting to observe that prior activation with SmAb resulted in an improved cytotoxic function of T cells in vitro. We next examined whether such activation led to changes in proportions of T memory cell subpopulations. Compared with CD19 mCAR, and CD19 hsCAR w/o SmAb groups, exposure of CD19 hsCAR group to SmAb led to a greater proportion of central memory T (Tcm) cell subpopulation and a smaller proportion of effector memory T cell subpopulation (FIGS. 11C-11E). The proportions of each subpopulation among the CAR-positive cells were presented in FIGS. 16B-16C.

To investigate which downstream signaling pathways had contributed to the enlarged Tcm subpopulation, we examined various pathways, and found that ERK1/2, STAT3, P38, and AKT pathways were all activated by SmAb activation (FIGS. 11F-11K).

Improved Efficacy in Animal Studies

Figure 12A:
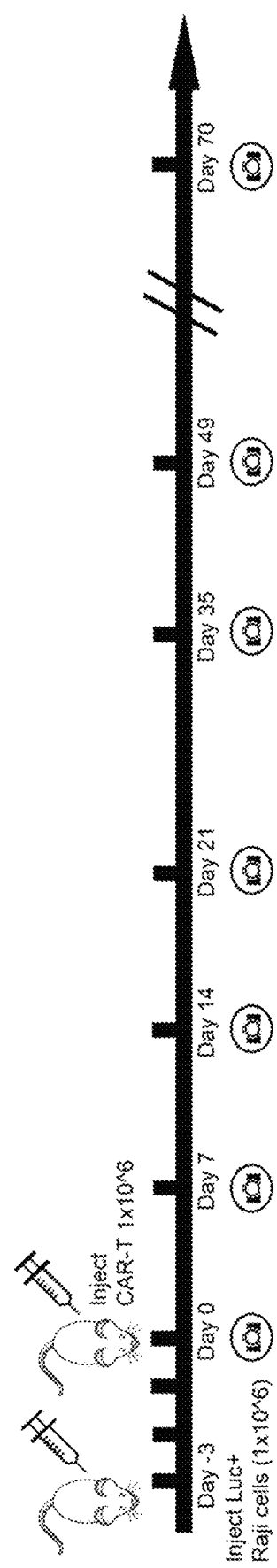
FIGS. 12A-12I show anti-tumor function mediated by CD19 hsCAR-T in vivo.
Figure 12B:
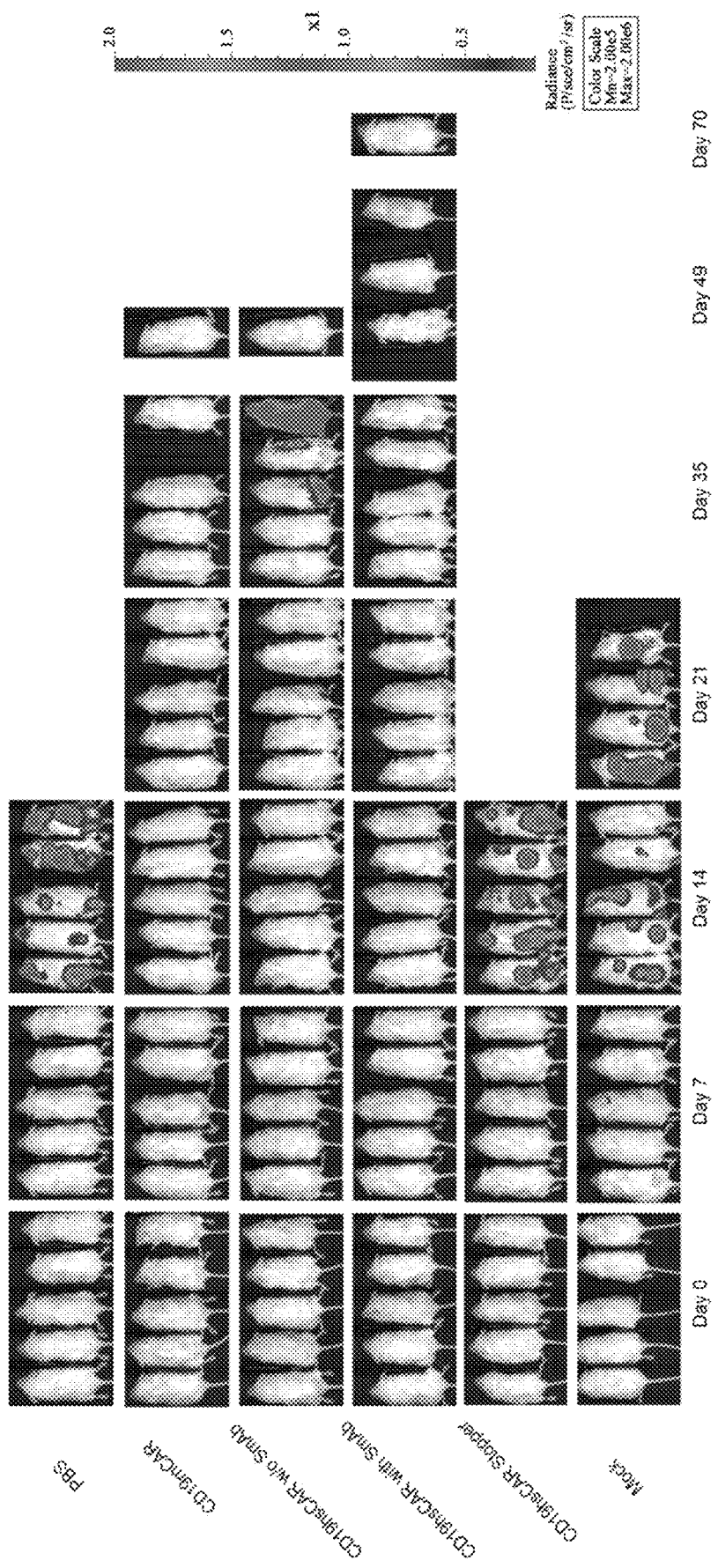
Figure 12C:
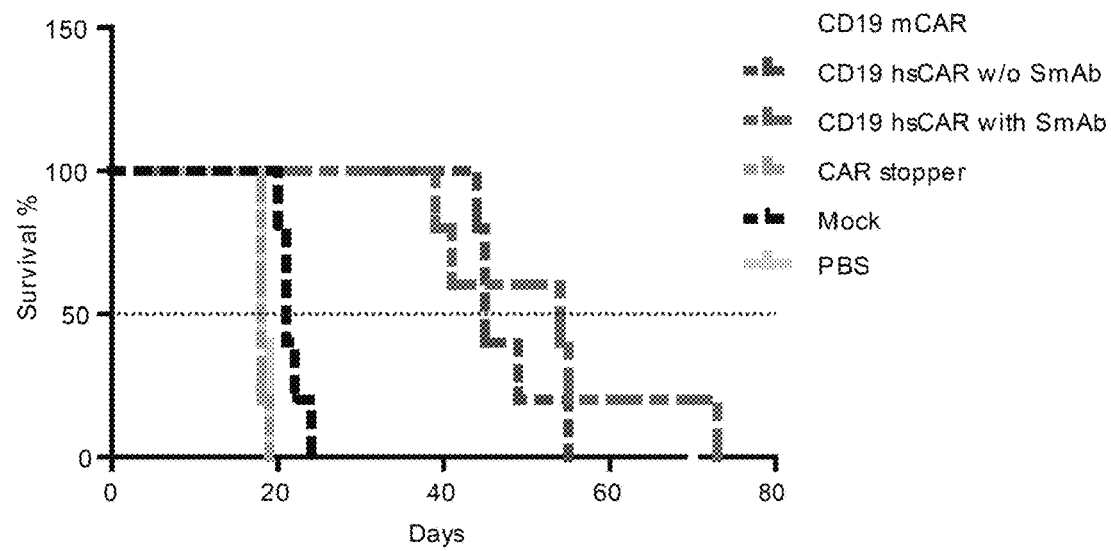
Figure 12D:
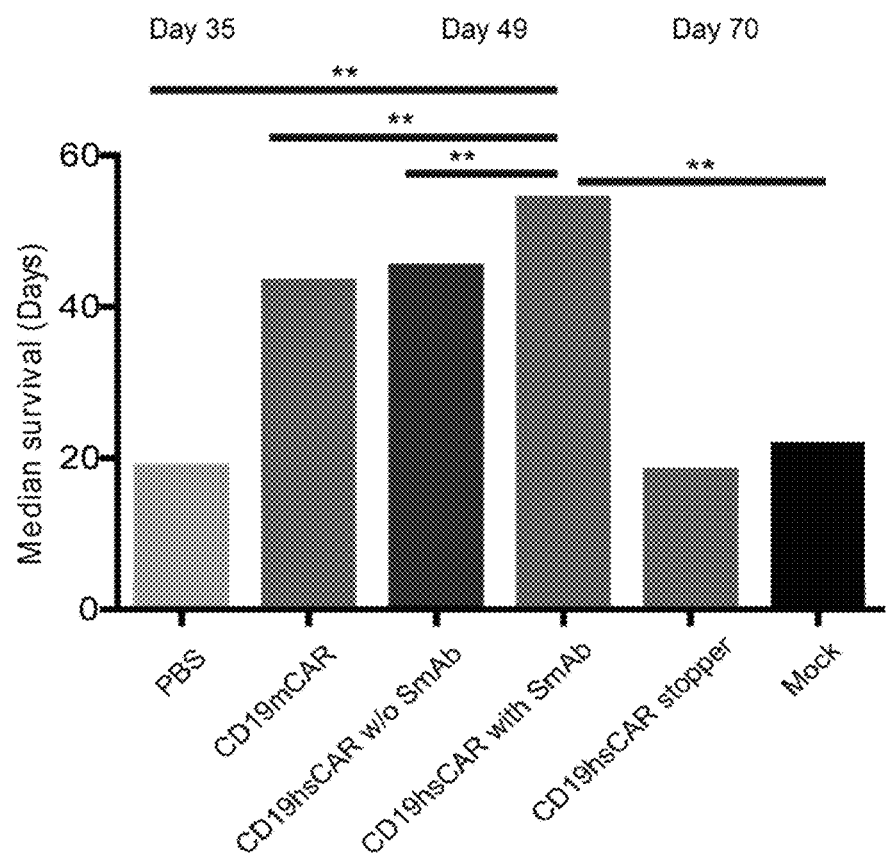
Figure 12E:
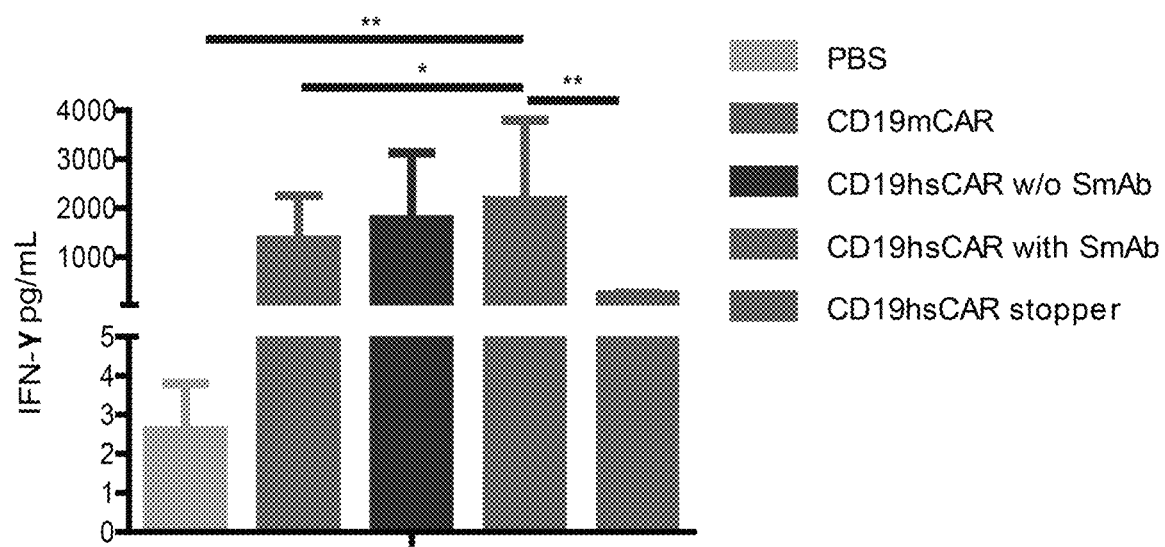
Figure 12F:
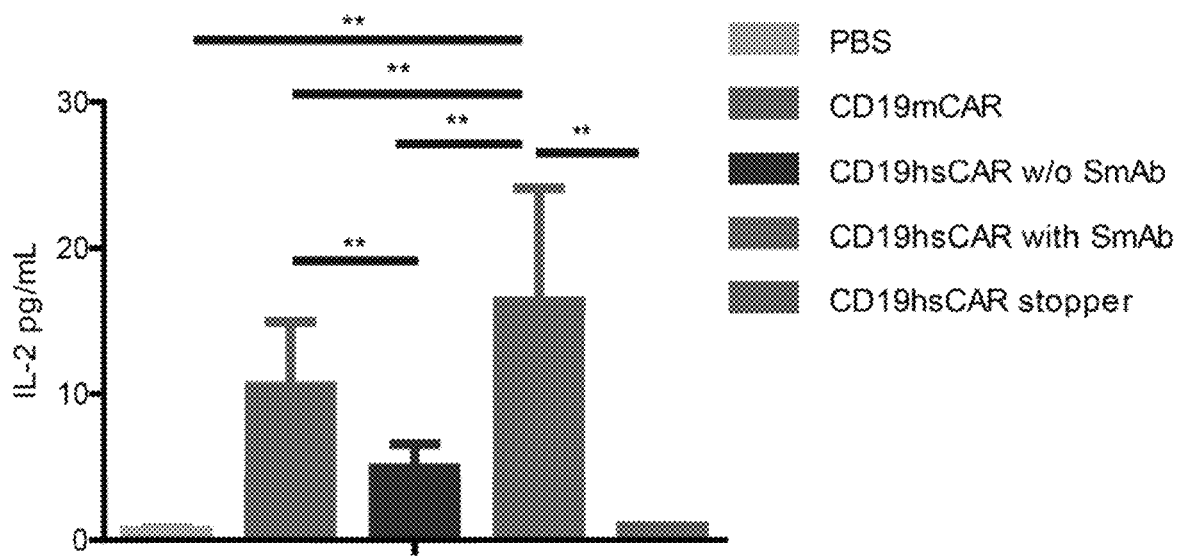
Figure 12G:
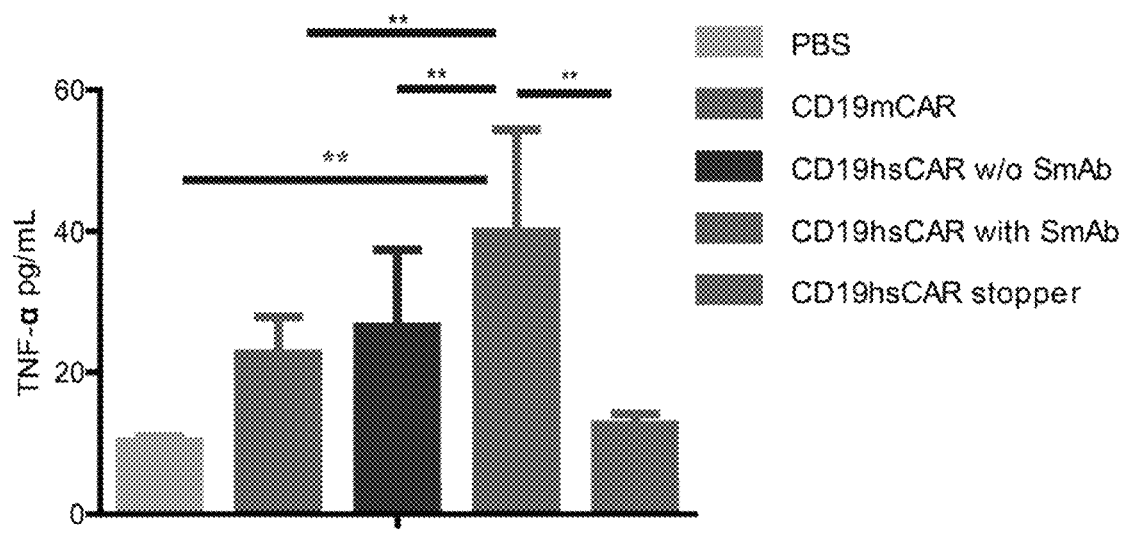
Figure 12H:
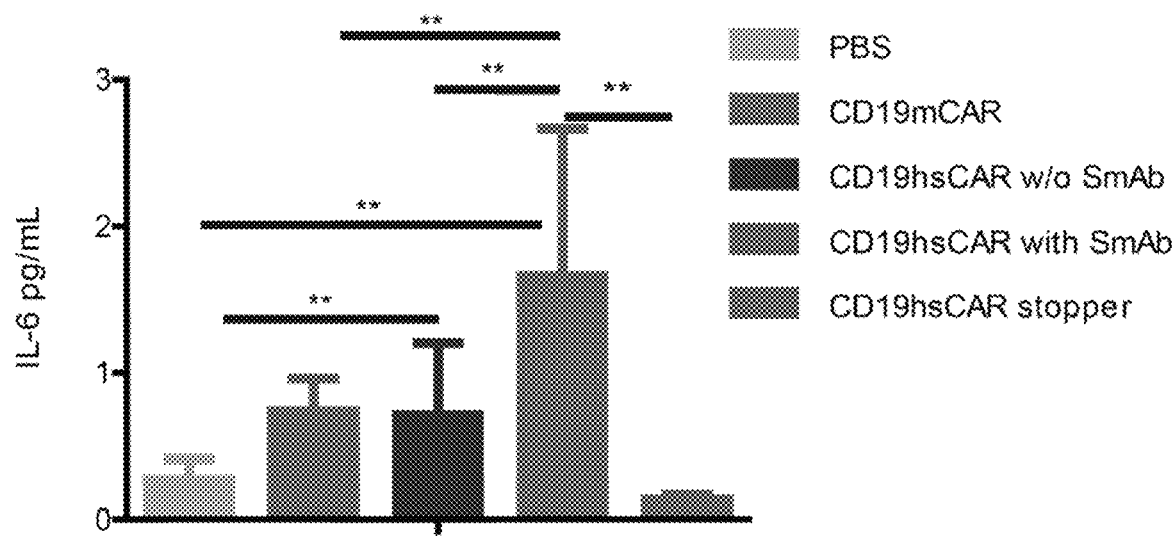
Figure 12I:
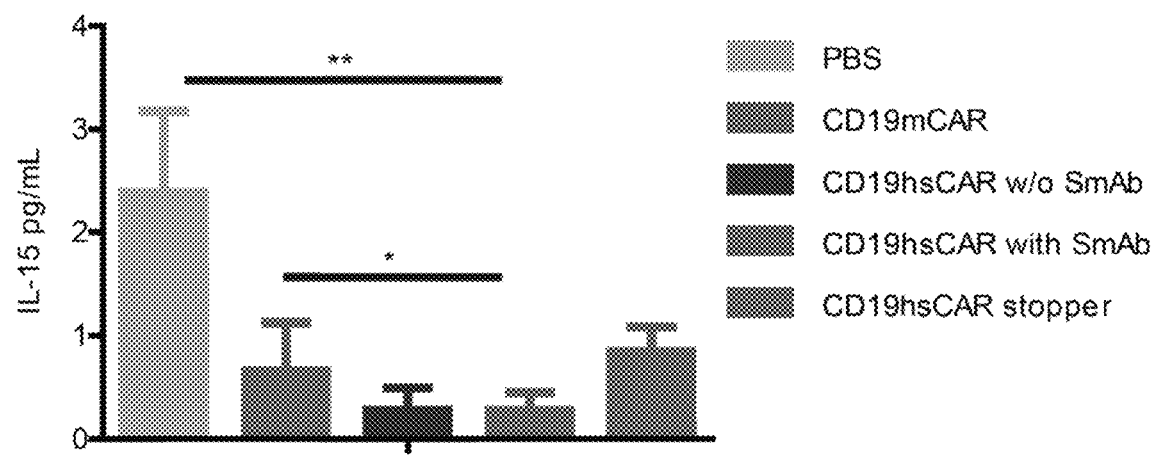
Figure 13A:
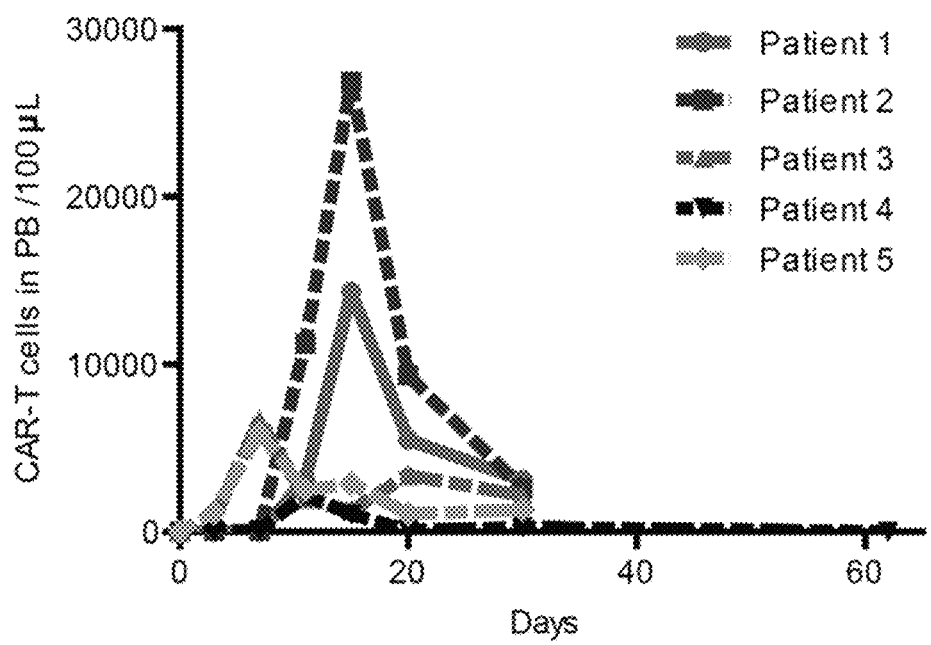
FIGS. 13A-13L show CD19 hsCAR-T cell engraftment, proliferation and persistence in patients.
Figure 13B:
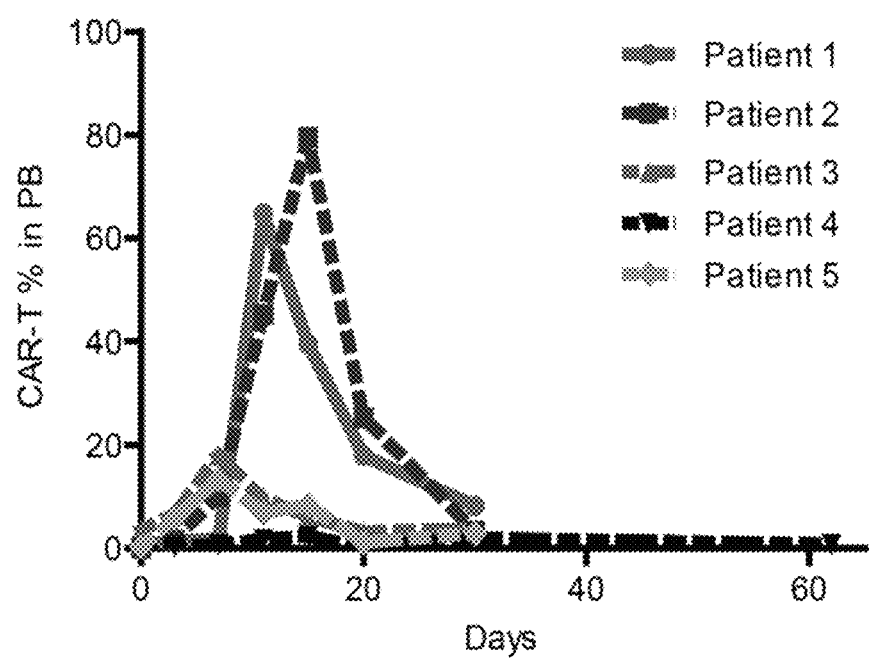
Figure 13C:
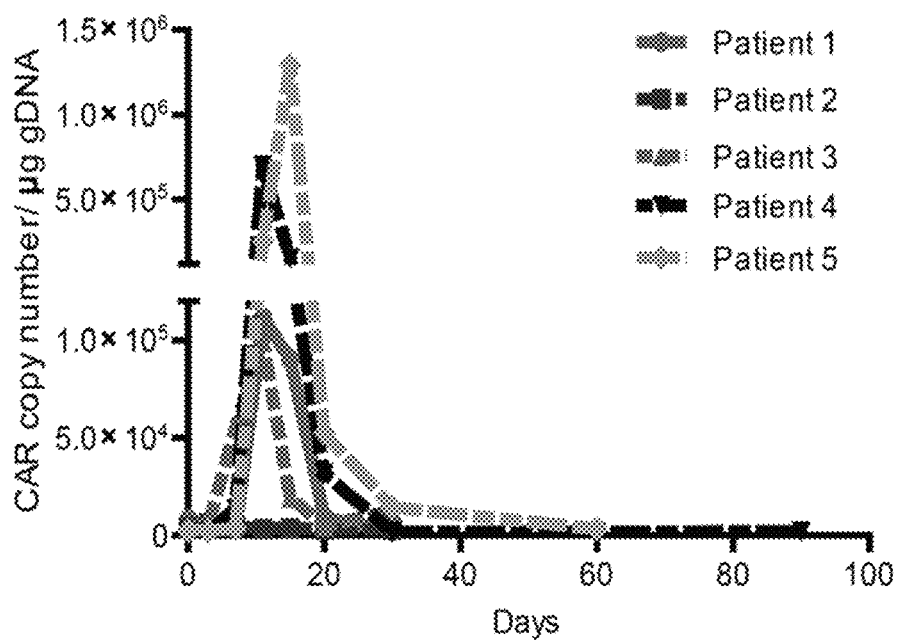
Figure 13D:
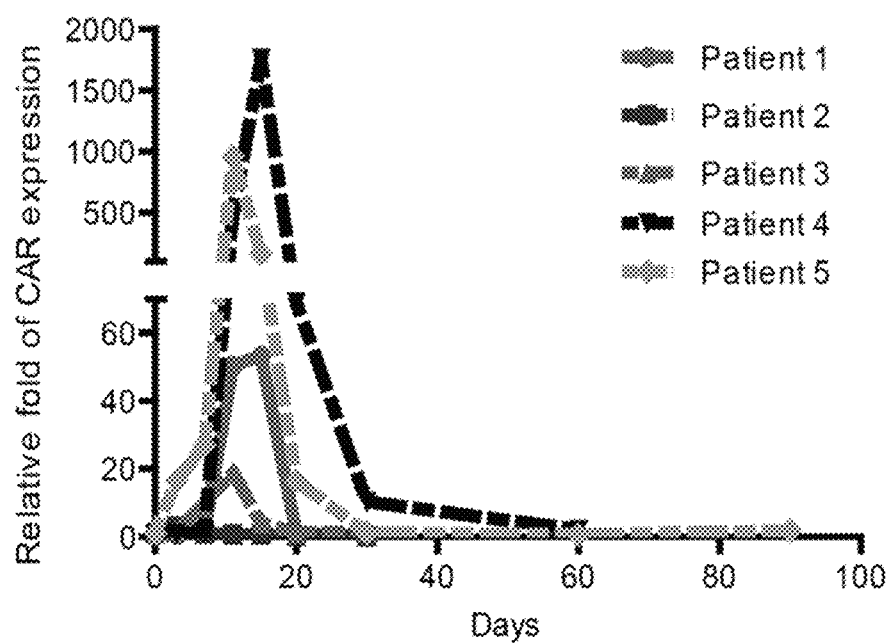
Figure 13E:
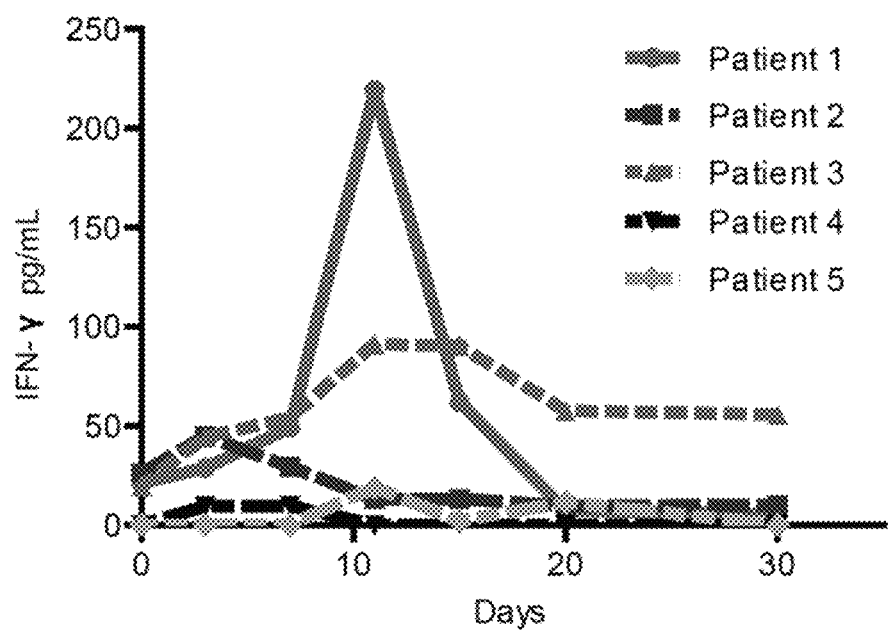
Figure 13F:
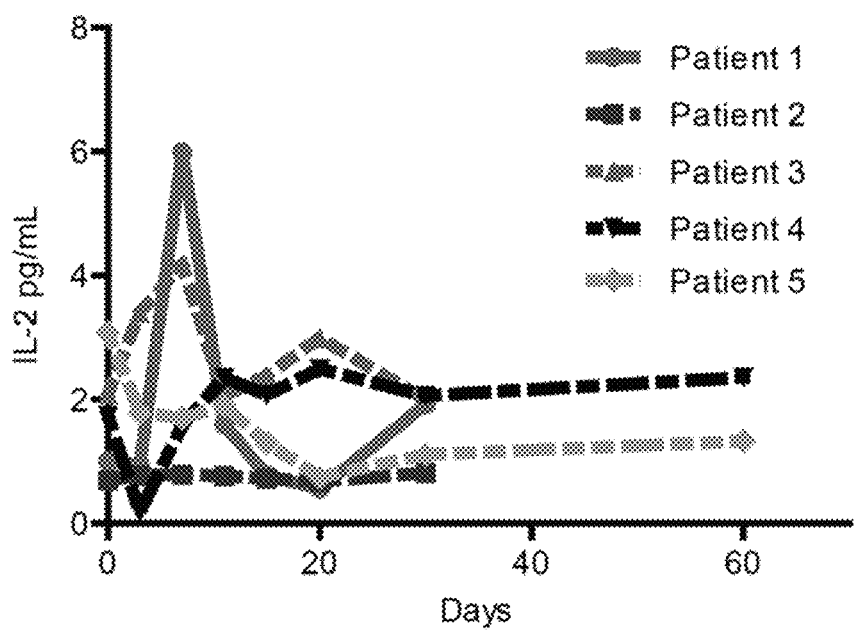
Figure 13G:
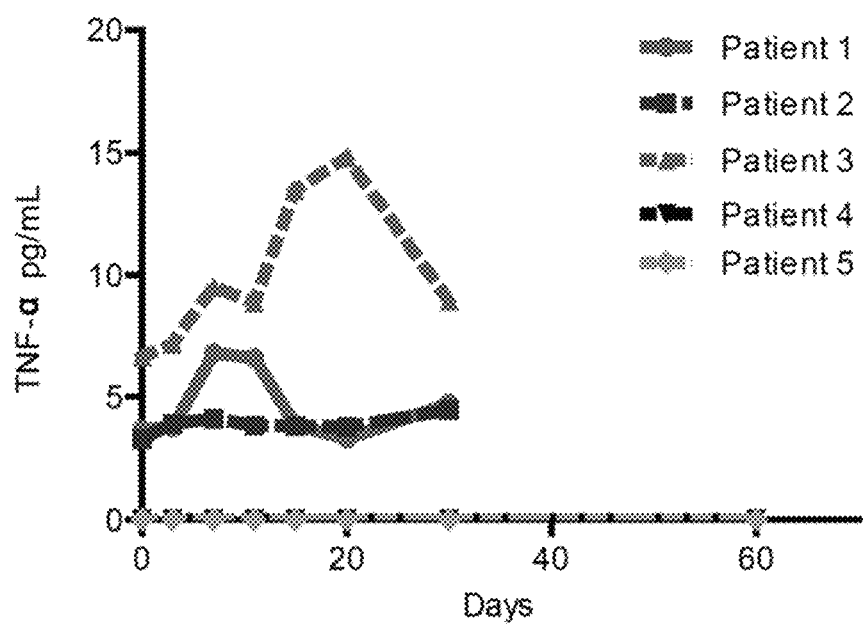
Figure 13H:
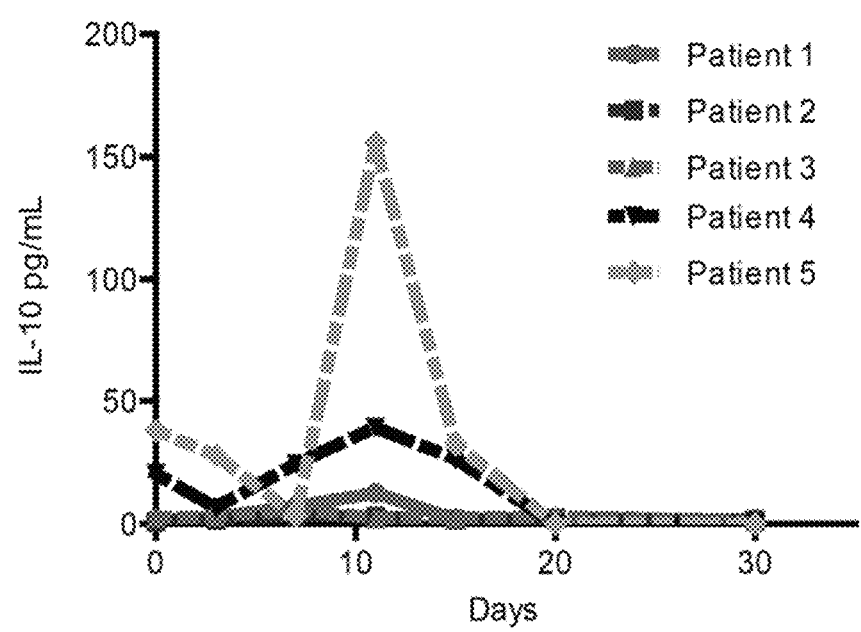
Figure 13I:
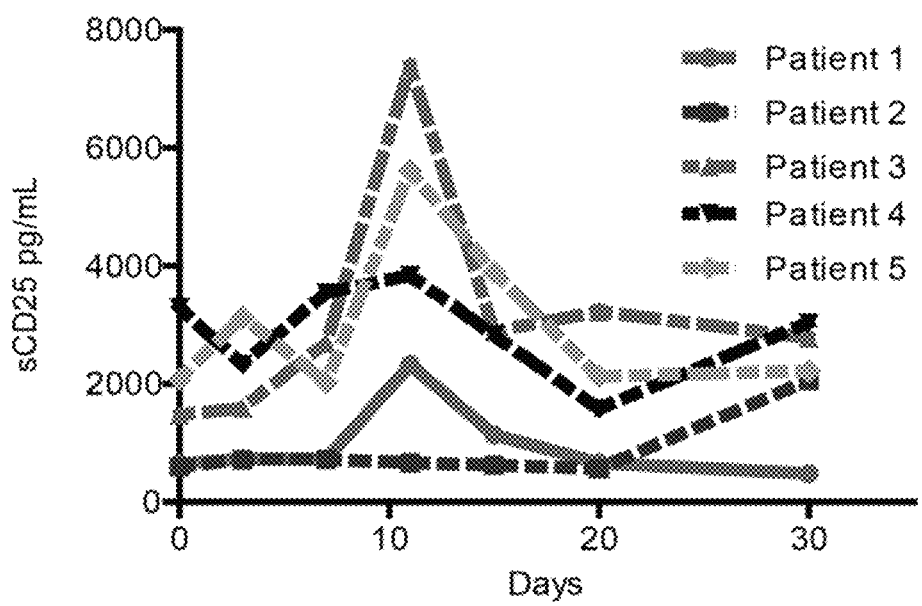
Figure 13J:
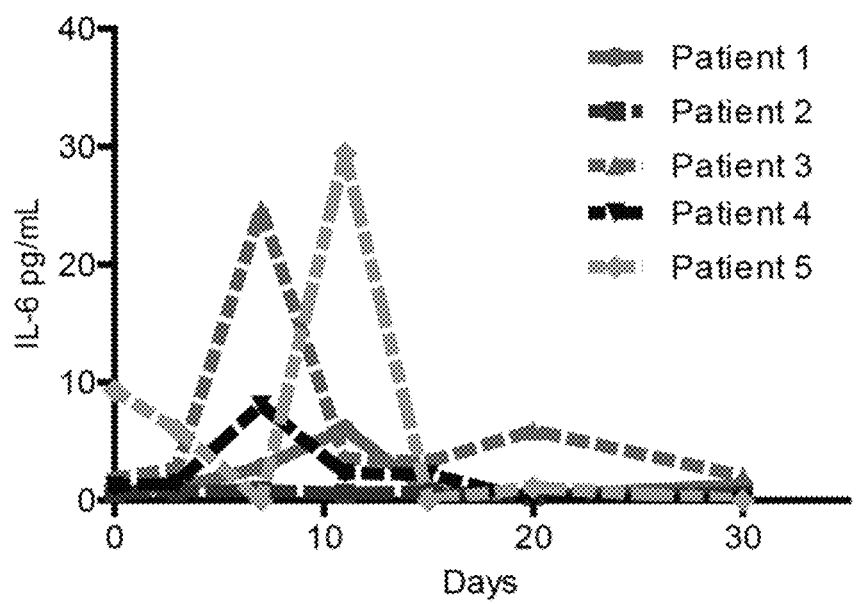
Figure 13K:
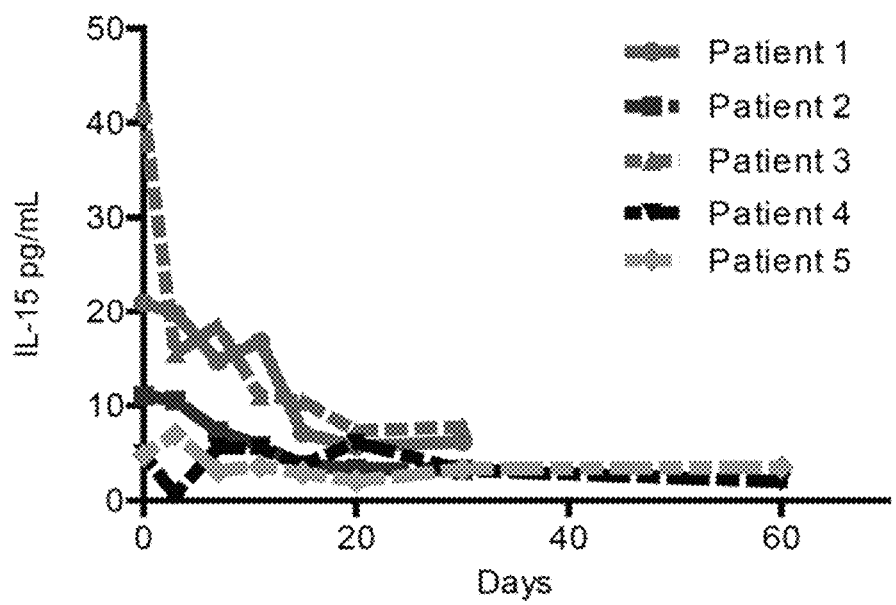
Figure 13L:
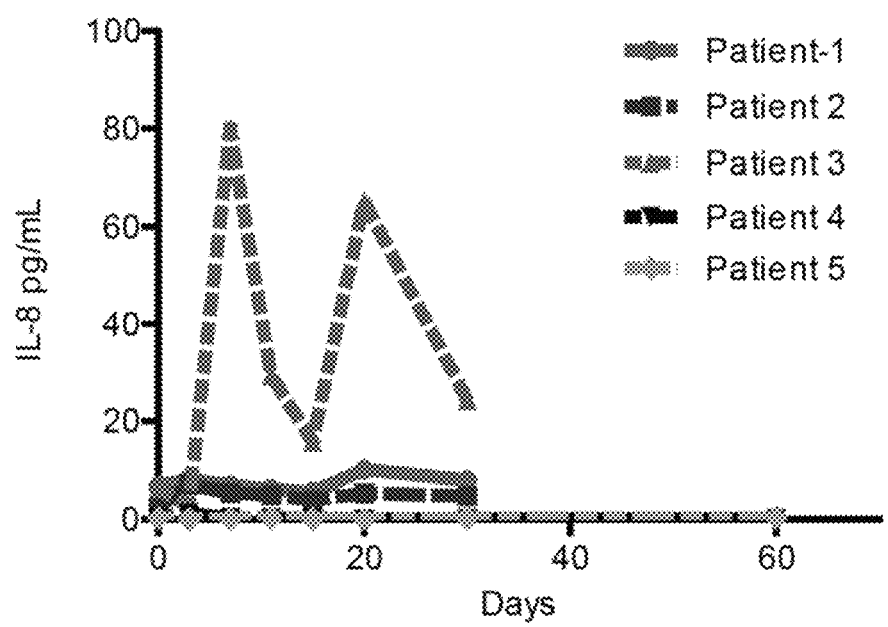
Figure 17:
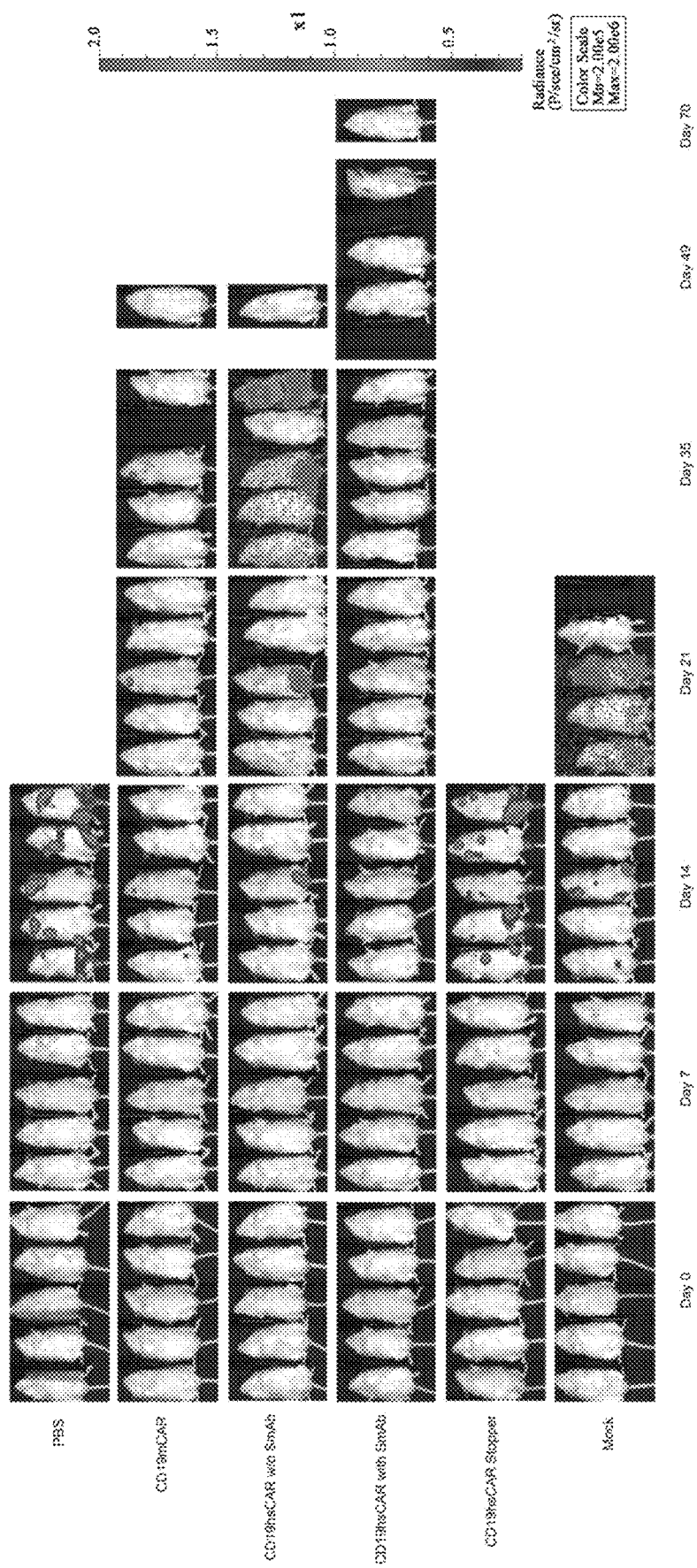
FIG. 17 shows bioluminescence imaging on the ventral side of animals treated by different CAR-engineered T cells.

Raji cells that expressed luciferase were i.v. infused into the immunodeficient mice (NOD/SCID IL2Ryc-/− NSG mice) to establish the leukemia mouse models. Normal healthy human PBMCs were used to generate various groups of CD19 CAR-T cells, which included mCAR, hsCAR, and a control hsCAR Stopper CAR (CD19 hsCAR lacking intracellular co-stimulation domain). PBS or each of the CAR-T group was i.v. infused into the leukemia mouse models 3 days after Raji cell injection. T cells engineered by lentiviral transduction of EGFP were used as a mock group. Tumor load and distribution were monitored prior to treatment and 7, 14, 21, 35, 49, and 70 days after treatment (FIG. 12A and FIG. 17). Mice treated with hsCAR-T cells activated with SmAb showed significantly longer survival than those with hsCAR-T cells w/o SmAb, and than those with mCAR-T cells (FIGS. 12B-12D). Analysis of mouse sera from 20 to 50 days post-treatment revealed a higher concentration of pro-inflammatory cytokines IFN-r, IL-2, IL-6, and a lower concentration of IL-15 (FIGS. 12E-12I).

Safety and Efficacy of hsCAR-T after Infusion to Patients with Previous Treatment of Murine CAR-T Cells Five refractory/relapsed B-ALL patients were included in the trial who had received previous murine CAR-T treatments and then relapsed with CD19-positive B lymphoblastic cells (Table 1 and Table 2). Patient 1 was a 9-year old male as in 2018, and showed symptoms of ALL in March 2017 and was diagnosed of B-ALL with a fusion genotype of E2A-HLF in September 2017. Patient 1 was refractory to chemotherapy (remained MRD+ and E2A-HLF+ after chemotherapy) and showed no central nervous system (CNS) involvement (treatment history listed in Table 2). In April, 2018, patient 1 received murine CD19 CAR-T therapy following lymphodepletion with treatment of Fludarabine (Flu), Cyclophosphamide (CTX) and Idarubicin (IDA). Seventeen days after murine CAR-T therapy, patient 1 achieved CMR; however, on day 30 after mCAR-T treatment, patient 1 relapsed with MRD. In May 2018, patient 1 received hsCAR-T therapy following lymphodepletion. Grade 1 CRS was observed after hsCAR-T treatment. On day 14, patient 1 achieved CMR (MDR−) and remained in CMR (MDR−) on day 28. Two months later, patient 1 received allo-HSC transplantation and remained in CMR as of the writing of the manuscript. This case proved the concept that humanized CAR-T cells may efficaciously treat patients who relapsed after murine CAR-T therapy.

remained MRD+ and E2A-HLF+ after intensive chemotherapy (Table 2). In November, 2017, this patient received CD19 mCAR-T infusion following lymphodepletion, and achieved CMR (MRD−) on day 15. Three and a half months after CD19 mCAR-T treatment, the patient relapsed with malignant B lymphoblastic cells positive for CD19 and CD22. In April, 2018, the patient received pooled CD19/CD22 mCAR-T cell infusion. However, the patient did not respond to the second time murine CAR-T treatment (NR), which did not reduce the tumor load in BM at any time point examined post-treatment and the disease remained progressive (lymphoblastic cells in BM: day 0 before infusion of the second time mCAR-T, 0.5% by morphology, 0.53% by flow cytometry, E2A-HLF fusion gene 0.94%; Day 15, 1.5% by morphology, 0.6% by flow cytometry, E2A-HLF fusion gene 13.3%; Day 36, 30% by morphology, 46.81% by flow

TABLE 1

Patients and clinical responses after CD19hsCAR-T treatment

| Patient No. | | | 1 | | 2 | | 3 | | 4[$] | 5[$$] |
|---|---|---|---|---|---|---|---|---|---|---|
| Age | | | 9 | | 14 | | 17 | | 14 | 20 |
| Sex | | | M | | M | | M | | F | F |
| Complex chromosome | | | N | | Y | | N | | N | Y |
| Gene fusion | | | E2A-HLF | | E2A-HLF | | BCR-ABL1 | | MLL/ITD | MLL/ITD |
| Prior | CAR resource | | murine | | murine | | murine | | murine | murine |
| CAR-T | Target | | CD19 + CD22 | CD19 | CD19 + CD22 | CD19 | CD19 | CD19 | CD19 | CD19  CD19 |
| therapies | Infusion dosage ×10$^6$/kg | | 0.3 | 0.3 | 0.3 | | 4 | 0.3 | 1 | 1  1 |
| Relapsed after infusions (Months) | | | 1 | 3.5 | NR | | 8 | 1 | N/A* | NR  N/A* |
| Before | BM (morphology)% | | 4 | | 46 | | 0.02 | | 29 | 6 |
| CD19 | BM (flow cytometry)% | | 2.28 | | 34.86 | | 0 | | 15.31 | 34.74 |
| hsCAR-T | CSF % | | 0 | | 0 | | 66.13 | | 0 | 0 |
| therapy | Pre-B in PB % | | 0 | | 0 | | 0 | | 0 | 0 |
| Infusion Dosage ×10$^6$/kg | | | 1 | | 0.3 | | 1 | | 3 | 3 |
| After | BM (morphology)% | Day 15 | 0 | | 10.5 | | 0 | | 0 | 0 |
| CD19 | BM (flow cytometry)% | | 0 | | 14.98 | | 0 | | 0 | 0 |
| hsCAR-T | CSF % | | 0 | | 0 | | 0 | | 0 | 0 |
| therapy | Pre-B in PB % | | 0 | | 0 | | 0 | | 0 | 0 |
| | BM (morphology)% | Day 30 | 0 | | 82 | | 0 | | 0 | 0 |
| | BM (flow cytometry)% | | 0 | | 71.84 | | 0 | | 0 | 0 |
| | CSF % | | 0 | | 0 | | 0 | | 0 | 0 |
| | Pre-B in PB % | | 0 | | 0 | | 0 | | 0 | 0 |
| CRS | Grade | | 1 | | 1 | | 1 | | 1 | 1 |
| | Tocili | | N | | N | | N | | N | N |
| | Neurotoxicity | | N | | N | | N | | N | N |
| Response at 1 month | | | CMR, MRD− | | NR | | CMR, MRD− | | CMR, MRD− | CMR, MRD− |
| Follow up | | | Underwent allo-HSCT after 2 months | | Off case | | Relapsed on day 63 | | CMR for 3 month** | CMR for 2 months** |

Note:
allo-HSCT, allogeneic hematopoietic stem cell transplantation;
BM, bone marrow;
CD19hsCAR-T, chimeric antigen receptor T cell engineered with humanized selective CD19-spesific scFv;
CMR, complete molecular remission;
CRS, cytokine release syndrome;
CSF, Cerebrospinal fluid;
ITD: internal tandem duplication;
M, male;
mCAR-T, chimeric antigen receptor T cell engineered with murine-based CD19-specific scFv;
MRD, minimal residue disease;
N, no;
NR, no remission;
PB, peripheral blood;
Tocili, tocilizumab;
Y, yes;
[$]Patient 4 harbors gene mutations, including IKZF1 mutation, ERG (Δ3-9 positive), FANCD2 (C2080 G > A pD694N), NRAS (G13D) and JAK (I668F);
[$$]Patient 5 harbors gene mutations, includingIKZF1 mutation, ERG (Δ3-9 positive) and NRAS (G13D);
*Patient 4 and patient 5 received murine-based CD19CAR-T bridging toHSCT. Patients4 and 5 underwent CD19 hsCAR-T treatmentwhen they relapsed 1.5 years and 1 year after HSCT, respectively;
**Patient 4 and patient 5 remained in CMR when the manuscript was prepared.

Figure 14A:
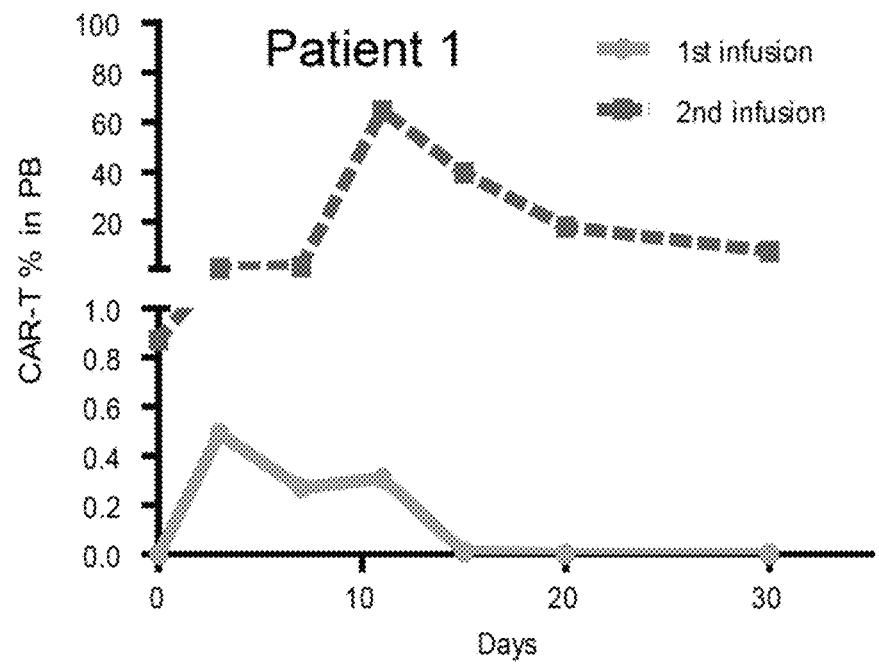
FIGS. 14A-14J show proliferation of CD19 hsCAR-T cells in five patients who had relapsed after mCAR-T treatments, where comparisons of proliferation and persistence of murine-based CD19 CAR-T vs. CD19 hsCAR-T in five patients who sequentially received mCAR-T and hsCAR-T treatments were made.
Figure 14B:
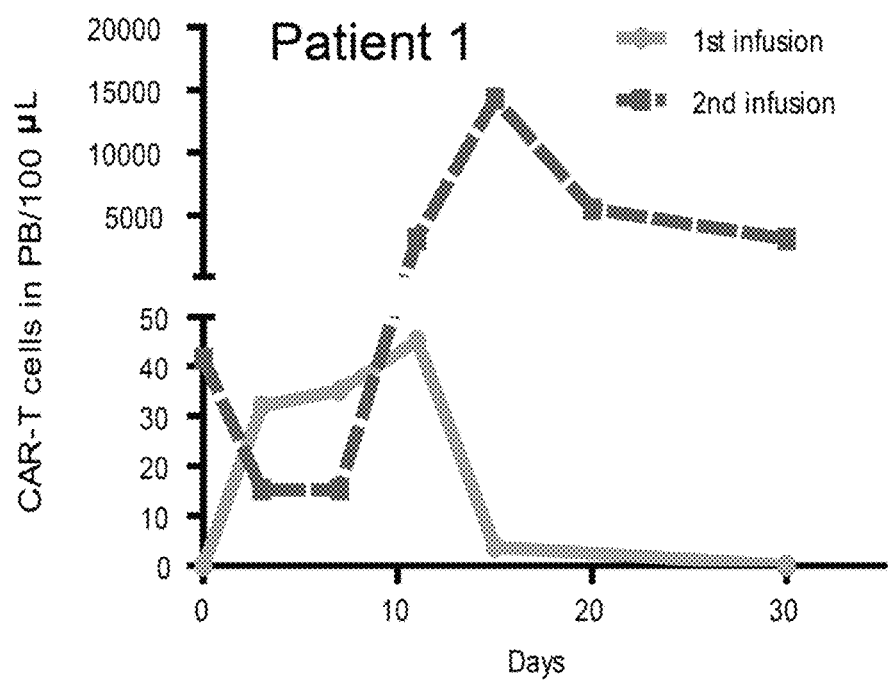
Figure 14C:
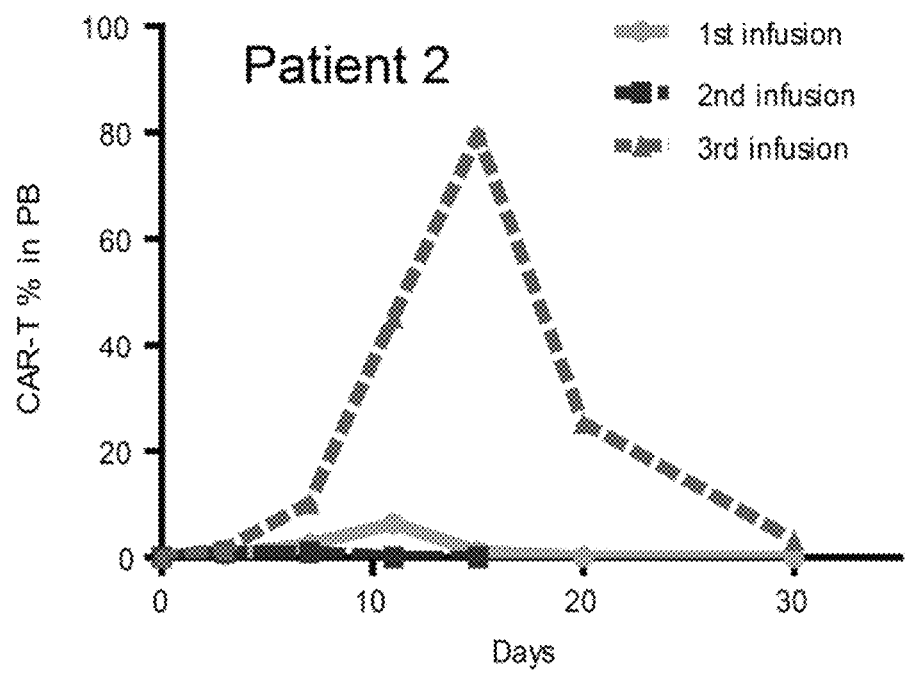

Patient 2 was a 14-year old male patient as in 2018, and, in June 2017, he was diagnosed of B-ALL with a fusion genotype E2A-HLF and a complex chromosome karyotype. This patient was also refractory to chemotherapy and cytometry, E2A-HLF fusion gene 119.58%). In May, 2018, patient 2 received CD19 hsCAR-T treatment (Table 1 and Table 2). Considering the high tumor load, the dosage of hsCAR-T cells was lowered to 0.3×10$^6$/kg body weight, to avoid the possible side effect of severe cytokines release syndromes (CRS). On day 0 prior to hsCAR-T infusion (after lymphodepleting conditioning), the tumor loads in the bone marrow was 36% according to morphology evaluation, and 34.86% by flow cytometry. On day 15 post-treatment, tumor loads in BM evaluated by morphology and flow cytometry were reduced to 10.5% and 14.98%, respectively; B cell percentage in PB was also brought down to almost zero on day 15 (FIG. 18B); but on day 30, the tumor loads in BM bounced back to 82% (morphology), and 71.84% (flow cytometry), respectively. The results suggested that hsCAR-T cells might have been effective but exhausted after day 15 due to the low dosage infused and the relative high tumor load. Indeed, the proportion of hsCAR-T cells in PB was brought down sharply after day 15 and they almost disappeared on day 30 (FIG. 14C). Unfortunately, when we were trying to infuse hsCAR-T cells for another time with a higher dosage, patient 2 quit the trial by some unknown reasons.

TABLE 2

Previous therapies for the five patients

| Patient No. | Previous therapies |
|---|---|
| Patient 1 | Chemotherapy following the protocols of VDLD and CAM |
| | Chemotherapy with MTX, Dex and L-asp |
| | Chemotherapy with FLU, IDA and CTX |
| | CD19/CD22 mCAR-T ($0.3 \times 10^6$/kg) |
| Patient 2 | Chemotherapy with FLU, CTX and VLP |
| | CD19 mCAR-T ($0.3 \times 10^6$/kg) |
| | CD19/CD22 mCAR-T ($0.3 \times 10^6$/kg) |
| Patient 3 | Chemotherapy with VCR, NDR, L-aps and prednisone |
| | Gleevce by oral administration |
| | Chemotherapy with Ara-C |
| | Intrathecal chemotherapy with Ara-C, Dex and Methotrexate |
| | Chemotherapy with MTX and L-aps, combined with oral administration of Dasatinib |
| | Chemotherapy with IDA, Dex, and L-asp |
| | Haploidentical allo-HSCT (mother as donor) |
| | CD19 mCAR-T × 2 times ($4 \times 10^6$/kg and $0.3 \times 10^6$/kg) |
| | Haploidentical allo-NK infusion × 5 times |
| Patient 4 | Chemotherapy with prednisone, CTX, Ara-C, THP, Dex, L-asp, DNR and Acta |
| | CD19 mCAR-T ($1 \times 10^6$/kg) |
| | HLA-identical allo-HSCT (sister as donor) |
| | HLA-identical allo-NK infusion × 2 times |
| Patient 5 | Chemotherapy with CODP (CTX, VDS, DNR and Dex) |
| | Chemotherapy with Hyper-CVAD/B (MTX and Ara-C) |
| | Chemotherapy with VP (VDS and Dex) |
| | Chemotherapy with Hyper-CVA D/B (MTX and Ara-C) |
| | Chemotherapy with Hyper-CVAD/A (CTX, VDS, EPI and Dex) |
| | Chemotherapy with VDLP (VDS, DNR, L-asp and Dex) |
| | CD19 mCAR-T × 2 times ($1 \times 10^6$/kg) |
| | Haploidentical allo-HSCT (father as donor) |

Note:
Ara-C, cytarabine;
allo-HSCT, allogeneic hematopoietic stem cell transplantation;
CAM, complementary and alternative medicine;
CTX, cyclophosphamide;
Dex, Dexamethasone;
FLU, Fludarabine;
IDA, Idarubicin;
L-asp, L-asparaginase;
MTX, Methotrexate;
VDLD: VCR, daunorubicin or doxorubicin, L-asparaginase, and prednisone or dexamethasone;
VLP, ventriculolumbar perfusion chemotherapy.

Patient 3 was a 17-year old male patient as in 2018, and was diagnosed of B-ALL with a fusion genotype BCR-ABL1 in the end of 2014. He had an extramedullary disease with CNS involvement, and received targeted therapy (Imatinib followed by Dasatinib) and chemotherapy. After achieving CMR, the patient underwent haploidentical HSC transplantation from his mother as donor in May, 2015. In June, 2017, patient 3 relapsed with extramedullary disease with CNS involvement with a tumor load of 8.96% in the cerebral spinal fluid (CSF). In August, 2017, patient 3 received CD19 mCAR-T treatment following intrathecal chemotherapy, and achieved CMR after experiencing grade 3 CRS and neurotoxicity. In December, 2017 and January, 2018, patient 3 received 5 times natural killer cell treatments. In March, 2018, patient 3 received another CD19 mCAR-T as a preventive measure (at this time, the patient had not relapsed). In late April, 29 days after the second time mCAR-T treatment, the patient relapsed with 66.13% lymphoblastic cells of the recipient origin in CSF and 0.02% in bone marrow (evaluated by morphology). It was unclear whether the relapse was only a coincidence, or subsequent murine CAR-T treatment had facilitated the relapse. In June, patient 3 received CD19 hsCAR-T treatment following intrathecal chemotherapy and lymphodepleting conditioning. On day 5, the patient experienced grade 1 CRS. On day 15, CMR (MRD−) was achieved in BM, PB, and the CNS (Tables 1-2). On day 63, the patient relapsed with extramedullary disease with CNS involvement and received another haploidentical HSC transplantation from his father as donor.

Patient 4 was a 14-year old female as in 2018, and was diagnosed of B-ALL in 2016. She achieved CR after receiving the first round of chemotherapy in July, 2016, but relapsed in one month and remained refractory to chemotherapy thereafter. Patient 4 received CD19 mCAR-T treatment in November, 2016 and achieved CR. In January, 2017, the patient was administered HLA-identical HSC transplantation from her sister as donor. In August, 2018, she relapsed and received CD19 hsCAR-T treatment in September, 2018 (Tables 1-2); the patient remained in CMR as of the writing of the manuscript.

Patient 5 was a 21-year old female as in 2018, and was diagnosed of B-ALL in 2016. Similar to patient 4, patient 5 received chemotherapy in July, 2016, achieved CR, but relapsed in about one month. Patient 5 remained refractory to chemotherapy thereafter, and received CD19 mCAR-T treatment in June, 2017. On day 43 post-treatment, evaluation showed that the patient did not achieve CR, and received the second mCAR-T treatment on the same day (Day 43), which led to a CR. In September, 2017, patient 5 received haploidentical HSC transplantation from her father as donor. In September, 2018, she relapsed and received CD19 hsCAR-T treatment in October, 2018. This patient remained in CMR as of the writing (Tables 1-2).

Figure 18A:
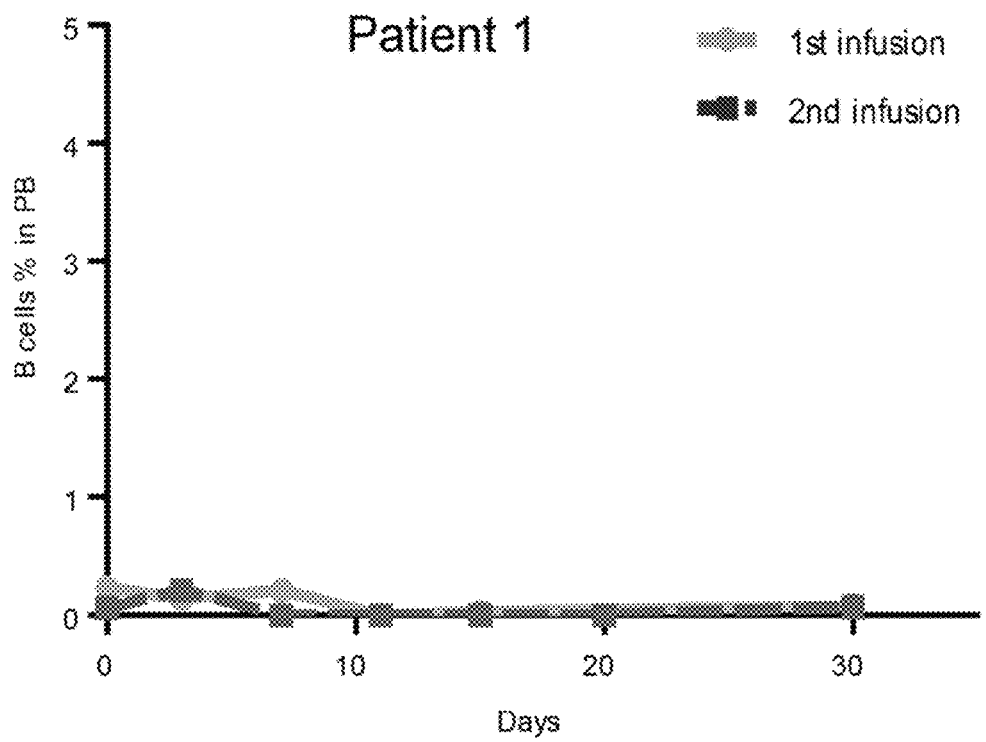
FIGS. 18A-18E show comparison of CD19+ B cell percentages before and after murine-based CD19 CAR-T and subsequent CD19 hsCAR-T infusions in the peripheral blood of Patients 1 to 5. CD19+ B cells were detected by flow cytometry at the indicated time points.
Figure 18B:
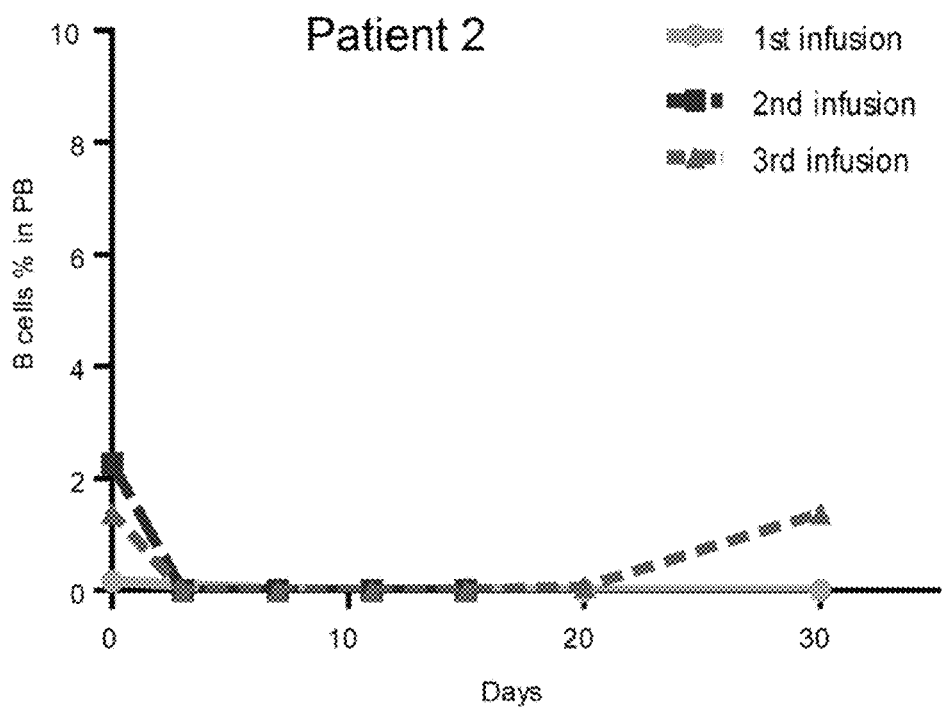
Figure 18C:
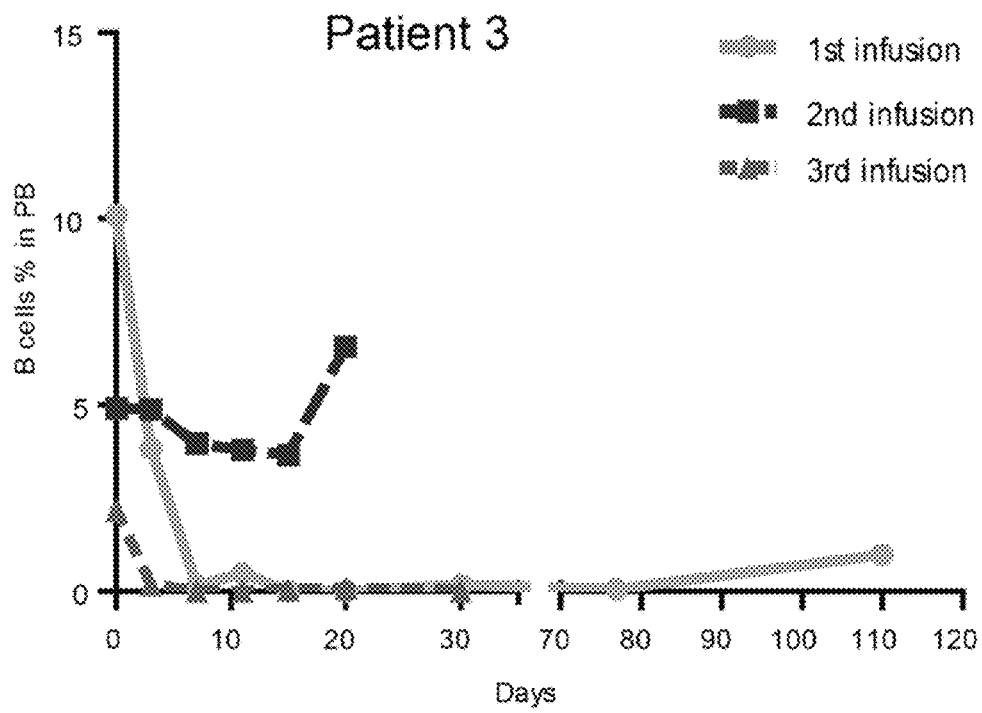
Figure 18D:
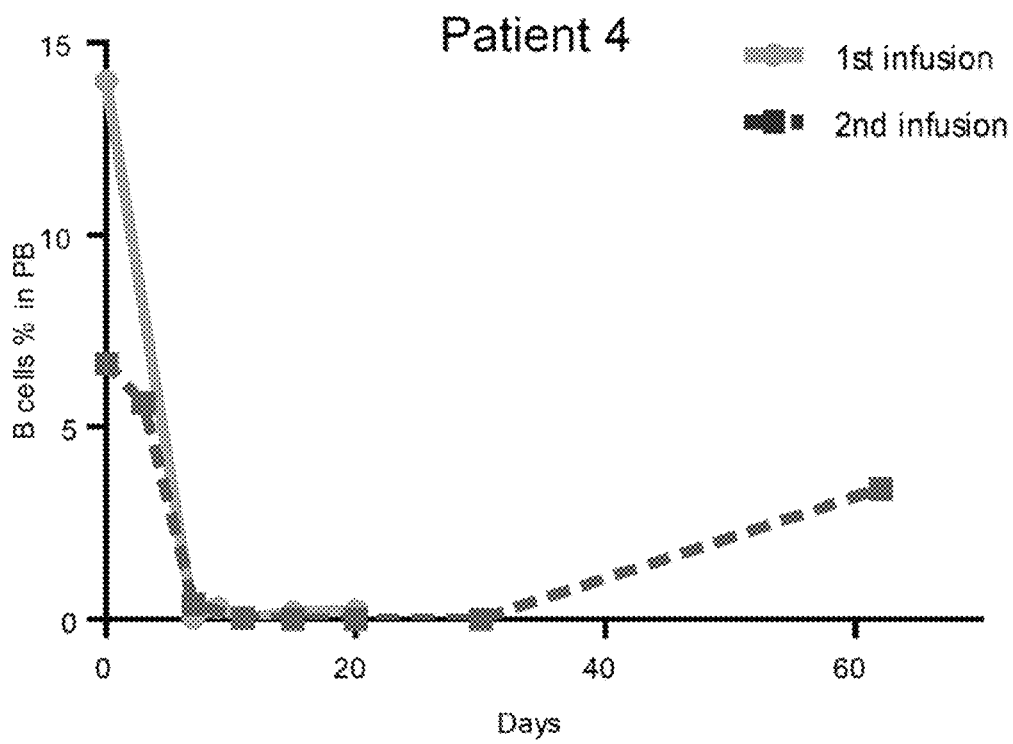
Figure 18E:
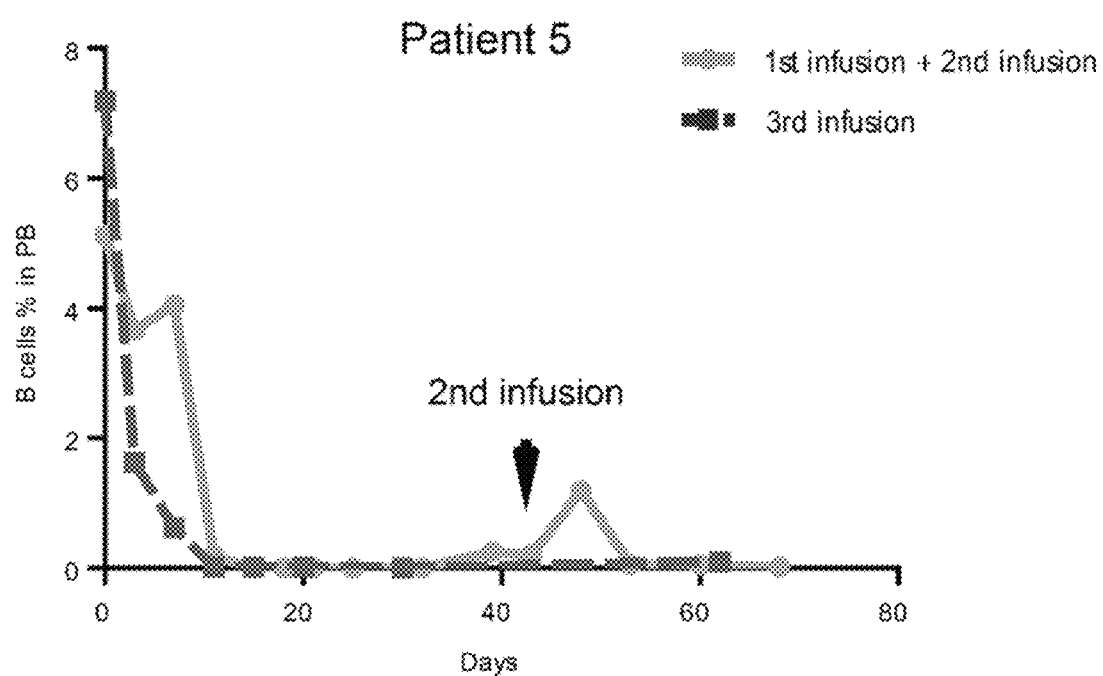

After infusion of hsCAR-T cells, various levels of expansion of hsCAR-T cells were detected in the PB of all five patients within three weeks post-infusion (FIGS. 13A-13D). Accordingly, the number and proportion of B cells in PB remained close to zero on day 30 in patient 1 and patient 3 who achieved CMR. In patient 2, who did not achieve CR, B cells started to be detected after day 20 (FIGS. 18A-18C). In patient 4, B cells started to be detected after day 30 (FIG. 18D); in patient 5, the proportion of B cells remained close to zero two months after hsCAR-T treatment (FIG. 18E). The cytokine concentrations in the PB were measured and presented in FIGS. 13E-13L. A surge of IL-2, IL-6, sCD25, and TNF-α levels was detected in the sera of patients 1 and 3, but not that of patient 2. A surge of IL-6 was also detected in patients 4 and 5.

Figure 14D:
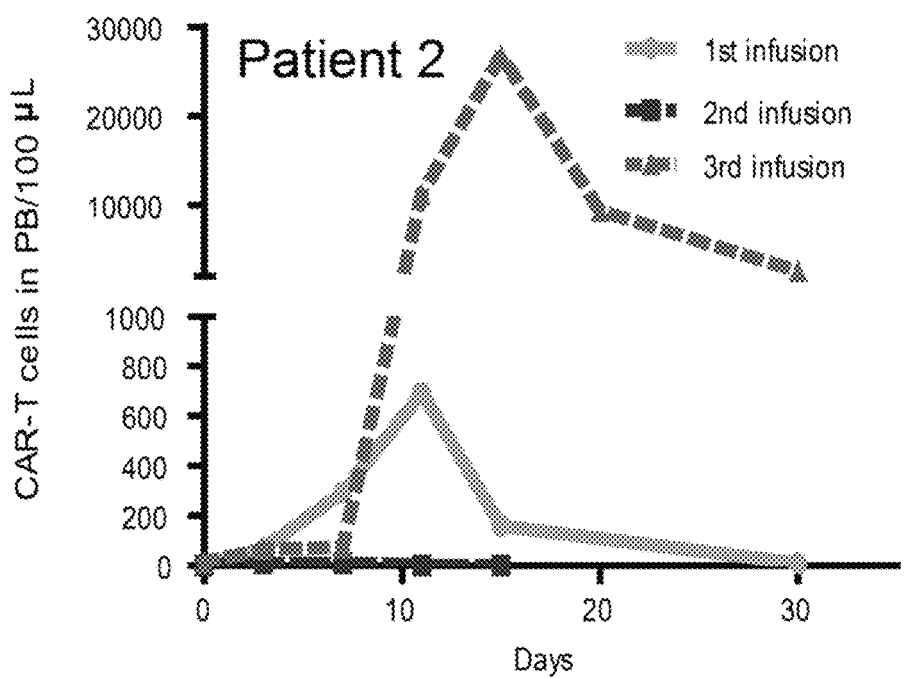
Figure 14E:
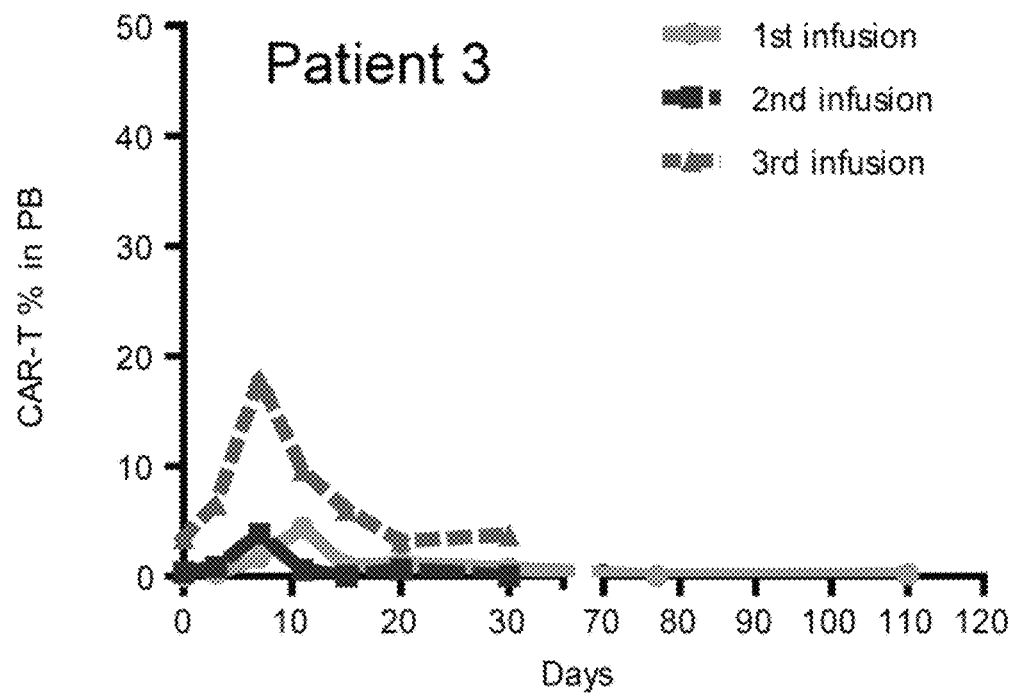
Figure 14F:
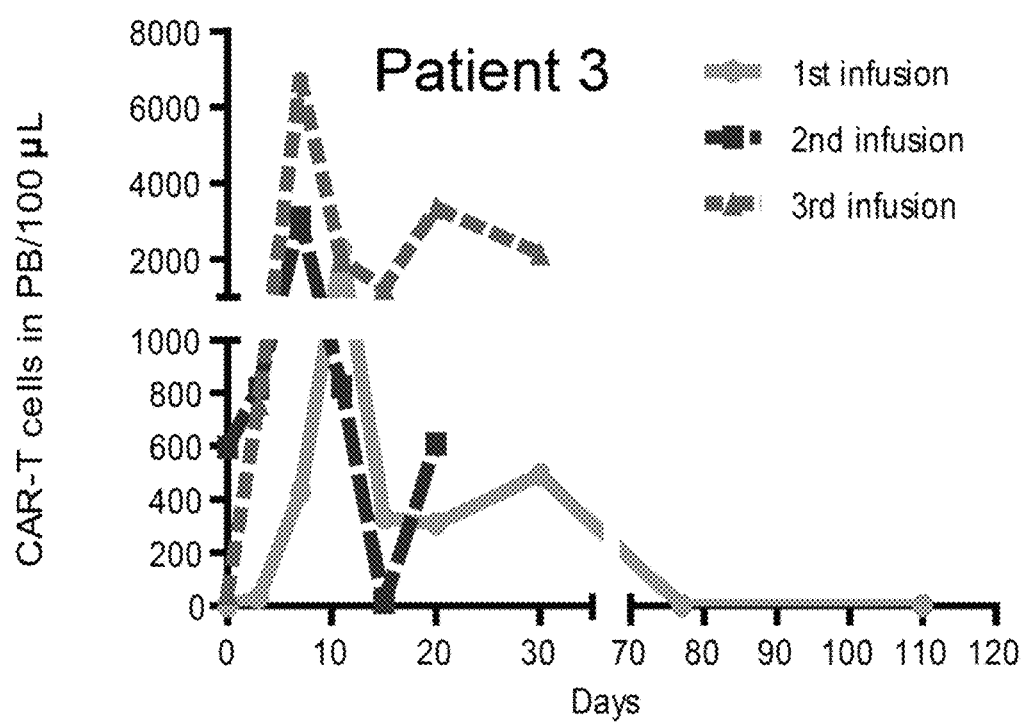
Figure 14G:
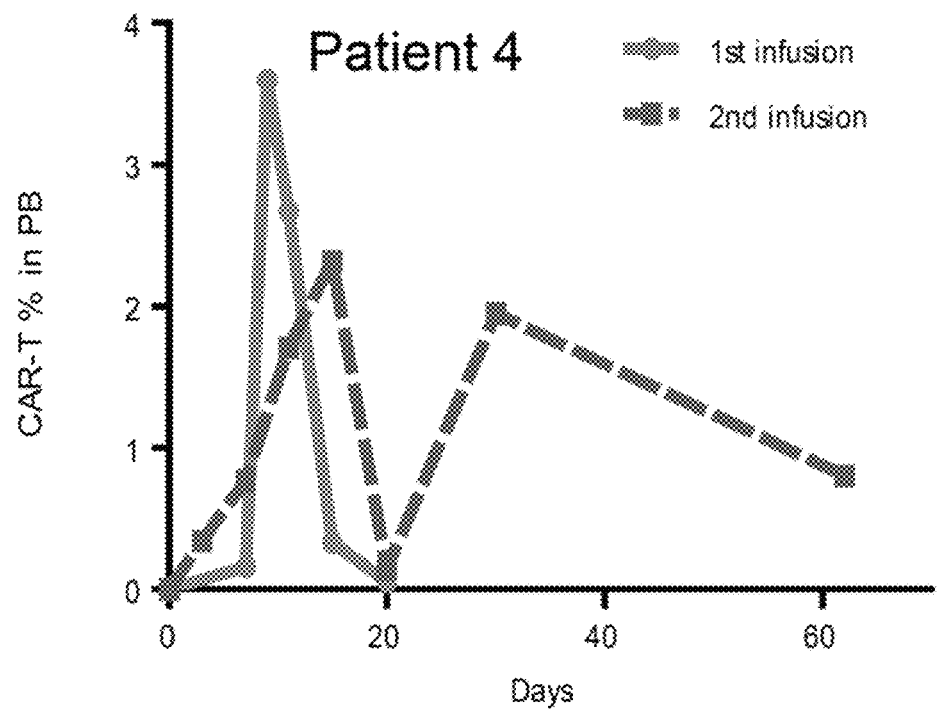
Figure 14H:
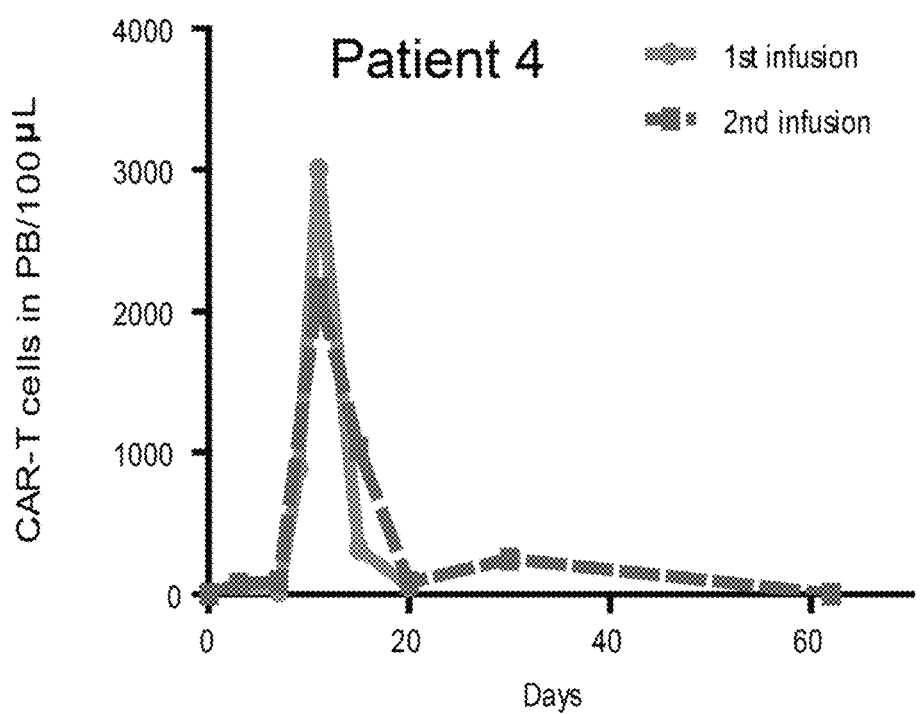
Figure 14I:
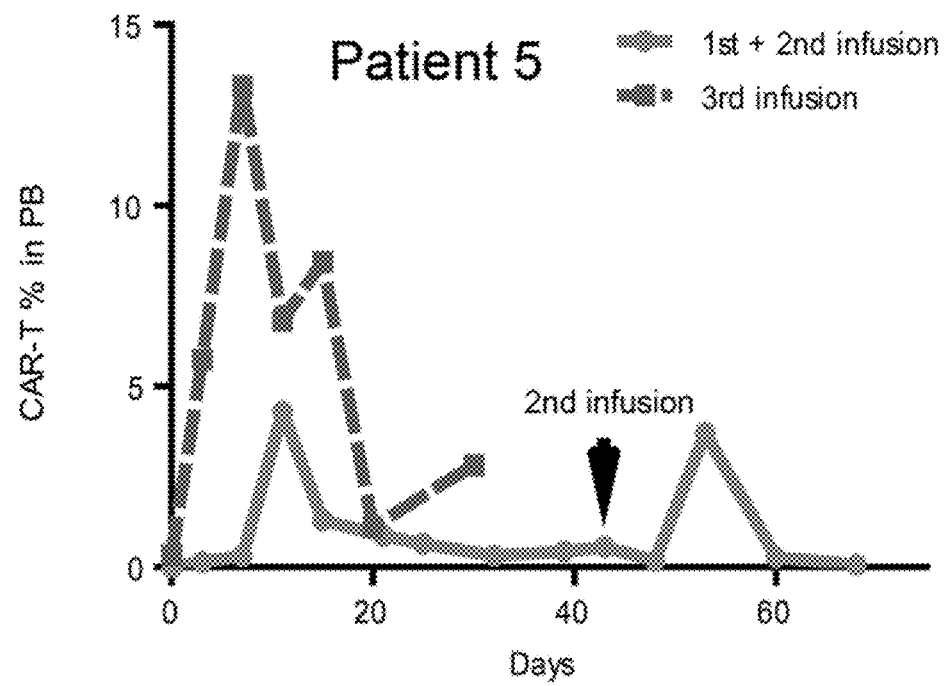
Figure 14J:
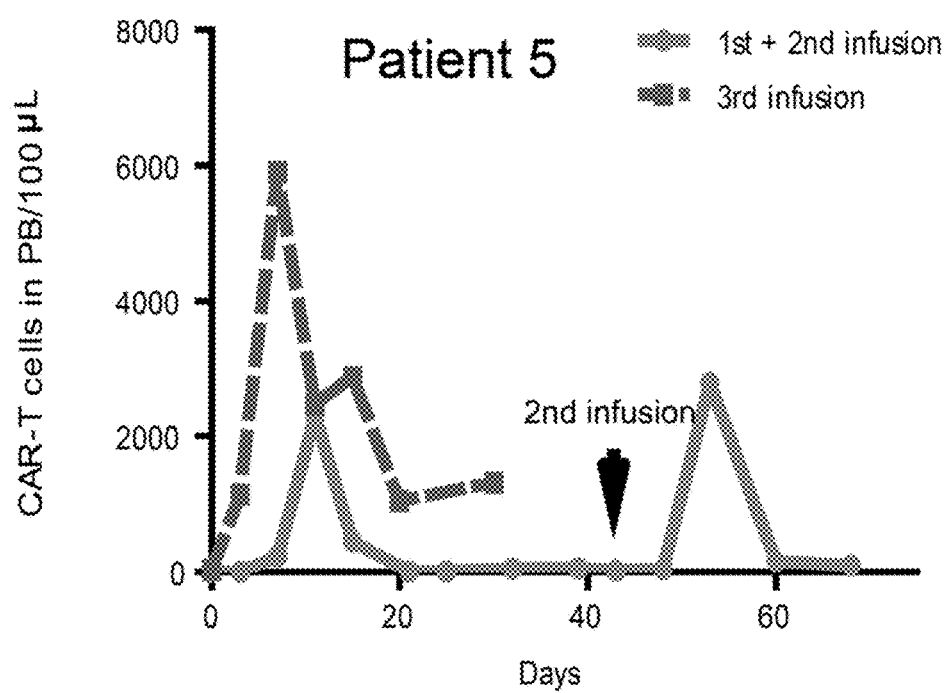

We also compared the expansion of CAR-T cells and cytokine levels after hsCAR-T vs. mCAR-T treatments (FIG. 14 and FIG. 19). Patient 1 received $0.3 \times 10^6$ mCAR-T/kg body weight and $1 \times 10^6$ hsCAR-T/kg body weight;

prior to the mCAR-T and hsCAR-T treatments, the tumor loads in BM were 5.04% and 4.00%, respectively. After treatments, the proportion of CAR-T cells in PB reached the highest value of 0.5% on day 3 following mCAR-T vs. 61% on day 11 following hsCAR-T treatment (FIG. 14A). The number of CAR-T cells in 100 µl PB reached the highest value of 43 on day 11 following mCAR-T vs. 15,000 on day 15 following hsCAR-T treatment (FIG. 14B). Patient 2 received twice mCAR-T and once hsCAR-T infusions and all the three were at the same dosage of $0.3 \times 10^6$/kg body weight. The tumor loads in BM before each of the 3 infusions were 0.43%, 0.50%, and 46.8%, respectively. The proportion of CAR-T cells in PB reached the highest value of 6.36% on day 11 following the first time mCAR-T infusion and remained close to zero following the second time mCAR-T infusion (FIG. 14C). In contrast, following subsequent hsCAR-T treatment, the proportion went up to 79.64% on day 15. The number of CAR-T cells in 100 µl PB reached the highest value of 693 on day 11 following the first time mCAR-T infusion vs. 26800 on day 15 following hsCAR-T infusion (FIG. 14D). Very few mCAR-T cells were detected following the second time mCAR-T infusion. As to patient 3, the peak of CAR-T expansion was detected earlier (day 7) following the second time mCAR-T infusion vs. following the first time mCAR-T infusion (day 11) (FIGS. 14E and 14F). Compared with the two mCAR-T treatments, the peak values of hsCAR-T cells were higher (17.96% vs. 4.45% and 3.85%, FIG. 14E; 6690/100 µL vs. 2280/100 µL and 3070/100 µL, FIG. 14F). Patient 4 and 5 both received mCAR-T treatments before HSC transplantation and hsCAR-T after. The percentages of CAR-T cells in PB and the numbers of CAR-T cells in 100 µL PB in patient 4 were comparable following mCAR-T vs. hsCAR-T treatments (FIGS. 14G and 14H). Patient 5 showed a higher degree of CAR-T expansion following hsCAR-T treatment compared with mCAR-T treatment (FIGS. 14I and 14J).

Figure 19A:
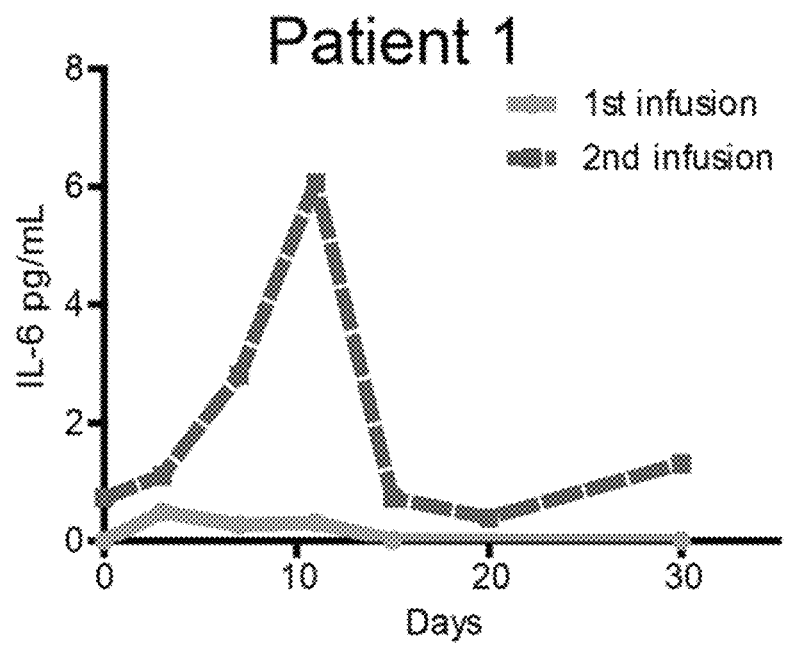
FIGS. 19A-19T show levels of IL-6, IFN-γ, IL-10 and sCD25 in Patients 1 to 5 measured by ELISA assay following multiple infusions of CD19 mCAR-T and CD19 hsCAR-T cells. Comparison of multiple cytokine levels related to CRS following treatments of CD19 mCAR-T vs. CD19 hsCAR-T were made.
Figure 19B:
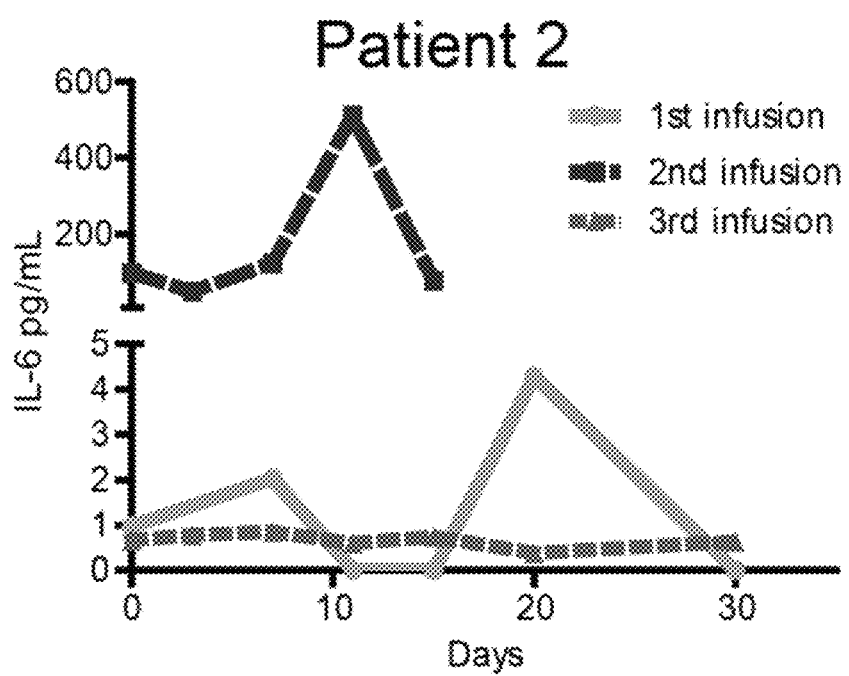
Figure 19C:
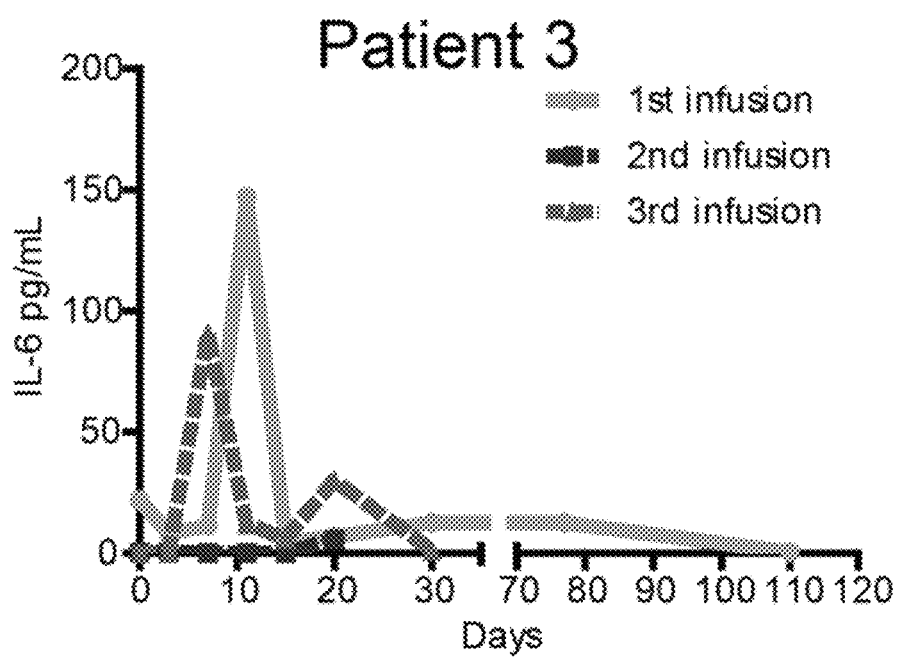
Figure 19D:
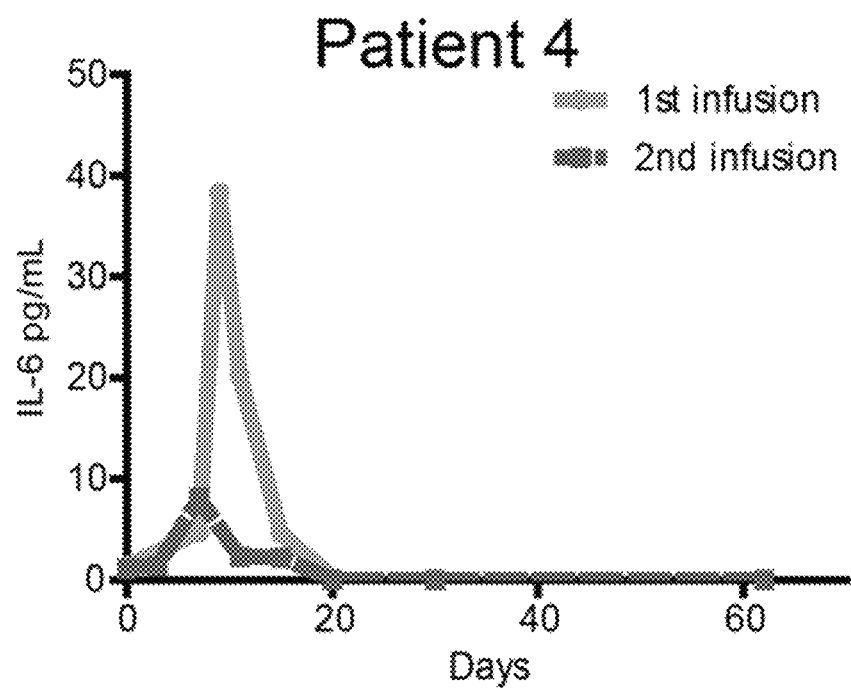
Figure 19E:
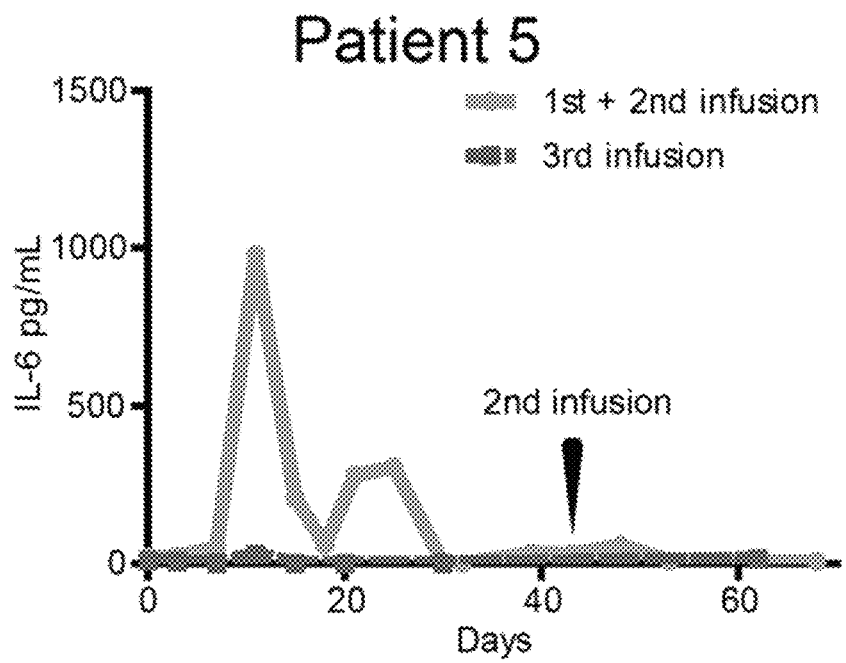
Figure 19F:
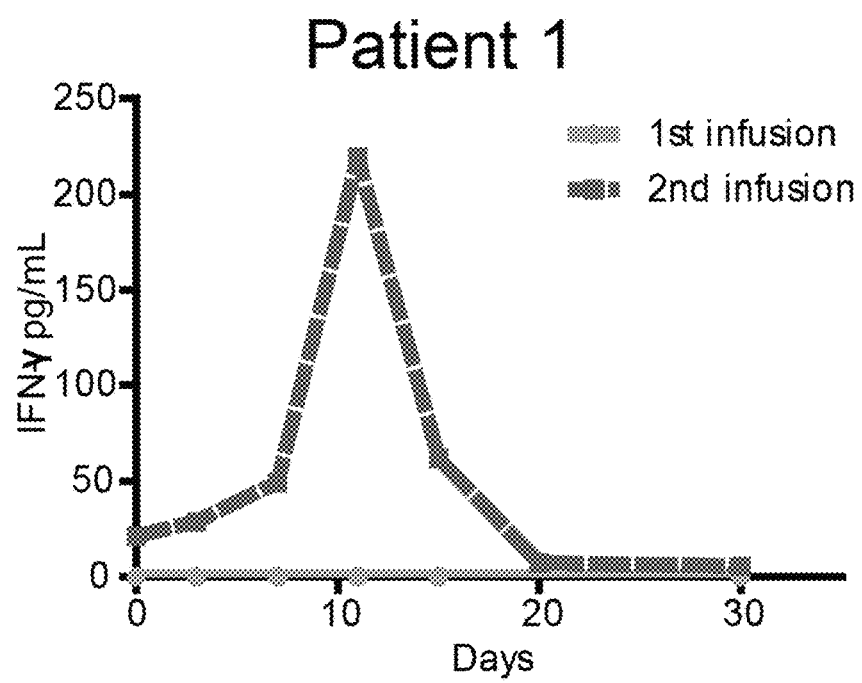
Figure 19G:
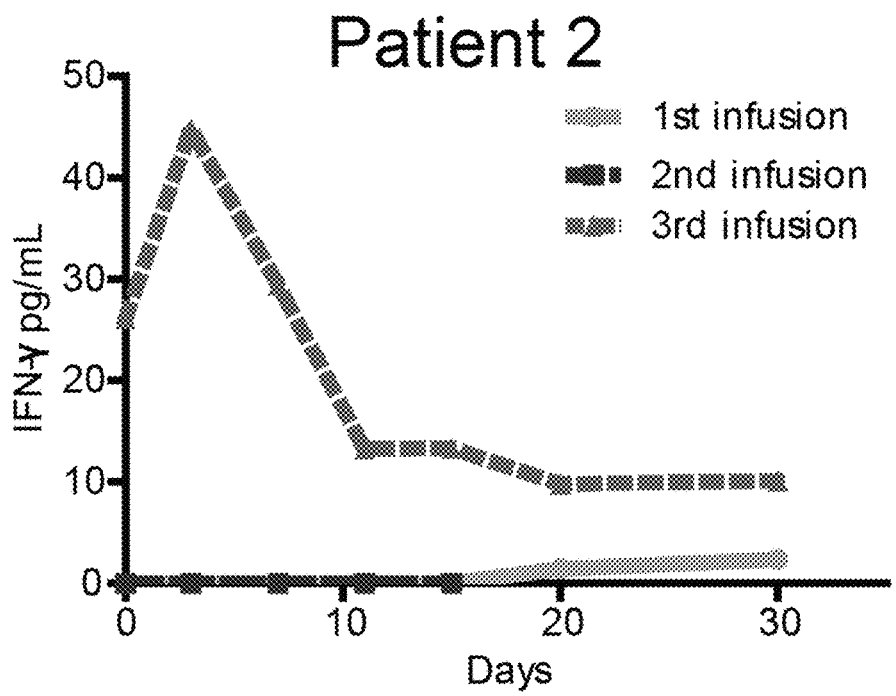
Figure 19H:
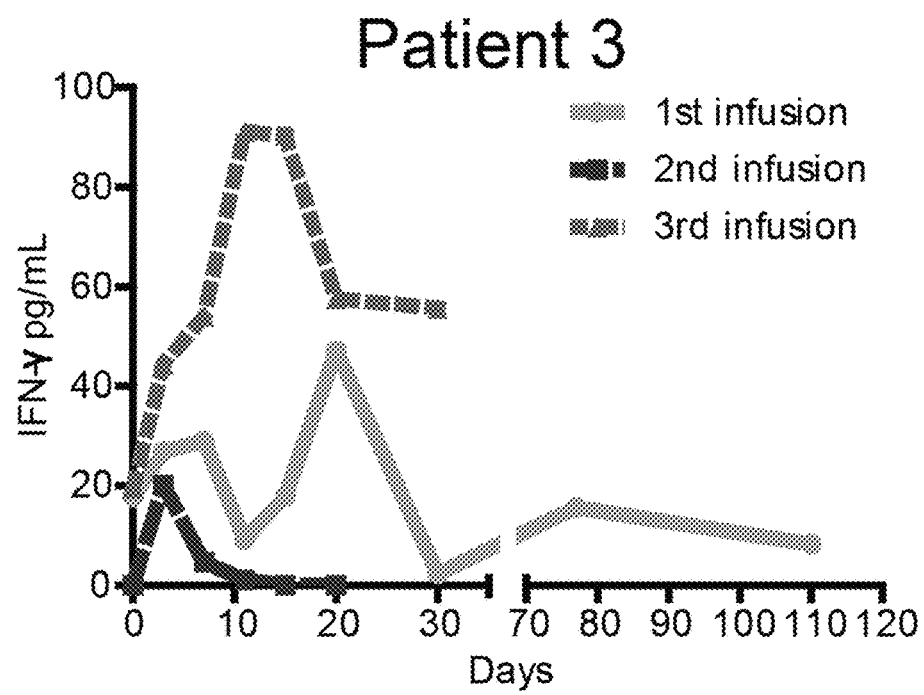
Figure 19I:
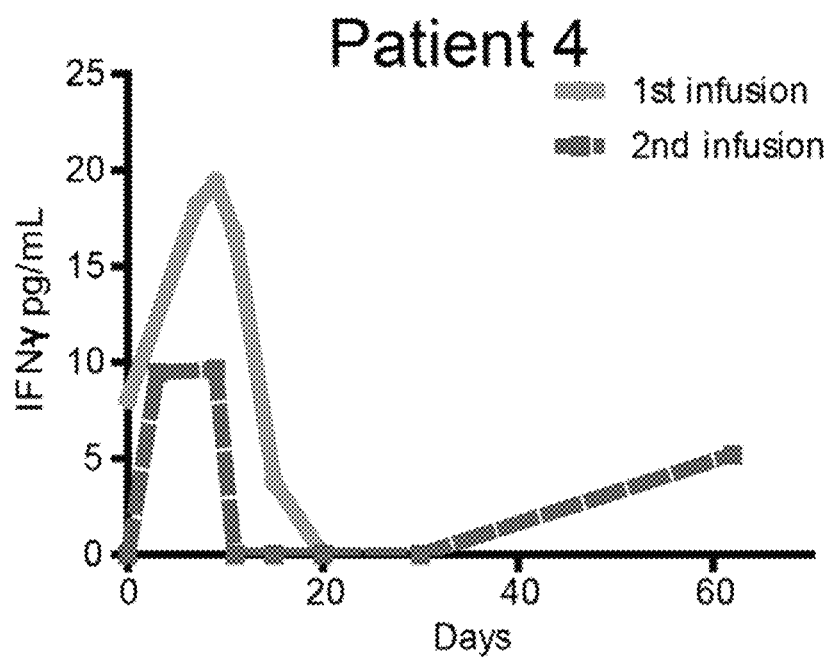
Figure 19J:
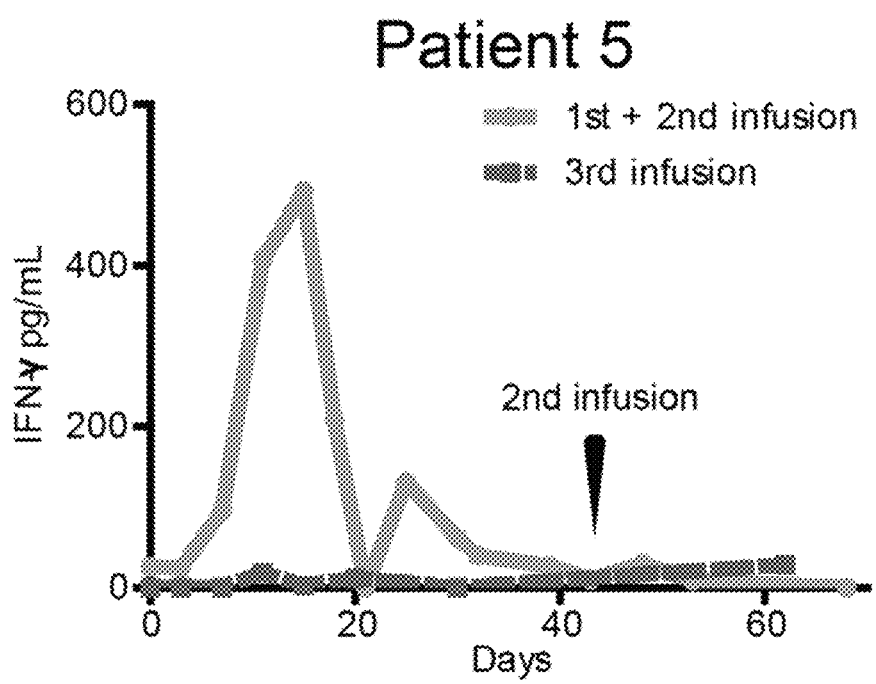
Figure 19K:
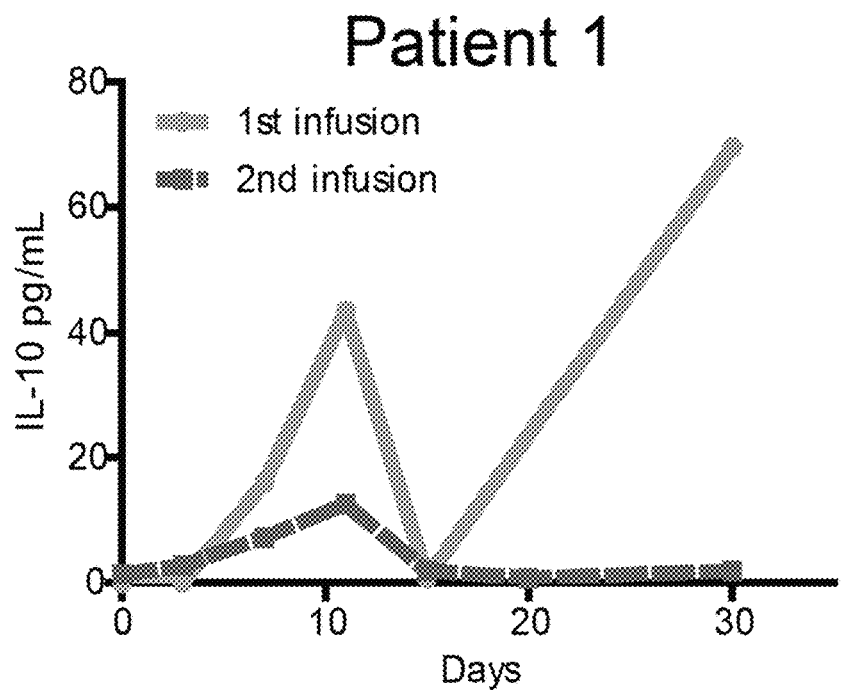
Figure 19L:
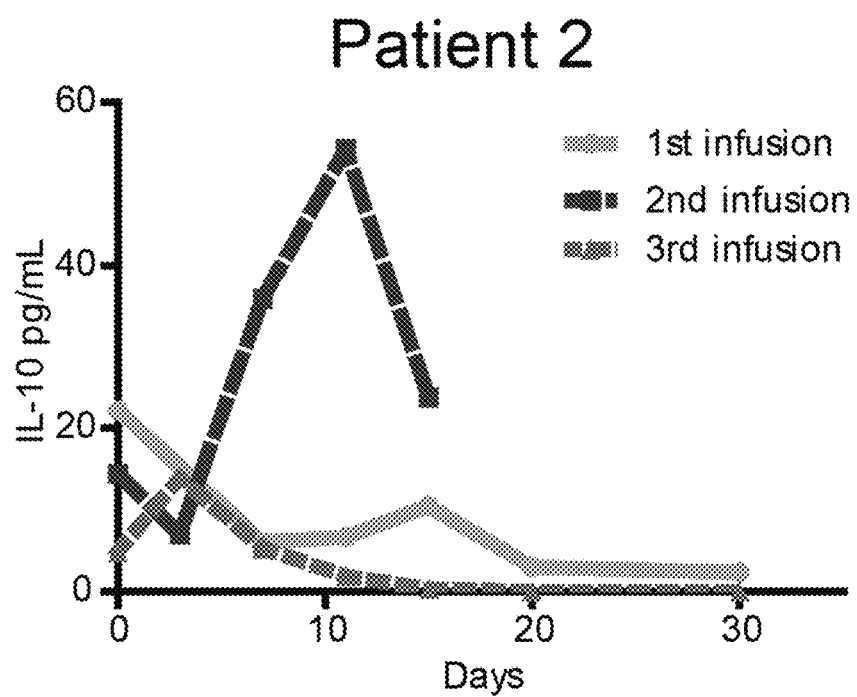
Figure 19M:
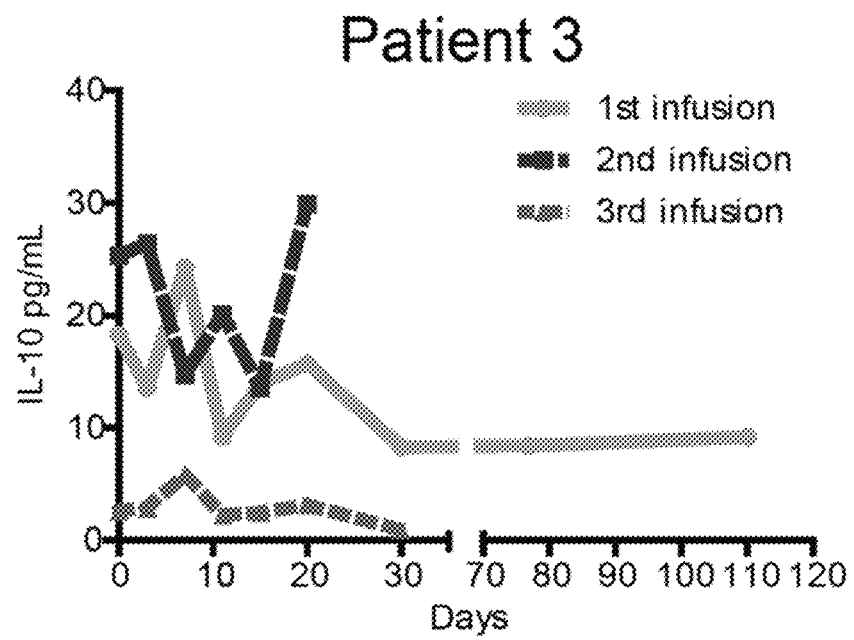
Figure 19N:
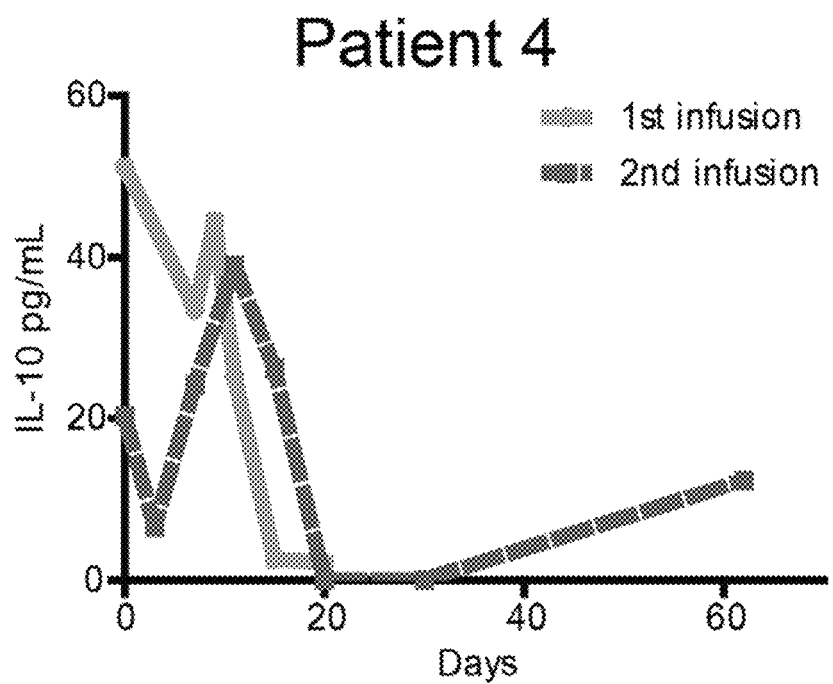
Figure 19O:
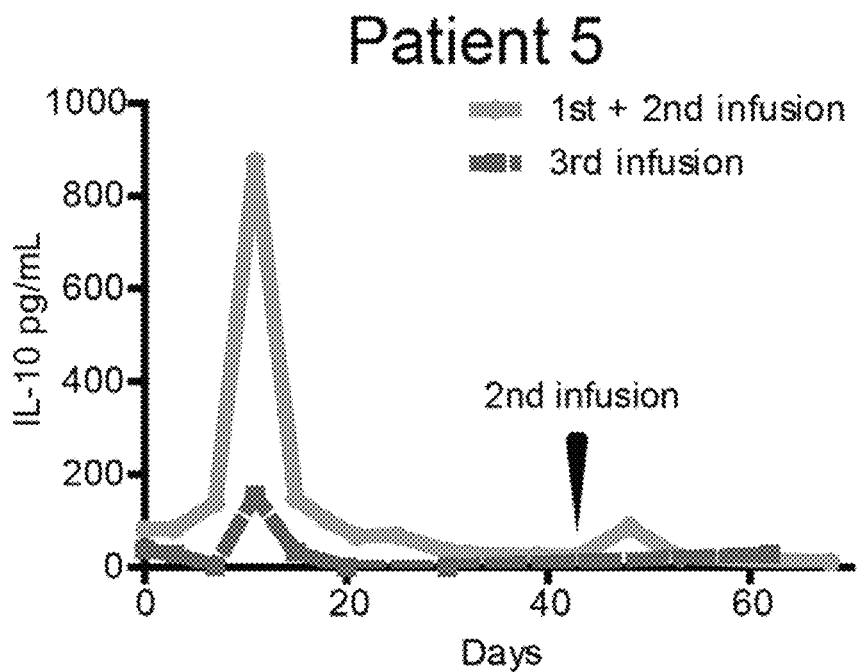
Figure 19P:
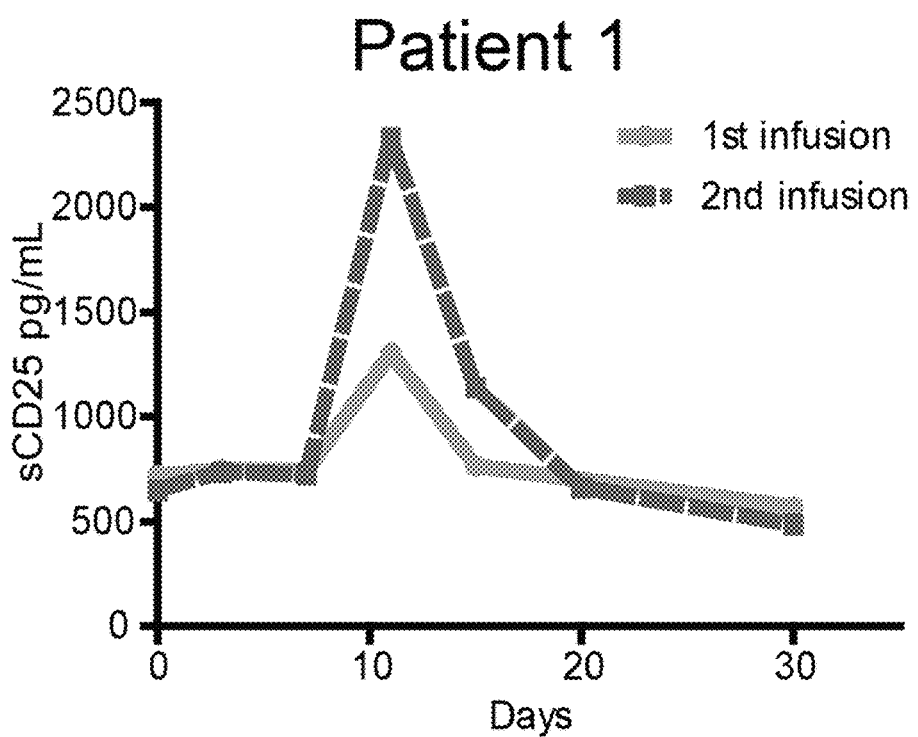
Figure 19Q:
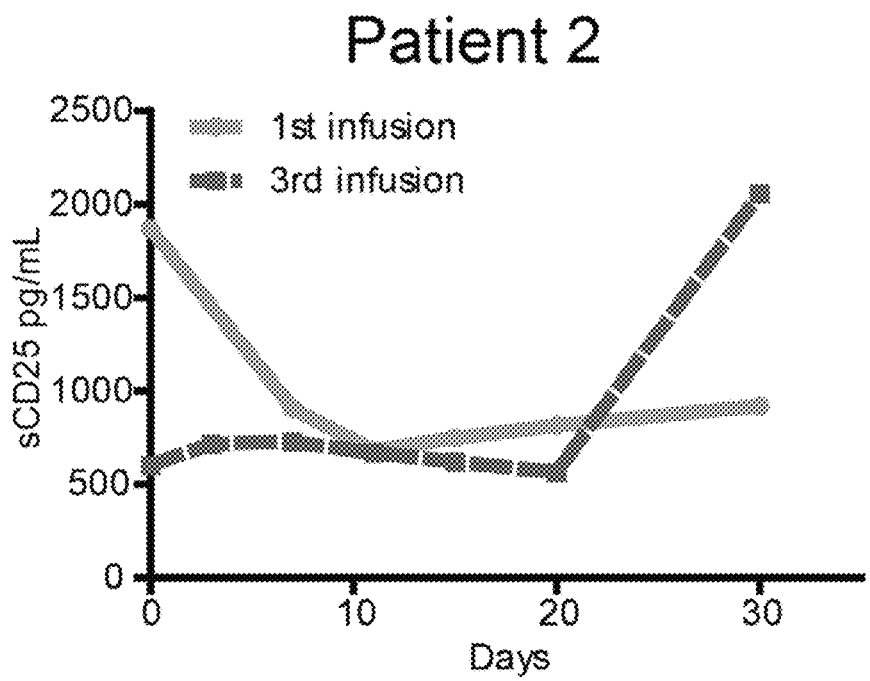
Figure 19R:
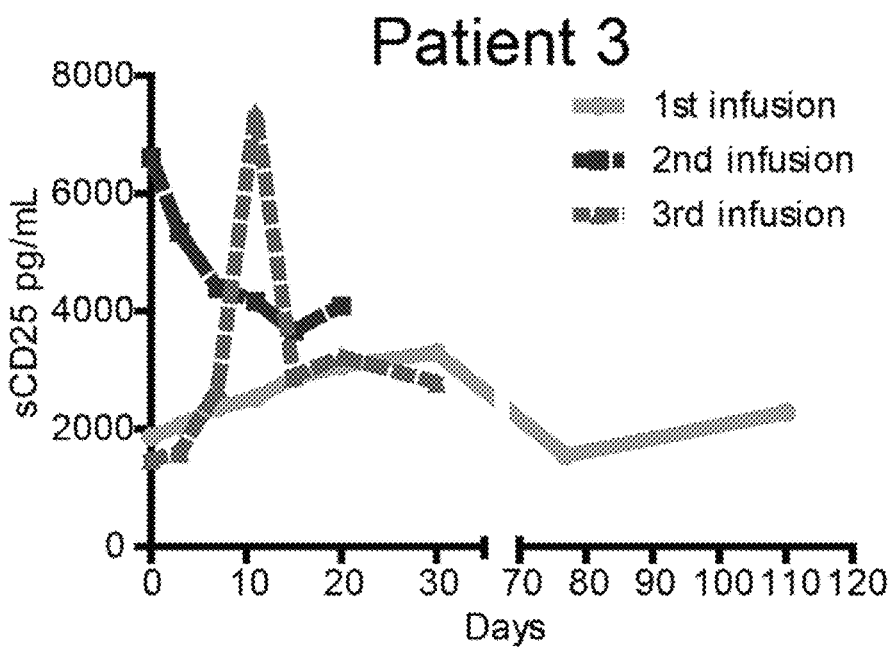
Figure 19S:
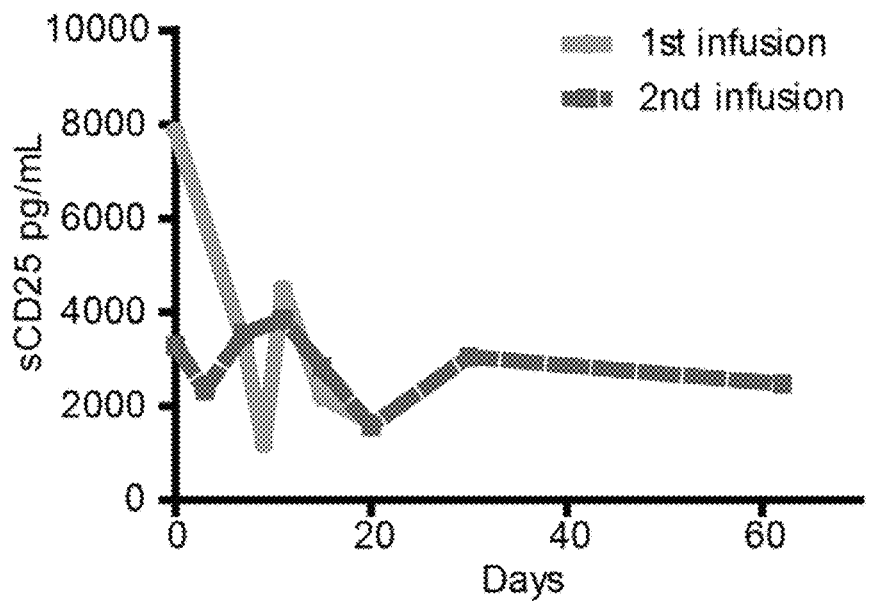
Figure 19T:
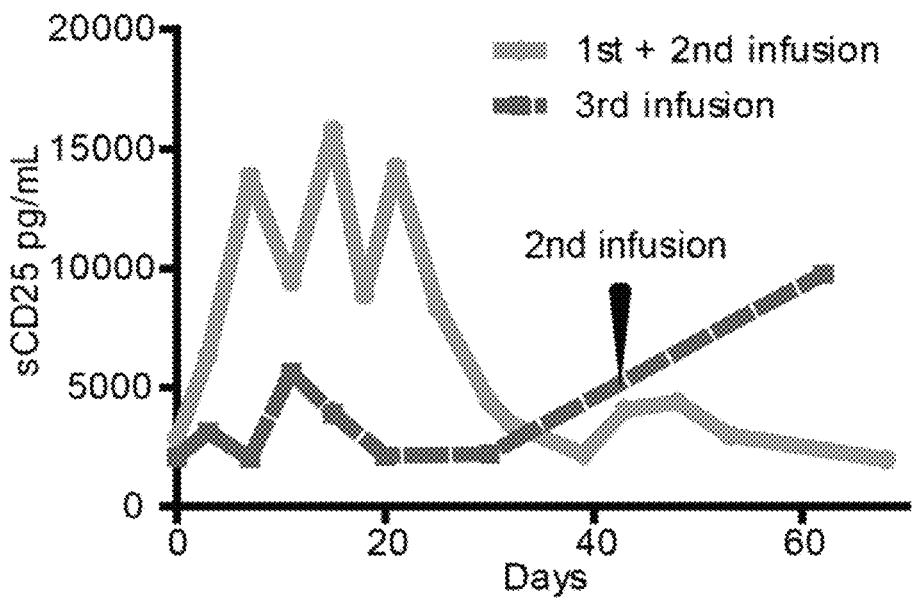

The cytokine levels in the sera of the five patients following each treatment were presented in FIGS. 19A-19T. With regard to patient 1, after mCAR-T treatment and relapse, hsCAR-T treatment still elicited pro-inflammatory cytokine response, such as IL-6 and IFN-γ (FIGS. 19A and 19F); and the level of anti-inflammatory cytokine, IL-10, was lower (FIG. 19K). As to patient 2, the second time mCAR-T treatment induced a surge in both IL-6 and IL-10. hsCAR-T treatment caused a higher expression of IFN-γ, compared with mCAR-T results. No data of sCD25 after the second time mCAR-T treatment was available for patient 2 (FIGS. 19B, 19G, 19L and 19Q). As to patient 3, after mCAR-T infusion for the second time, although the CAR-T cells seemed to have expanded to some extent (FIGS. 14E and 14F), proinflammatory cytokine response was dampened compared with that after the first time mCAR-T treatment (FIGS. 19C and 19H). However, hsCAR-T treatment following the two mCAR-T treatments elicited proinflammatory cytokine response (FIGS. 19C and 19H) and reduced the level of anti-inflammatory cytokine, IL-10 (FIG. 19M). In patient 4 and 5, levels of proinflammatory cytokines IL-6 and IFN-γ were both lower following hsCAR-T vs. mCAR-T treatments (FIGS. 19D, 19I, 19E and 19J), possible due to the suboptimal reconstruction of the hematopoietic system following HSC transplantation (Table 3), which might have subsequently affected the cytokine responses.

TABLE 3

Immune cell survey in PB before CD19 hsCAR-T treatment in patients 4 and 5

| | Patient No. | | |
| --- | --- | --- | --- |
| | 4 | 5 | |
| | Values | | |
| Examination | Measurement | Measurement | Normal range |
| Mature lymphocytes in Mononuclear cells | 28.50% | 38.95% | 15%-40% |
| Count of mature lymphocytes | 474/µL | 170/µL | 1530-3700/µL |
| Mature B cells in lymphocytes | 1.62% | 15.30% | 3%-12% |
| Count of mature B cells | 7/µL | 25/µL | 80-616/µL |
| T cells in lymphocytes | 96.47% | 79.27% | 35.5%-85% |
| Count of T cells | 457/µL | 134/µL | 723-2737/µL |
| CD4+ in T cells | 28.12% | 61.78% | 20.4%-49.4% |
| Count of CD4+ T cells | 138/µL | 107/µL | 404-1612/µL |
| CD8+ in T cells | 67.90% | 14.66% | 9.8%-40.4% |
| Count of CD8+ T cells | 333/µL | 25/µL | 220-1129/µL |
| CD4/CD8 | 0.41 | 4.21 | 1-2.5 |
| NK in lymphocytes | 1.12% | 1.78% | 5%-39.5% |
| Count of NK | 5/µL | 3/µL | 84-724/µL |
| NKT in lymphocytes | 1.64% | 1.42% | N/A |
| CD4+/CD25+ bri in CD4+ T cells | 2.07% | 4.28% | 0.5%-5% |
| CD4+/CD25+ dim in CD4+ T cells | 9.16% | 9.43% | N/A |
| Treg in CD4+ T cells | 1.17% | 3.14% | N/A |
| Count of Treg | 2/µL | 3/µL | N/A |

Figure 15A:
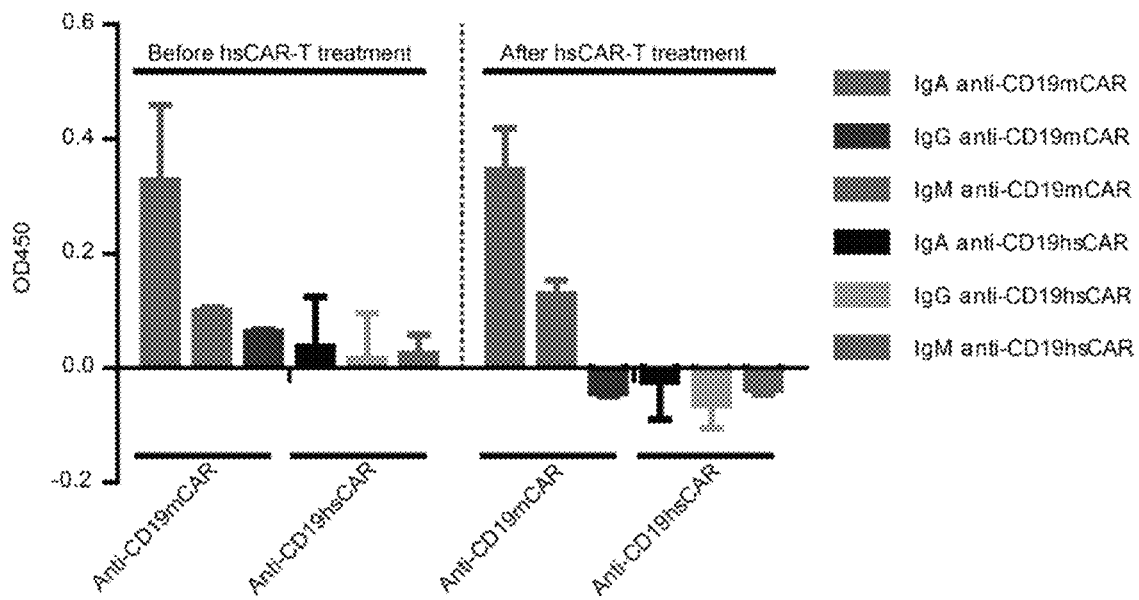
FIGS. 15A-15F show Anti-CAR response and attenuation of mCAR-mediated cytotoxicity by patients' sera.
Figure 15B:
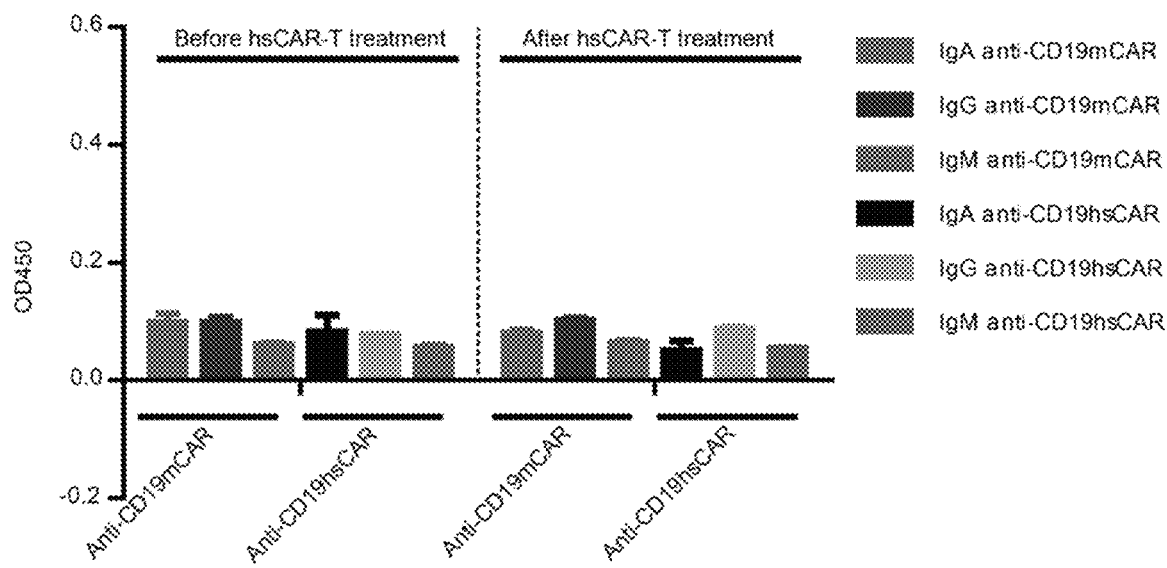
Figure 15C:
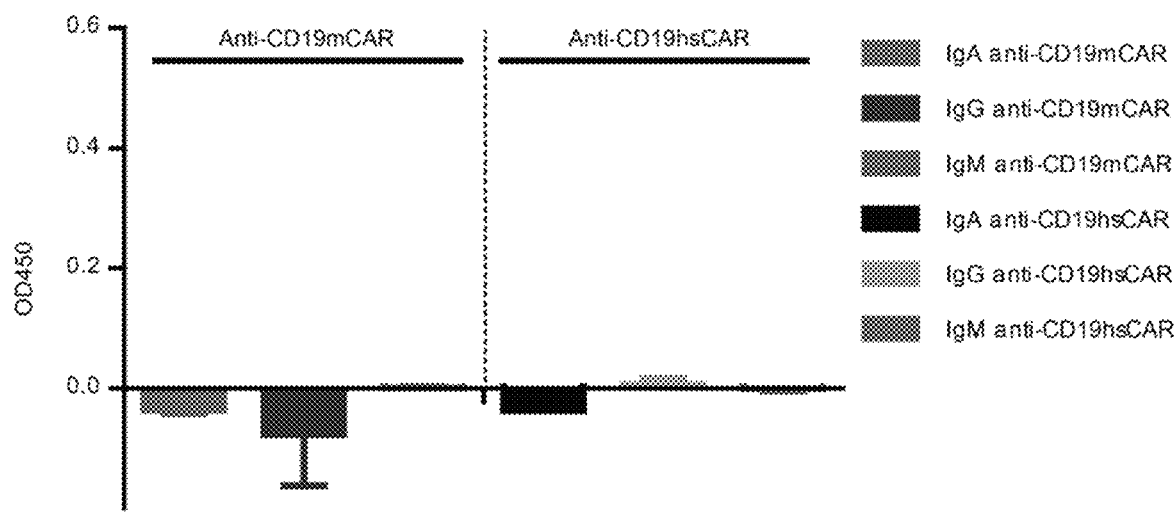

One of the reasons that might underlie the diminished efficacy following the second time murine CAR-T treatment in patients 2 and 3 was that the patients may have developed antibodies that recognized the murine scFv sequences. To test this hypothesis, we analyzed the sera isolated from the five patients (FIGS. 15A and 15B) and three healthy control people (FIG. 15C). The serum was tested for the reaction to the extracellular domains of murine and human CD19 CARs before and after hsCAR-T treatment. Patients 1-3 who received murine CD19 CAR-T cell treatment showed a positive IgA reaction to murine CAR; after treatment with hsCAR-T, no immunoglobulins reactive to human CAR was detected in the sera of the three patients (FIG. 15A). Similarly, sera from patient 4 and 5 did not show immunoglobulins reactive to human CAR (FIG. 15B), no blood samples available before HSC transplantation). The data of reactivity to murine and human CD19 CARs from each individual patient were presented in Table 4.

TABLE 4

Anti-CAR response in patients' sera before and after hsCAR-T treatment

| | | Antibodyisotypes | | | | | |
|---|---|---|---|---|---|---|---|
| | | IgA | | IgG OD450 | | IgM | |
| | | Detection time | | | | | |
| Sample ID | Antigen | Before hsCAR-T | After hsCAR-T | Before hsCAR-T | After hsCAR-T | Before hsCAR-T | After hsCAR-T |
| Patient 1 | CD19 mCAR | 0.590755 | 0.219637 | 0.0895341 | 0.092022 | 0.0562419 | −0.0511632 |
| | CD19 hsCAR | −0.122193 | −0.105871 | −0.143873 | −0.098112 | −0.0394008 | −0.026955 |
| Patient 2 | CD19 mCAR | 0.178135 | 0.345866 | 0.0974262 | 0.174307 | 0.0627561 | −0.043684 |
| | CD19 hsCAR | 0.18 | 0.107558 | 0.086011 | −0.111115 | 0.0524062 | −0.034588 |
| Patient 3 | CD19 mCAR | 0.212765 | 0.472216 | 0.113288 | 0.122573 | 0.0689928 | −0.036198 |
| | CD19 hsCAR | 0.053714 | −0.072719 | 0.105453 | 0.016531 | 0.0624112 | −0.0522147 |
| Patient 4 | CD19 mCAR | 0.083113 | 0.074954 | 0.0889832 | 0.0983526 | 0.0601998 | 0.0625049 |
| | CD19 hsCAR | 0.110526 | 0.06637 | 0.0775209 | 0.090287 | 0.0528421 | 0.0553977 |
| Patient 5 | CD19 mCAR | 0.113151 | 0.084973 | 0.107124 | 0.105014 | 0.0622423 | 0.0666344 |
| | CD19 hsCAR | 0.053769 | 0.034032 | 0.0782874 | 0.0856885 | 0.0603099 | 0.0525453 |
| HC 1 | CD19 mCAR | −0.042402 | | 0.0144479 | | 0.0020803 | |
| | CD19 hsCAR | −0.037279 | | 0.0160554 | | 0.0035765 | |
| HC 2 | CD19 mCAR | −0.019394 | | −0.1572369 | | −0.0015892 | |
| | CD19 hsCAR | −0.037279 | | −0.0048031 | | −0.0053109 | |

Note:
Patient 1 to Patient 3 received at least once murine-based CD19 CAR-T treatment before CD19 hsCAR-T therapy; Patient 4 and Patient 5 received CD19 hsCAR-T treatment after HSC transplantation; HC 1 and HC 2 were healthy donors as negative controls.

Figure 15D:
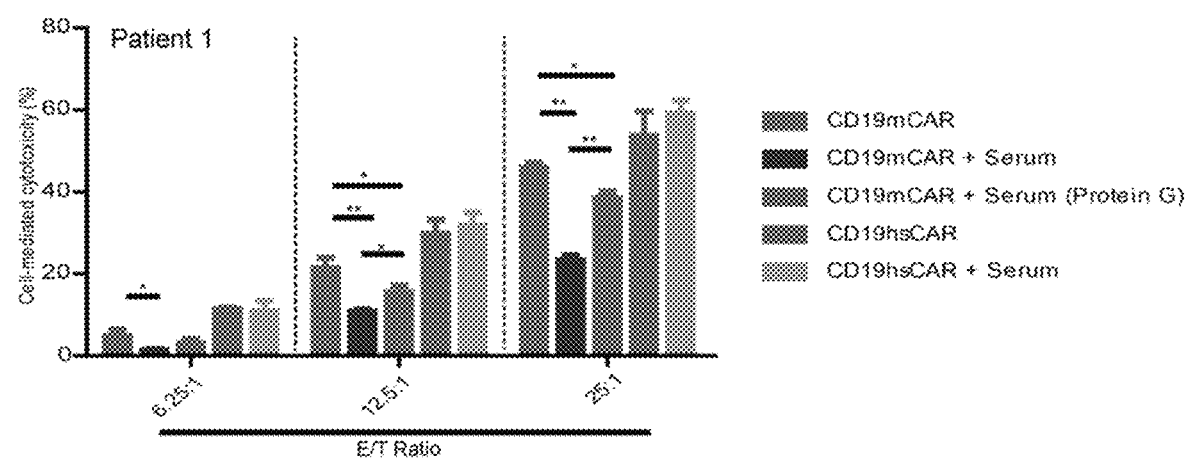
Figure 15E:
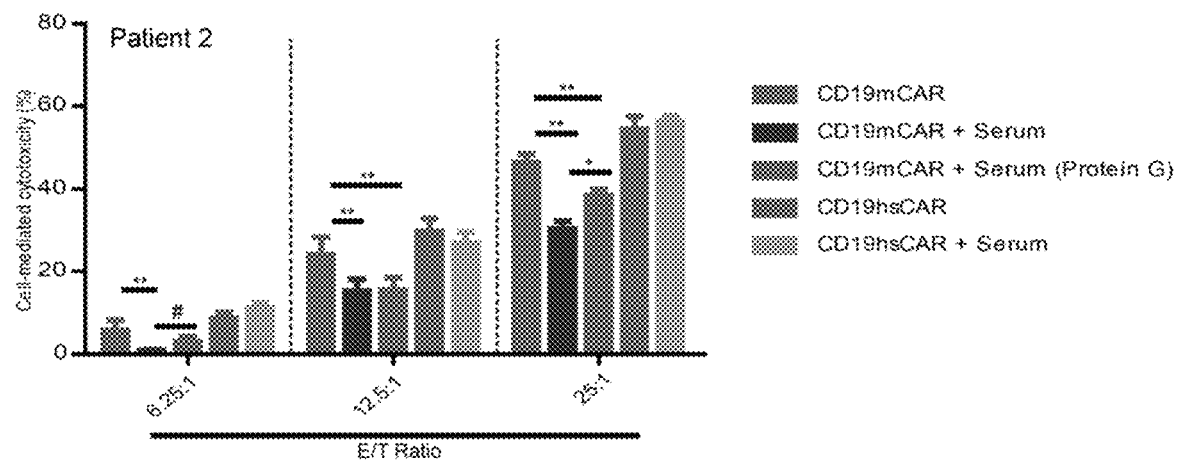
Figure 15F:
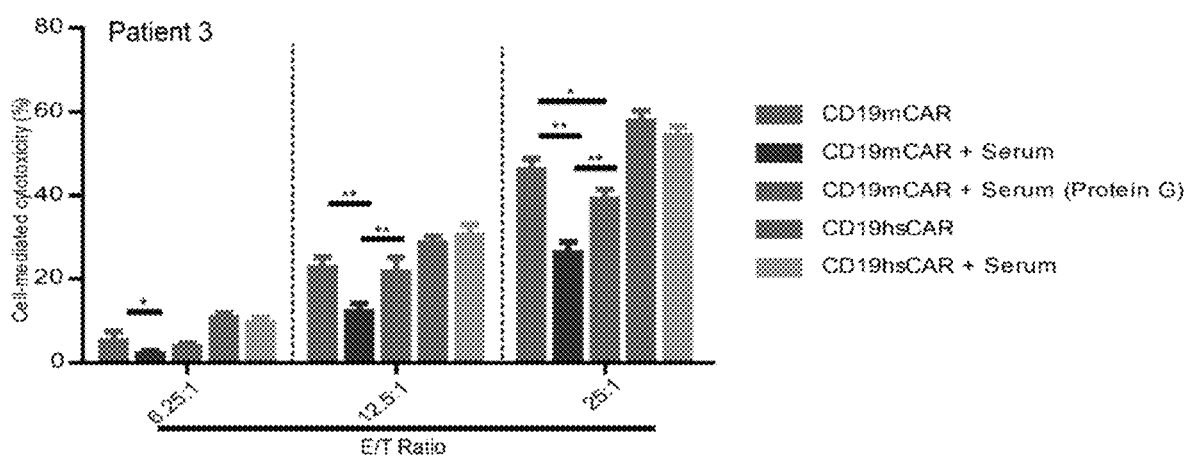

To further confirm the inhibitory effects, T cells derived from the patients 1-3 were infected with murine CAR or hsCAR, and co-cultured with the leukemia Raji cell line at different E/T ratios with or without patient serum, to test the cytotoxic functions. In one experimental group, protein G was added together with the serum to block the effects of immunoglobulins (FIGS. 15D-15F). The cytotoxic functions of mCAR-T cells were inhibited by the patient serum, and incubation with protein G could rescue the inhibitory effects. In contrast, the cytotoxicity of hsCAR-T cells was not inhibited by patient serum (FIGS. 15D-15F).

One issue associated with the current CAR-T production process was that both CAR-transduced and non-transduced T cells were expanded. To solve this problem, we developed the selective CD19 CAR. After activation with coated SmAb, CAR-transduced T cells in the final product were increased from 32.2% to 64.3% (FIG. 10H); the percentage was almost doubled. The yield of total CD3+ T cells on day 14 was also significantly greater, achieving around 80-fold expansion with SmAb stimulation vs. around 60-fold expansion without (FIG. 10F). Theoretically, hsCAR-transduced T cells can be further purified by magnetic sorting using beads-conjugated SmAb, an approach that can be used to address whether CAR-negative T cells affect efficacy. In addition, after infusion into patients, the activity of hsCAR-T cells may be possibly regulated/modified by injection of clinical grade SmAb. Another merit of the selective CAR was that stimulation with SmAb during expansion stage can re-shape the composition of T cell subpopulations, leading to a higher proportion of Tcm in the product. Previous studies have shown that persistence of GD2 CAR-T cells is concordant with the percentage of Tcm in the final product. In our study, leukemia mouse models treated with SmAb-stimulated hsCAR-T cells displayed a longer survival time compared with the other groups (FIGS. 12C and 12D), suggesting an improved anti-tumor efficacy associated with hsCAR-T cells. The CD4/CD8 ratios in the final products for the five patients were also measured and presented in Table 5. It seemed that a large variation existed in the CD4/CD8 ratios between the final products of each individual.

TABLE 5

Subpopulation analysis of the final products for the five patients

| | | Patient No. | | | | |
|---|---|---|---|---|---|---|
| | | 1 | 2 | 3 | 4 | 5 |
| Starting PBMCs | CD3+ in PBMCs | 29.8% | 32% | 6.9% | 46.2% | 8.1% |
| | CD19+ in PBMCs | 0.7% | 0.8% | 1.95% | 1.0% | 2.1% |
| | CD27+CD45RO−PD-1− in CD8+ | 25.9% | 31.4% | 8.28% | 38.1% | 25.9% |
| | Starting PBMC (×$10^8$) | 2.7 | 2.88 | 3.45 | 2.51 | 2.1 |
| | Ratio of CD4/CD8 | 0.54 | 0.68 | 2.3 | 1.87 | 1.35 |
| Final Product (FP) | CD3+ in FP | 98.4% | 97.7% | 95.0% | 98.7% | 91.3% |
| | CD19+ in FP | OOL | OOL | OOL | OOL | OOL |
| | CD27+CD45RO−PD-1− in CD8+ | 12.7% | 7.28% | 13.75% | 15.3% | 48.1% |
| | Final product (×$10^7$) | 57.5 | 58.5 | 67.6 | 31.4 | 35.2 |
| | CAR % in CD3+ | 49.5% | 39.3% | 38.1% | 35.1% | 33.3% |
| | Ratio of CD4/CD8 | 0.17 | 8.4 | 1.06 | 0.87 | 1.00 |

Note:
FP: Final product; OOL: out of limit.

The other major improved feature of the current CAR design was the humanized scFv sequence. This hsCAR showed a 6-fold higher affinity to CD19, compared with the murine counterpart. Other groups also reported the design of humanized CD19 CARs, but the affinity was comparable to the murine counterpart and no clinical results were shown. At a higher E/T ratio which may lead to a saturated cytotoxic effect, hsCAR-T cells with a higher affinity and mCAR-T cells with a lower affinity showed comparable anti-tumor cytotoxicity. At a lower E/T ratio, hsCAR-T cells exhibited a better cytotoxicity (FIG. 11A). The enhanced affinity may be particularly useful when conditions do not permit a high infusion dosage, for example, to avoid severe side effects in patients. The comparable efficacies as observed in the animal experiments in mCAR-T group vs. hsCAR-T group without SmAb stimulation were probably due to the saturated dosage of CAR-T cells in vivo (FIG. 12D). Also, the microenvironments in which humanized CAR-T cells kill human leukemia Raji cells were different in mice vs. in humans. The mouse milieu may not preferably favor humanized CAR over murine CAR to implement their functions.

Humanized CAR-T cells have a potential to break the barrier caused by immune recognition of murine scFv following repetitive infusions of murine CAR-T cells. To date, all the other reported CD19 CAR-T clinical trials employed murine scFv CARs. The two FDA-approved products, Kymriah and Yescarta, were also based on murine scFv sequences. Many of those patients will relapse eventually, even if CAR-T therapy is bridged to allo-HSC transplantation. With an increasing number of patients undergoing such treatments, there is a pressing need to find a new interventional strategy to treat the patients who have relapsed with CD19+ leukemia cells after receiving murine CAR-T therapies. In this study, we enrolled five highly treated, refractory/relapsed, B-ALL patients who had exhausted all available options and who might represent different complex conditions. Patients 2 and 3 both received twice mCAR-T treatments. After the second time, mCAR-T cells failed to expand in patient 2 (FIGS. 14C and 14D); mCAR-T cells in patient 3 expanded to some extent after the second time (FIGS. 14E and 14F) but without triggering proinflammatory cytokine response (FIGS. 19C and 19H) or influencing B cell percentages in the PB (FIG. 18C). Analysis of the sera from the three patients revealed that there were IgA that were reactive to the extracellular domain of CD19 mCAR (FIG. 15A). We further confirmed that there was an inhibitory component in the patient serum that could reduce the cytotoxic effect of mCAR-T cells (FIGS. 15D-15F), and the inhibitory effect was reversed by pulling down immunoglobulins through adding protein G (FIGS. 15D-15F). It was unclear whether patient 4 and 5 had developed antibodies to murine CAR before HSC transplantation due to the unavailability of the blood samples prior to transplantation. Even though they had, the HSC transplantation process would have eliminated the B cell clones that produced those antibodies in the recipient, and reconstructed the hematopoietic system with the cells of the donor genotype. The cases of patient 4 and 5 indicated that hsCAR-T may also replace mCAR-T as an earlier treatment line option. The comparison of efficacies of hsCAR-T vs. mCAR-T would require a separate study with a larger patient cohort. In all of the five patients, no antibodies reactive to the hsCAR were detected in the sera, suggesting that hsCAR-T might be repetitively administered to the patients and remain efficacious. Yet further work is needed to test this.

The five patients represented various complex conditions. Patient 2 and 5 exhibited complex chromosomes; patient 3 had Philadelphia chromosome and CNS involvement. All of the above factors are associated with poor prognosis with conventional treatments. Patient 1 and 2 did not undergo HSC transplantation; patient 3 went through HSC transplantation before murine CAR-T treatments; patient 4 and 5 received HSC transplantation bridging to murine CAR-T therapies. For patients 3, 4 and 5, we used the healthy HSC donors' PBMCs for production of CAR-T cells, and no symptoms of graft-versus-host disease (GvHD) were observed. The results suggest that CD19 hsCAR-T may be employed in a wide spectrum of situations involved in B-cell malignancies.

Another noteworthy result was that the five patients all showed very mild side effects after hsCAR-T treatment. Only a temporary fever occurred which quickly resolved. The CRS was only at grade 1 for all the five patients. The mild side effects might be due to the higher affinity of the binding domain and/or the humanized nature of the CAR.

In summary, the humanized selective CD19 CAR is superior to its murine counterpart in terms of the antigen-binding affinity, product yield, purity, and in vitro anti-tumor efficacy. The results from the highly treated patients confirmed that hsCAR-T therapy is effective to treat those who have relapsed from murine CAR-T therapies.

All documents mentioned in the present application are hereby incorporated by reference as if each document is individually incorporated by reference. In addition, it should be understood that various modifications and changes may be made without departing from the disclosure of the invention. These equivalents also fall within the scope defined by the appended claims.

What is claimed is:

1. A chimeric antigen receptor of formula (I):

$$F_0\text{-}F_1\text{-}L_1\text{-}Z\text{-}L_2\text{-}F_2\text{-}H\text{-}TM\text{-}C\text{-}CD3\zeta \quad (I);$$

wherein, $F_0$ is absent or a signal peptide sequence;

one of $F_1$ and $F_2$ is a heavy chain variable region of an anti-human CD19 single-chain antibody, and the other is a light chain variable region of the anti-human CD19 single-chain antibody;

Z is a selective domain having an amino acid sequence as shown in positions 151-160 of SEQ ID NO: 8, positions 151-158 of SEQ ID NO: 12 or positions 151-159 of SEQ ID NO: 13;

$L_1$ and $L_2$ are independently absent or a linker peptide;

H is absent or a hinge region;

TM is a transmembrane domain;

C is absent or a co-stimulatory signal receptor tyrosine-based activation motif;

CD3ζ is a cytoplasmic signal transduction sequence; and

"-" is a linker peptide or a peptide bond;

wherein the amino acid sequence of the chimeric antigen receptor is shown as SEQ ID NO: 8, SEQ ID NO: 12 or SEQ ID NO: 13.

2. An isolated polynucleotide, wherein the polynucleotide encodes the chimeric antigen receptor (CAR) of claim 1; and the sequence of the polynucleotide is shown as SEQ ID NO: 7.

3. A method of treating a cancer or tumor in a patient, comprising administering to the patient an effective amount of a composition comprising the chimeric antigen receptor of claim 1 and a pharmaceutically acceptable carrier or excipient.

4. The method of claim 3, the tumor is selected from hematologic malignancy, solid tumor or a combination thereof.

* * * * *